United States Patent
Eggan et al.

(10) Patent No.: US 9,594,075 B2
(45) Date of Patent: Mar. 14, 2017

(54) DIAGNOSTIC METHODS FOR NEURAL DISORDERS

(71) Applicant: Q-STATE BIOSCIENCES, INC., Cambridge, MA (US)

(72) Inventors: Kevin C. Eggan, Boston, MA (US); Adam Cohen, Cambridge, MA (US); Joel Kralj, Somerville, MA (US); Evangelos Kiskinis, Cambridge, MA (US)

(73) Assignee: Q-State Biosciences, Inc., Cambridge, MA (US)

(*) Notice: Subject to any disclaimer, the term of this patent is extended or adjusted under 35 U.S.C. 154(b) by 0 days.

(21) Appl. No.: 14/692,242

(22) Filed: Apr. 21, 2015

(65) Prior Publication Data

US 2015/0301029 A1    Oct. 22, 2015

Related U.S. Application Data

(60) Provisional application No. 61/982,589, filed on Apr. 22, 2014.

(51) Int. Cl.
| | |
|---|---|
| *G01N 33/50* | (2006.01) |
| *G01N 33/487* | (2006.01) |
| *G01N 33/68* | (2006.01) |
| *C12N 5/0793* | (2010.01) |
| *G01N 21/64* | (2006.01) |

(52) U.S. Cl.
CPC ..... *G01N 33/48728* (2013.01); *C12N 5/0619* (2013.01); *G01N 21/6486* (2013.01); *G01N 33/502* (2013.01); *G01N 33/5023* (2013.01); *G01N 33/5058* (2013.01); *G01N 33/5091* (2013.01); *G01N 33/6872* (2013.01); *C12N 2502/081* (2013.01); *C12N 2510/00* (2013.01); *G01N 2333/705* (2013.01); *G01N 2800/2842* (2013.01); *G01N 2800/302* (2013.01)

(58) Field of Classification Search
CPC ................................................ G01N 33/5058
See application file for complete search history.

(56) References Cited

U.S. PATENT DOCUMENTS

| | | | |
|---|---|---|---|
| 5,356,802 A | 10/1994 | Chandrasegaran |
| 5,436,150 A | 7/1995 | Chandrasegaran |
| 5,487,994 A | 1/1996 | Chandrasegaran |
| 5,591,444 A | 1/1997 | Boss, Jr. |
| 5,789,538 A | 8/1998 | Rebar et al. |
| 5,925,523 A | 7/1999 | Dove et al. |
| 6,007,988 A | 12/1999 | Choo et al. |
| 6,013,453 A | 1/2000 | Choo et al. |
| 6,140,466 A | 10/2000 | Barbas, III et al. |
| 6,200,759 B1 | 3/2001 | Dove et al. |
| 6,242,568 B1 | 6/2001 | Barbas, III et al. |
| 6,243,197 B1 | 6/2001 | Schalz |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,534,261 B1 | 3/2003 | Cox, III et al. |
| 6,607,882 B1 | 8/2003 | Cox, III et al. |
| 6,885,492 B2 | 4/2005 | DeSimone et al. |
| 6,898,004 B2 | 5/2005 | Shimizu et al. |
| 6,903,185 B2 | 6/2005 | Kim et al. |
| 6,972,892 B2 | 12/2005 | DeSimone et al. |
| 7,153,949 B2 | 12/2006 | Kim et al. |
| 7,459,333 B2 | 12/2008 | Richards et al. |
| 7,560,709 B2 | 7/2009 | Kimura et al. |
| 7,964,853 B2 | 6/2011 | Araya |
| 8,202,699 B2 | 6/2012 | Hegemann et al. |
| 8,403,160 B2 | 3/2013 | Hentzel |
| 8,532,398 B2 | 9/2013 | Filkins et al. |
| 8,562,658 B2 | 10/2013 | Shoham et al. |
| 8,580,937 B2 | 11/2013 | Spudich et al. |
| 8,603,790 B2 | 12/2013 | Deisseroth et al. |
| 8,603,809 B2 | 12/2013 | Kruse |
| 8,617,876 B2 | 12/2013 | Farrar et al. |
| 8,629,256 B2 | 1/2014 | Looger et al. |
| 8,647,870 B2 | 2/2014 | Hegemann et al. |
| 8,716,447 B2 | 5/2014 | Deisseroth et al. |
| 2005/0064474 A1 | 3/2005 | Urnov et al. |
| 2006/0188987 A1 | 8/2006 | Guschin et al. |
| 2008/0131962 A1 | 6/2008 | Miller |
| 2011/0023144 A1 | 1/2011 | Weinstein et al. |
| 2012/0214236 A1 | 8/2012 | Bhatia et al. |
| 2012/0264623 A2 | 10/2012 | Fortunel et al. |
| 2013/0224756 A1 | 8/2013 | Cohen et al. |
| 2014/0135382 A1 | 5/2014 | Spudich et al. |
| 2014/0295413 A1 | 10/2014 | Cohen et al. |

FOREIGN PATENT DOCUMENTS

| | | |
|---|---|---|
| EP | 2028268 A1 | 2/2009 |
| WO | 2007/053526 A1 | 5/2007 |
| WO | 2009/047288 A1 | 4/2009 |
| WO | 2009/049181 A1 | 4/2009 |
| WO | 2010/027446 A2 | 3/2010 |
| WO | 2010/028089 A2 | 3/2010 |
| WO | 2012/027358 A1 | 3/2012 |
| WO | 2012/112737 A2 | 8/2012 |
| WO | 2013/078347 A2 | 5/2013 |

OTHER PUBLICATIONS

Dimitrov et al. PLoS ONE, 2007, 5, e440: 1-5.*
Vazin et al., 2014, Efficient derivation of cortical glutamatergic neurons from human pluripotent stem cells: a model system to study neurotoxicity in Alzheimer's disease, Neurobiol Dis 62:62-72.

(Continued)

*Primary Examiner* — Bin Shen
(74) *Attorney, Agent, or Firm* — Brown Rudnick LLP; Thomas C. Meyers

(57) ABSTRACT

The invention generally relates to optical methods for the diagnosis of neuronal condition by converting a cell from a patient into a neuron and optically evaluating action potentials of that cell in vitro. The cell is transformed with an optical reporter and exhibits an optical signature in response to neural stimulation. Using genome-editing, a control cell can be made that is isogenic but-for a known mutation and a control signature obtained from the control cell. Thus, methods of the invention reveal potential neurodegenerative effects of a mutation as manifested in a patient's genetic context. The optical signature of the cell, or the difference between the signature and the control signature, is correlated to a diagnosis of the neurodegenerative disease.

11 Claims, 21 Drawing Sheets

(56) References Cited

OTHER PUBLICATIONS

Hochbaum et al., Oct. 14, 2012, Optopatch—all-optical electrophysiology, Presentation Abstract, Neuroscience 2012 annual meeting, retrieved from the internet on Oct. 29, 2015, at: <<http://syntheticneurobiology.org/PDFs/12.10.hochbaum.pdf>>.

Cohen, 2013, All optical electrophysiology with microbial rhodopsins, Event Page for lecture on Feb. 4, 2013, retrieved from the internet on Oct. 29, 2015, at: <<http://www.fitzpatrick.duke.edu/events/all-optical-electrophysiology-microbial-rhodopsins-0>>.

Abdelfattah et al, 2014, Development of a red genetically encoded voltage indicator and its use with channelrhodopsin in all-optical electrophysiology, Biophys J 106(2)Supp 1:629a-630a.

Hochbaum, Sep. 1, 2014, Bringing bioelectricity to light: all-optical electrophysiology using microbial rhodopsins, PhD Thesis from Harvard University, Cambridge, MA.

Hochbaum et al., 2014, All-optical electrophysiology in mammalian neurons using engineered microbial rhodopsins, Nat Methods 11(8):825-833.

International Search Report and Written Opinion mailed Sep. 28, 2015, for International Patent Application No. PCT/US2015/026858 with International Filing Date Apr. 21, 2015 (20 pages).

Israel et al., 2012, Probing sporadic and familial Alzheimer's disease using induced pluripotent stem cells, Nature 482:216-220.

Inoue, 2015, Rational design of a high-affinity, fast, red calcium indicator R-CaMP2, Nat Meth 12(1):64-70.

Isalan, 2001, A rapid generally applicable method to engineer zinc fingers illustrated by targeting the HIV-1 promoter, Nat. Biotechnol 19:656-660.

Israel, 2012, Probing sporadic and familial Alzheimer's disease using induced pluripotent stem cells, Nature 482(7384):216-20.

Jackson, 2001, Analysis of lung tumor initiation and progression using conditional expression of oncogenic K-ras, Genes & Dev 15:3243-3248.

Joung, 2013, TALENs: a widely applicable technology for targeted genome editing, Nat Rev Mol Cell Bio 14:49-55.

Kim,, 2010, Zebrafish model of tuberous sclerosis complex reveals cell-autonomous and non-cell-autonomous functions of mutant tuberin, Dis Model Mech., 4(2):255-67.

Kiskinis, 2014, Pathways disrupted in human ALS motor neurons identified through genetic correction of mutant SOD1, Cell Stem Cell (epub).

Klapoetke, 2014, Independent optical excitation of distinct neural populations, Nat Meth 11:338-346.

Koch, 2011, Excitation-induced ataxin-3 aggregation in neurons from patients with Machado-Joseph disease, Nature 180(7378):543-546.

Kondo, 2013, Modeling Alzheimer's disease with iPSCs reveals stress phenotypes associated with intracellular Abeta and differential drug responsiveness, Cell Stem Cell 12(4):487-496.

Krey, 2013, Timothy syndrome is associated with activity-dependent dendritic retraction in rodent and human neurons, Nat Neurosci 16(2):201-9.

Ku, 2010, Friedreich's ataxia induced pluripotent stem cells model intergenerational GAA-TTC triplet repeat instability, Cell Stem Cell 7(5):631-7.

Kuo, 2003, Differentiation of monkey embryonic stem cells into neural lineages, Biology of Reproduction 68:1727-1735.

Lee, 2009, Modelling pathogenesis and treatment of familial dysautonomia using patient-specific iPSCs, Nature 461:402-406.

Lin, 2009, Characterization of engineered channelrhodopsin variants with improved properties and kinetics, Biophys J 96:1803-1814.

Liu, 2012, Signaling defects in iPSC-derived fragile X premutation neurons, Hum Mol Genet 21:3795-3805.

Liu, 2014, The more the better: modelling Dravet syndrom with induced pluripotent stem cell-derived neurons, Epil curr 14(1):33-34.

Lombardo, 2007, Gene editing in human stem cells using zinc finger nucleases and integrase-defective lentiviral vector delivery, Nat Biotechnol 25(11):1298-306.

Mahammad, 2013, Giant axonal neuropathy-associated gigaxonin mutations impair intermediate filament protein degredation, J Clin Invest 123(5):1964-75.

Makkerh, 1996, Comparative mutagenesis of nuclear localization signals reveals the importance of neutral and acidic amino acids, Current Biology 6:1025-1027.

Marchetto, 2010, A model for neural development and treatment of Rett syndrome using human induced pluripotent stem cells, Cell 143(4):527-39.

Maruyama, 2011, Detection of cells from calcium imaging data by non-negative matrix factorization, 21 Ann Conf. J Neur Net Soc.

Mattis, 2011, Principles for applying optogenetic tools derived from direct comparative analysis of microbial opsins, Nat Meth. 9:159-172.

Mazzulli, 2011, Gaucher disease glucocerebrosidase and a-synuclein form a bidirectional pathogenic loop in synucleinopathies, Cell 146(1):37-52.

Meikle, 2007, A mouse model of tuberous sclerosis: neuronal loss of Tsc1 causes dysplastic and ectopic neurons, reduced myelination, seizure activity, and limited survival, J Neurosci. 27(21):5546-58.

Meikle, 2006, Response of a neuronal model of tuberous sclerosis to mammalian target of rapamycin (mTOR) inhibitors: effects on mTORC1 and Akt signaling lead to improved survival and function, J Neurosci., 28(21):5422-32.

Moehle, 2007, Targeted gene addition into a specified location in the human genome using designed zinc finger nucleases PNAS 104:3055-3060.

Mukamel, 2009, Automated analysis of cellular signals from large-scale calcium imaging data, Neuron 63(6):747-760.

Muratore, 2014, The familial Alzheimer's disease APPV717I mutation alters APP processin and tau expression in PSC-derived neurons, Human Molecular Genetics, in press.

Musaro, 2010, State of the art and the dark side of amyotrophic lateral sclerosis, WJBC 1(5):62-68.

Nagel, 2005, Light activation of channelrhodopsin-2 in excitable cells of Caenorhabditis elegans triggers rapid behavioral responses, Curr. Biol. 15, 2279-2284.

Nihei, 2013, Enhanced aggregation of androgen receptor in induced pluripotent stem cell-derived neurons from spinal and bulbar muscular atrophy, J Biol Chem 288(12):8043-52.

Normand, 2013, Temporal and mosaic Tsc1 deletion in the developing thalamus disrupts thalamocortical circuitry, neural function, and behavior, Neuron, 5;78(5):895-909.

Pang, 2011, Induction of human neuronal cells by defined transcription factors, Nature 476:220-223.

Pasinelli, 2006, Molecular biology of amyotrophic lateral sclerosis: insights from genetics, Nat Rev Neurosci 7:710-723.

Peça, 2011, Shank3 mutant mice display autistic-like behaviours and striatal dysfunction, Nature 472 (7344): 437-42.

Piao, 2015, Combinatorial mutagenesis of the voltage-sensing domain enables the optical resolution of action potentials firing at 60 Hz by a genetically encoded fluorescent sensor of membrane potential, J Neurosci 35(1):372-385.

Popovic, 2011, The spatio-temporal characteristics of action potential initiation in layer 5 pyramidal neurons: a voltage imaging study, J. Physiol. 589:4167-4187.

Reinhardt, 2013, Genetic correction of a LRRK2 mutation in human iPSCs links parkinsonian neurodegeneration to ERK-dependent changes in gene expression, Cell Stem Cell 12(3):354-367.

Rothermel, 2013, Transgene expression in target-defined neuron populations mediated by retrograde infection ith adeno-associated viral vectors, J Neurosci 33(38):195-206.

Rotunno, 2013, An emerging role for misfolded wild-type SOD1 in sporadic ALS pathogenesis, Front Cell Neurosci 7:a253.

Saccon, 2013, Is SOD1 loss of function involved in amyotrophic lateral sclerosis?, Brain 136:2342-2358.

Sánchez-Danés, 2012, Disease-specific phenotypes in dopamine neurons from human iPS-based models of genetic and sporadic Parkinson's disease, EMBO Mol Med, 4: 380-395.

(56) References Cited

OTHER PUBLICATIONS

Sanders, 2013, LRRK2 mutations cause mitochondrial DNA damage in iPSC-derived neural cells from Parkinson's disease patients: reversal by gene correction. Neurobiol Dis 62:381-6.
Santiago, 2008, Targeted gene knockout in mammalian cells by using engineered zinc-finger nucleases, PNAS 105:5809-5814.
Sareen, 2012, Inhibition of apoptosis blocks human motor neuron cell death in a stem cell model of spinal muscular atrophy. PLoS One 7(6):e39113.
Sauer, 1988, Site-specific DNA recombination in mammalian cells by the Cre recombinase of bacteriophage P1, PNAS 85:5166-70.
Saunders, 2012, Novel recombinant adeno-associated viruses for Cre activated and inactivated transgene expression in neurons, Front Neural Circuits 6:47.
Seibler, 2011, Mitochondrial Parkin recruitment is impaired in neurons derived from mutant PINK1 induced pluripotent stem cells, J Neurosci 31(16):5970-6.
Shi, 2012. A human stem cell model of early Alzheimer's disease pathology in Down syndrome, Sci Transl Med 4(124):124ra129.
Siegel, 1997, A genetically encoded optical probe of membrane voltage. Neuron 19:735-741.
Son, 2011, Conversion of mouse and human fibroblasts into Functional spinal motor neurons, Cell Stem Cell 9:205-218.
Song, 2012, Neural differentiation of patient specific iPS cells as a novel approach to study the pathophysiology of multiple sclerosis, Stem Cell Res 8(2):259-73.
St-Pierre, 2014, High-fidelity optical reporting of neuronal electrical activity with an ultrafast fluorescent voltage sensor, Nat Neurosci 17(6):884.
Takahashi, 2006, Induction of pluripotent stem cells from mouse embryonic and adult fibroblast cultures by defined factors Cell 126:663-676.
Takahashi, 2007, Induction of pluripotent stem cells from adult human fibroblasts by defined factors, Cell 131:861-872.
Umov, 2005, Highly efficient endogenous human gene correction using designed zinc-finger nucleases, Nature 435(7042):646-51.
Vierbuchen, 2010, Direct conversion of fibroblasts to functional neurons by defined factors, Nature4 63:1035-1041.
Wah, 1998, Structure of FokI has implications for DNA cleavage, PNAS 95:10564-10569.
Wainger, 2014, Intrinsic membrane hyperexcitability of amyotrophic lateral sclerosis patient-derived motor neurons, Cell Reports 7(1):1-11.
Wang, 2011, Synaptic dysfunction and abnormal behaviors in mice lacking major isoforms of Shank3, Hum. Mol. Genet. 20 (15): 3093-108.
Wardill, 2013, A neuron-based screening platform for optimizing genetically-encoded calcium indicators, PLoS One 8(10):e77728.
Wernig, 2002, Tau EGFP embryonic stem cells: an efficient tool for neuronal lineage selection and transplantation. J Neuroscience Res 69:918-24.
Wlodarski,, 2008, Tuberin-heterozygous cell line TSC2ang1 as a model for tuberous sclerosis-associated skin lesions, Int J Mol Med. 21(2):245-50.
Wu, 2013, Improved orange and red Ca2+ indicators and photophysical considerations for optogenetic applications, ACS Chem Neurosci 4(6):963-972.
Xiao, 2013, Chromosomal deletions and inversions mediated by TALENS and CRISPR/Cas in zebrafish, Nucl Acids Res 1-11.
Yang, 2013, A small molecule screen in stem-cell-derived motor neurons identifies a kinase inhibitor as a candidate therapeutic for ALS, Cell Stem Cell 12(6):713-726.
Yizhar, 2011, Optogenetics in neural systems, Neuron 71(1):9-34.
Yoo, 2011, MicroRNA mediated conversion human fibroblasts to neurons, Nature 476:228-231.
Zhang, 2013, Rapid single-step induction of functional neurons from human pluripotent stem cells, Neuron 78(5):785-798.
Zhao, 2011, An expanded palette of genetically encoded Ca2+ indicators, Science 333(6051):1888-1891.
Zoghbi, 2012, Synaptic Dysfunction in Neurodevelopmental Disorders Associated with Autism and Intellectual Disabilities, Cold Spring Harb Perspect Biol. 4(3), J Neurol Sci. 217(1):47-54.
International Search Report and Written Opinion mailed Jul. 20, 2015, for International application No. PCT/US2015/026881, with International filing date Apr. 21, 2015 (12 pages).
Sapunar, 2012, Dorsal root ganglion—a potential new therapeutic target for neuropathic pain, J Pain Res 1:31-38.
Kralj, 2011, Optical recording of action potentials in mammalian neurons using microbial rhodopsins, Nat Meth 9(1):90-95.
Hochbaum, 2012, Optopatch—all-optical electrophysiology Abstract, Neuroscience Poster # 229.02 Abstract.
Hochbaum, 2014, Bringing bioelectricity to light: all-optical electrophysiology using microbial rhodopsins, Thesis, Harvard University (193 pages).
International Search Report and Written Opinion mailed Jul. 20, 2015, for International application No. PCT/US2015/026889 with International filing date Apr. 21, 2015 (13 pages).
Trounson, 2012, Human disease modeling with induced pluripotent stem cells, Curr Op Gen Dev 22(5):509-516.
Badger, 2014, Parkinson's disese in a dish—using stem cells as a molecular tool, Neuropharmacol 76:88-96.
Subramaniam, 1992, Aspartic acid 85 in bacteriorhodopsin functions both as proton acceptor and negative counterion to the Schiff base, J Biol Chem 267(36):25730-25733.
International Search Report and Written Opinion mailed Jan. 11, 2016, for International application No. PCT/US15/36181, with International filing date Jun. 17, 2015 (14 pages).
Beja et al., 2001, Proteorhodopsin phototrophy in the ocean, Nature 411:786-789.
Chaudhary, 2014, Measurement of optical action potentials and calcium transients in hIPSC-derived cardiomyocytes using the novel Optopatch fluorescent platform, poster presented in Oct. 2014.
Chen, 2013, Ultra-sensitive fluorescent proteins for imaging neuronal activity, Nature 499(7458):295-300.
Dana, 2016, Sensitive red protein calcium indicators for imaging neural activity, bioRxiv, first published online Feb. 29, 2016, and available at biorxiv.org/content/biorxiv/early/2016/02/29/041780.full.pdf.
Hou, 2014, Simultaneous mapping of membrane voltage and calcium in zebrafish heart in vivo reveals chamber-specific developmental transitions in ionic currents, Front Phys 5:344.
Kormann, 2011, Expression of therapeutic proteins after delivery of chemically modified mRNA in mice, Nat Biotech 29(2):154-7.
Melkonian, 1986, A light and electron microscopic study of *Scherffelia dubia,* a new member of the scaly green lagellates (Prasinophyceae). Nord. J. Bot. 6:235-256.
Molokanova, 2008, Bright, future of optical assays for ion channel drug discovery, Drug Discov Today 13:14-22.
Mordwinkin, 2013, A review of human pluripotent stem cell-derived cardiomyocytes for high-throughput drug discover, cardiotoxicity screening and publication standards, J Carcliovasc Trans Res 6(1):22-30.
Nakai, 2001, A high signal-to-noise Ca(2+) probe composed of a single fluorescent protein, Nat Biotech 19:137-141.
Neutze, 2002, Bacteriorhodopsin: a high-resolution structural view of vectorial proton transport, Biochimica et Biophysica Acta 1565:144-167.
Przybylo, 2010, Fluorescence techniques for determination of the membrane potentials in high throughput screening, J Fluoresc 20(6):1139-1157.
Sager, 2014, Rechanneling the cardiac proarrythmia safety paradigm: a meeting from the cardiac safety research consortium, Am Heart J 167(3):292-300.
Zangi, 2013, Modified mRNA directs the fate of heart progenitor cells and induces vascular regeneration after myocardial infarction, Nat Biotech 31:898-907.
Davis et al., 2012, Cardiomyocytes derived from pluripotent stem cells recapitulate electrophyisiological characteristics of an overlap syndrome of cardiac sodium channel disease, Circulation 125(25):3079-3091.

(56) References Cited

OTHER PUBLICATIONS

Higurashi et al., 2013, A human Dravet syndrome model from patient induced pluripotent stem cells, Mol Brain 6(1):19.
International Search Report and Written Opinion mailed Jul. 3, 2015, for International Patent Application No. PCT/US2015/026863 with International Filing Date Apr. 21, 2015 (10 pages).
Karlj et al., 2012, Optical recording of action potentials in mammalian neurons using a microbial rhodopsin, Nature Methods 9(1):90-95.
Alami, 2014, Microtubule-dependent transport of TDP-43 mRNA granules in neurons is impaired by ALS-causing mutations, Neuron 81(3):536-543.
Almeida, 2012, Induced pluripotent stem cell models of progranulin-deficient frontotemporal dementia uncover specific reversible neuronal defects, Cell Rep 2(4):789-798.
Almeida, 2013, Modeling key pathological features of frontotemporal dementia with C9ORF72 repeat expansion in PSC-derived human neurons, Acta Neuropathol 126(3):385-399.
Ambasudhan, 2011, Direct reprogramming of adult human fibroblasts to functional neurons under defined conditions, Cell Stem Cell 9:113-118.
Amoroso, 2013, Accelerated high-yield generation of limb-innervating motor neurons from human stem cells, J Neurosci 33(2):574-86.
An, 2012, Genetic correction of Huntington's disease phenotypes in induced pluripotent stems cells, Cell Stem Cell 11(2):253-263.
Ananiev, 2011, Isogenic pairs of wild type and mutant induced pluripotent stem cell (iPSC) lines from Rett syndrome patients as in vitro disease model, PLoS One 6(9):e25255.
Andrade, 2012, Evidence for premature aging due to oxidative stress in iPSCs from Cockayne syndrome, Hum Mol Genet 21:3825-3834.
Ataka, 2002, A genetically targetable fluorescent probe of channel gating with rapid kinetics, Biophys J 82:509-516.
Atasoy, 2009, A FLEX switch targets channelrhodopsin-2 to multiple cell types for imaging and long-range circuit mapping, J Neurosci 28(28):7025-7030.
Beerli, 2002, Engineering polydactyl zinc-finger transcription factors, Nat. Biotechnol, 20:135-141.
Belfort, 1997, Homing endonucleases: keeping the house in order, Nucleic Acids Res 25(17):3379-3388.
Bilican et al, 2012, Mutant induced pluripotent stem cell lines recapitulate aspects of TDP-43 proteinopathies and reveal cell-specific vulnerability, PNAS 109(15):5803-5808.
Blokhuis, 2013, Protein aggregation in amyotrophic lateral sclerosis, Acta Neuropathol 125:777-794.
Boulting, 2011, A functionally characterized test set of human induced pluripotent stem cells, Nat Biotech 29(3):279-286.
Bozdagi, 2010, Haploinsufficiency of the autism-associated Shank3 gene leads to deficits in synaptic function, social interaction, and social communication, Mol Autism 1 (1): 15.
Brennand, 2011, Modelling schizophrenia using human induced pluripotent stem cells, Nature 473(7346):221-225.
Cardin, 2010, Targeted optogenetic stimulation and recording of neurons in vivo using cell-type-specific expression of Channelrhodopsin-2, Nat Protoc 5(2):247-54.
Carlson, 2013, Circular permutated red fluorescent proteins and calcium ion indicators based on mCherry, Protein Eng Des Sel 26(12):763-772.
Chanda, 2005, A hybrid approach to measuring electrical activity in genetically specified neurons, Nat Neuroscience 8:1619-1626.
Chang, 2013, Genome editing with RNA-guided Cas9 nuclease in zebrafish embryos, Cell Res 23:465-472.
Chiang, 2011, Integration-free induced pluripotent stem cells derived from schizophrenia patients with a DISC1 mutation, Molecular Psych 16:358-360.
Chung, 2013, Identification and rescue of a-synuclein toxicity in Parkinson patient-derived neurons, Science 342(6161):983-7.
Cooper, 2012, Pharmacological rescue of mitochondrial deficits in iPSC-derived neural cells from patients with familial Parkinson's disease, Sci Transl Med 4(141):141ra90.
Corti, 2012, Genetic correction of human induced pluripotent stem cells from patients with spinal muscular atrophy, Sci Transl Med 4 (165):165ra162.
Davis, 2012, Cardiomyocytes derived from pluripotent stem cells recapitulate electrophyisiological characteristics of an overlap syndrome of cardiac sodium channel disease, Circulation 125(25):3079-3091.
Davis-Dusenbery, 2014, How to make spinal motor neurons, Development 141(3):491-501.
Denton, 2014, Loss of spastin function results in disease-specific axonal defects in human pluripotent stem cell-based models of hereditary spastic paraplegia, Stem Cells 32(2):414-23.
Diester, 2011, An optogenetic toolbox designed for primates, Nat Neurosci 14(3):387-97.
Dimos, 2008, Induced pluripotent stem cells generated from patients with ALS can be differentiated into motor neurons, Science 321(5893):1218-21.
Donnelly, 2013, RNA toxicity from the ALS/FTD C9orf72 expansion is mitigated by antisense intervention, Neuron 80(2):415-28.
Dottori, 2011, Neural development in human embryonic stem cells—applications of lentiviral vectors, J Cell Bio 112(8):1955-62.
Du, 2012, Role of mismatch repair enzymes in GAA.TTC triplet-repeat expansion in Friedreich ataxia induced pluripotent stem cells, J Biol Chem 287(35):29861-29872.
Ebert, 2009, Induced pluripotent stem cells from a spinal muscular atrophy patient, Nature 457(7227):277-80.
Egawa, 2012, Drug screening for ALS using patient-specific induced pluripotent stem cells; Sci Transl Med 4(145):145ra104.
Flytzanis, 2014, Archaerohodopsin variants with enhanced voltage-sensitive fluorescence in mammalian and Caenorhabditis elegans neurons, Nat Comm 5:4894.
Fong, 2013, Genetic correction of tauopathy phenotypes in neurons derived from human induced pluripotent stem cells, Stem Cell Reports 1(3):1-9.
Foust, 2010, Action potentials initiate in the axon initial segment and propagate through axon collaterals reliably in cerebellar Purkinje neurons, J. Neurosci 30:6891-6902.
Gong, 2013, Enhanced Archaerhodopsin fluorescent protein voltage indicators, PLoSOne 8(6):e66959.
Gong, 2014, Imaging neural spiking in brain tissue using FRET-opsin protein voltage sensors, Nat Comm 5:3674.
Gordon, 2013, Amyotrophic later sclerosis: an update for 2013 clinical features, pathophysiology, management, and therapeutic trials, Aging and Disease 4(5):295-310.
Govorunova, 2013, Characterization of a highly efficient blue-shifted channelrhodopsin from the marine alga *Platymonas subcordiformis,* J Biol Chem 288(41):29911-29922.
Graf, 2011, Historical origins of transdifferentiation and reprogramming, Cell Stem Cell 9:504-516.
Han, 2011,Constructing and deconstructing stem cell models of neurological disease, Neuron 70(4):626-44.
HD iPSC Consortium, 2012, Induced pluripotent stem cells from patients with Huntington's disease show CAG-repeat-expansion-associated phenotypes. Cell Stem Cell 11(2):264-278.
Hick, 2013, Neurons and cardiomyocytes derived from induced pluripotent stem cells as a model for mitochondrial defects in Friedreich's ataxia, Dis Model Mech 6(3):608-21.
Higurashi, 2013, A human Dravet syndrome model from patient induced pluripotent stem cells, Mol Brain 6(1):19.
Hochbaum, 2014, All-optical electrophysiology in mammalian neurons using engineered microbial rhodopsins, Nat Meth 11:825-833.
Hwang, 2013, Efficient genome editing in zebrafish using a CRISPR-Cas system, Nat. Biotechnol 31:227-229.

\* cited by examiner

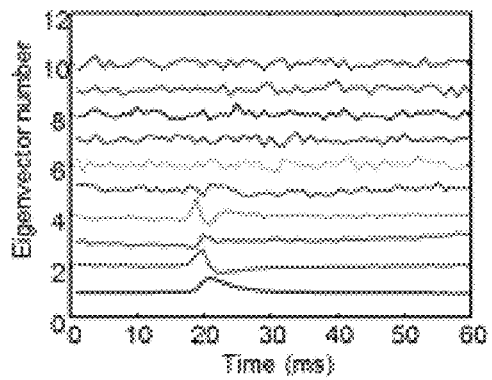
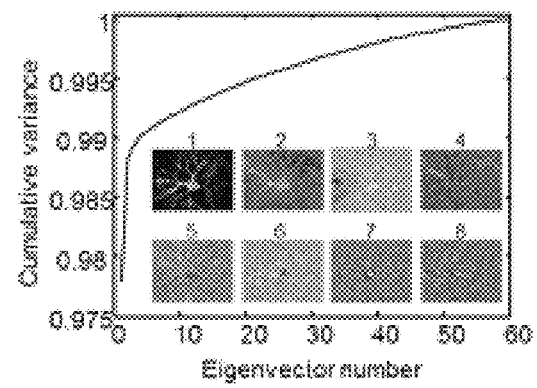
FIG. 12          FIG. 13
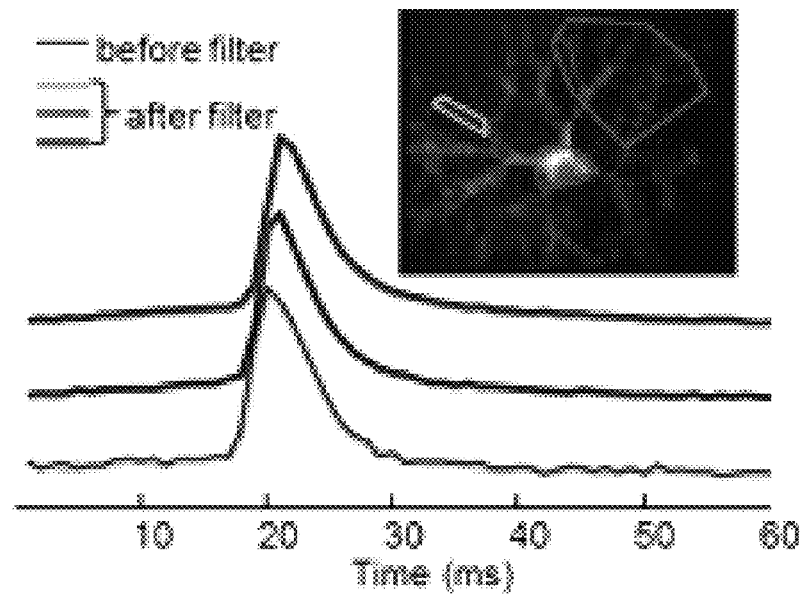
FIG. 14

DIAGNOSTIC METHODS FOR NEURAL DISORDERS

CROSS-REFERENCE TO RELATED APPLICATION

This application claims the benefit of, and priority to, U.S. Provisional Application Ser. No. 61/982,589, filed Apr. 22, 2014, the contents of which are incorporated by reference.

FIELD OF THE INVENTION

The invention relates to optical methods for the diagnosis of disease affecting neurons.

BACKGROUND

Neuronal diseases can be debilitating conditions that involve the malfunction, deterioration, or death of neurons. For example, when a person suffers from a neurodegenerative disease, his or her neurons deteriorate, which can initially manifest as forgetfulness, cognitive impairment, or loss of coordination. As the disease progresses, the person's condition can worsen considerably and he or she may become unable to walk and may suffer from severe dementia. Neurodegenerative diseases often present no outwardly visible symptoms until after they have caused significant harm to the nervous system.

Some neurodegenerative diseases are known to be associated with certain mutations or combinations of mutations. For example, variants of genes such as C9orf72, SOD1, TARDBP, FUS, UBQL2, ALS2, and SETX are known to be associated with amyotrophic lateral sclerosis or other neural disorders and the progression of the disease can vary depending on what combination of variants are present in a patient's genome. See Finsterer & Burgunder, 2014, Recent progress in the genetics of motor neuron disease, Eur J Med Genet, In press. As a consequence, simply by knowing that a person has one disease-associated mutation (e.g., C9orf72), a clinician cannot conclude that a disorder will manifest in that person. Furthermore, distinct underlying causes of a disease, for instance due to different mutations or due to differences in genetic background, may lead to outwardly similar sets of symptoms. Nonetheless, the treatment may need to be tailored to the underlying root-cause of the disease and to the particularities of each patient's genetic background.

Two factors conspire to prevent patient classification based solely upon genetic information: First, due to the vast number of possible disease-causing mutations, many such mutations occur at a very low level in the population. Additionally, there is a high level of genetic variation in the population that is not directly associated with disease. Thus from sequence alone, a clinician may not be able to determine which mutations are causative in a disease. Even if the mutation is found, the number of comparable cases may be so small that data on optimal treatment strategies is lacking.

SUMMARY

The invention provides methods for diagnosis of neuronal diseases by converting a cell from a patient into a neuron and optically evaluating action potentials of that cell in vitro. A somatic cell is obtained from a patient and converted into a motor neuron or other cell type of interest. The neural cell is transformed with a genetically encoded optical reporter, such as a transmembrane protein that fluoresces in response to the generation of an action potential. The cell, by the optical reporter, exhibits an optical signature in response to neural stimulation and that signature is observed and compared to a control signature, such as may be observed from a control cell with known properties. Differences between the observed signature and the control signature reveal properties of the patient cell and can be correlated to a diagnosis of a neurodegenerative disease. The invention uses methods of converting somatic cells such as fibroblasts to specific neural subtypes as well as transformation of cells with optogenetic actuators and reporters to allow for characterizing cells optically. Images captured by microscopy are analyzed digitally to identify optical signatures such as spike trains and associate the signatures with specific cells. Disease-affected and healthy patient cells can be distinguished according to their signature spike trains.

Using genome-editing, a practitioner can create patient-specific control cells that are isogenic but-for specific genetic variants that are suspected to be associated with disease. By these means, where a patient is known to have a certain mutation, methods of the invention can be used to see the consequences of that mutation within the genetic context of the patient's entire genome. The effects of not just a single identified variant, but of that variant in the context of all other alleles in the genome can be studied. Thus where a patient is known or suspected of having a disease-associated mutation, methods of the invention reveal potential neurodegenerative effects of that mutation as manifested in that patient's genetic context, giving a clinician a valuable tool for diagnosis or treating a disease.

The presented methods are minimally invasive and can be performed for patients of any age. Since the methods described here can be performed at an early age to diagnose a neurodegenerative disease, a disease can be identified well before it has advanced significantly and caused substantial damage, which may allow medical science a better chance to treat the disease.

Aspects of the invention provide a method of diagnosing a condition. The condition may be any disease or disorder that involves or affects neurons including developmental and genetic disorders and neurodegenerative diseases. A cell or cells are obtained from a person suspected of having the condition. For example, the cell may be obtained as a somatic cell (e.g., by dermal biopsy) from a patient. The cell is preferably converted into a neuron or a specific neural sub-type such as a motor neuron. The cells are caused to express an optical reporter of neural activity. The method includes observing a signature generated by the optical reporter in response to a stimulation of the cell and comparing the observed signature to a control signature. A difference between the observed signature and the control signature corresponds to a positive diagnosis of the condition. (In embodiments where the control signature is disease-type, a match between the observed signature and the control signature corresponds to a positive diagnosis of the condition.) The control signature may be obtained by obtaining a control cell suspected of not having the condition and observing a control signal generated by a control optical reporter in the control cell. In a preferred embodiment, the control cell is derived from the test cell or cells that are changed by genomic editing. Obtaining the control cell may include editing a genome from the subject such that the control cell and the cell are isogenic but for a mutation. Alternatively, the control cells may be derived from one or more individuals known not to have the condition nor to have genetic mutations associated with risk of the condition.

Any suitable condition may be diagnosed using the described methods. Methods of the invention are suited to diagnosing conditions such as genetic disorders, mental and psychiatric conditions, neurodevelopmental disorders and neurodegenerative diseases. Exemplary genetic disorders include Cockayne syndrome, Down Syndrome, Dravet syndrome, familial dysautonomia, Fragile X Syndrome, Friedreich's ataxia, Gaucher disease, giant axonal neuropathy, Charcot-Marie-Tooth disease, hereditary spastic paraplegias, Machado-Joseph disease (also called spinocerebellar ataxia type 3), Phelan-McDermid syndrome (PMDS), polyglutamine (polyQ)-encoding CAG repeats, a variety of ataxias including spinocerebellar ataxias, spinal muscular atrophy, and Timothy syndrome. Exemplary neurodegenerative diseases include Alzheimer's disease, frontotemporal lobar degeneration, Huntington's disease, multiple sclerosis, Parkinson's disease, spinal and bulbar muscular atrophy, and amyotrophic lateral sclerosis. Exemplary mental and psychiatric conditions include schizophrenia. Exemplary neurodevelopmental disorders include Rett syndrome. In one exemplary embodiment, the condition is amyotrophic lateral sclerosis (ALS). The patient may be known to have an ALS-associated mutation, such as a mutation in a gene such as SOD1, TARDBP, FUS, UBQL2, ALS2, or SETX. In certain embodiments, the subject has a mutation in a SOD1 gene, such as the SOD1A4V mutation.

In some embodiments, the cell is caused to express an optical actuator that initiates an action potential in response to optical stimulation. Stimulation of the cell may include illuminating the optical actuator.

Causing the cell to express the optical reporter may be done by transforming the cell with a vector bearing a genetically encoded fluorescent voltage reporter. The vector may also include a genetically encoded optical voltage actuator, such as a light-gated ion channel.

Observing the signal can include observing a cluster of different cells with a microscope and using a computer to isolate the signal generated by the optical reporter from a plurality of signals from the different cells. Methods of the invention may include using the computer to isolate the signal by performing an independent component analysis or other source-separation algorithm. The computer may be used to identify a spike train associated with the cell using standard spike-finding algorithms that apply steps of filtering the data and then applying a threshold. The computer may also be used to map propagation of electrical spikes within a single cell by means of an analytical algorithm such as a sub-Nyquist action potential timing algorithm. Methods may include observing and analyzing a difference between the observed signal and the expected signal. The difference may manifest as a decreased or increased probability of a voltage spike in response to the stimulation of the cell relative to a control, a change in the propagation of the signal within a cell, a change in the transformation of the signal upon synaptic transmission, or a change in the waveform of the action potential.

In certain aspects, the invention provides compound screening method that includes converting a somatic cell to an electrically active cell, incorporating into the electrically active cell an optical activator and an optical reporter of electrical activity, and exposing the cells to at least one compound. A signatures generated by the optical reporter in response to an optical stimulation of the cells is obtained and the method includes identifying an effect of the at least one compound on cellular phenotype based on the obtained signature. Preferably, the electrically active cell is a neuron, cardiomyocyte, or glial cell. "Electrically active cell" may be taken to refer to cells that transmit a signal or an action potential or participate in neural or cardiac function and include neurons, cardiomyocytes, and glia. A plurality of the electrically active cells may be exposed to a plurality of different compounds. Any effect may be identified such as an effect that represents cellular activity (action potential level, energy level, synaptic transmission).

In some embodiments, the somatic cell is obtained from a population of diseased cells. The method may include identifying the effectiveness of the compounds treating said diseased cells. Any disease may be modeled such as Cockayne syndrome, Down Syndrome, Dravet syndrome, familial dysautonomia, Fragile X Syndrome, Friedreich's ataxia, Gaucher disease, hereditary spastic paraplegias, Machado-Joseph disease, Phelan-McDermid syndrome (PMDS), polyglutamine (polyQ)-encoding CAG repeats, spinal muscular atrophy, Timothy syndrome, Alzheimer's disease, frontotemporal lobar degeneration, Huntington's disease, multiple sclerosis, Parkinson's disease, spinal and bulbar muscular atrophy, and amyotrophic lateral sclerosis.

The converting step may proceed by direct lineage conversion or conversion through an iPS intermediary.

The incorporating may include transforming the electrically active cells with a vector that includes a nucleic acid encoding the optical activator and the optical reporter of electrical activity. An optical activator may initiate an action potential in response to the optical stimulation. The cells may be stimulated by illumination. In certain embodiments, each of the electrically active cell is caused to express both the optical activator and the optical reporter of electrical activity.

The effect of the compound may be identified by comparing an electrical signature to a control signature obtained from a control cell. The method may include editing the genome of the electrically active cells to produce control cells such that the control cells and the electrically active cells are isogenic but for a mutation in the electrically active cells.

In some embodiments, the signature is obtained by observing a cluster of cells with a microscope and using a computer to isolate a signal generated by the optical reporter from among a plurality of signals from the cluster of cells. An image can be obtained of a plurality of clusters of cells using the microscope (i.e., all in a single image using a microscope of the invention). The computer isolates the signal by performing an independent component analysis and identifying a spike train produced by one single cell.

In certain aspects, the invention provides a method of treating a condition by obtaining a neuron derived from a somatic cell from a person having the condition, incorporating into the neuron an optical reporter of neural activity, and exposing the neuron to a candidate treatment compound. A signature generated by the optical reporter in response to a stimulation of the cell is used to observe an influence of the compound on a phenotype of the cell and—where the compound is observed to promote a normal-type phenotype—the compound is selected for treating the patient. The condition may be, for example, Cockayne syndrome, Down Syndrome, Dravet syndrome, familial dysautonomia, Fragile X Syndrome, Friedreich's ataxia, Gaucher disease, hereditary spastic paraplegias, Machado-Joseph disease, Phelan-McDermid syndrome (PMDS), polyglutamine (polyQ)-encoding CAG repeats, spinal muscular atrophy, Timothy syndrome, Alzheimer's disease, frontotemporal lobar degeneration, Huntington's disease, multiple sclerosis, Parkinson's disease, spinal and bulbar muscular atrophy, or amyotrophic lateral sclerosis. Methods include causing the cell to express an optical actuator that initiates an action potential in response to optical stimulation. The cell may be stimulated by illuminating the optical actuator. The cell may be obtained by obtaining a somatic cell from the subject and converting the somatic cell into an electrically active cell type. In certain embodiments, the somatic cell is converted to a neuron and may be converted to a specific neural sub-type. The condition may be neuronal disorder such as a neurodegenerative disease. Conversion may include direct lineage conversion or conversion through an iPS intermediary.

Observing the influence may include comparing the signature to a control signature obtained from a control cell, and the method further includes obtaining the control cell by editing a genome from the subject such that the control cell and the cell are isogenic but for a mutation. The neuron may be transformed with a vector bearing a genetically encoded fluorescent voltage reporter, a genetically encoded optical voltage actuator, or both.

To observe the signal, a cluster of cells may be observed with a microscope and a computer may isolate the signal generated by the optical reporter from a plurality of signals from the different cells. In some embodiments, the computer isolates the signal by performing an independent component analysis and identifying a spike train associated with the cell.

BRIEF DESCRIPTION OF THE DRAWINGS

FIG. 12 shows eigenvectors from a principal component analysis (PCA).

FIG. 13 shows a relation between cumulative variance and eigenvector number.

FIG. 14 gives a comparison of action potential waveforms.

DETAILED DESCRIPTION

The invention provides methods for the optical diagnosis of diseases affecting electrically active cells. Methods may be used to diagnose diseases affecting neurons or cardiomyocytes, for example. In some embodiments, methods of the invention are used to diagnoses a condition known to be associated with a genetic variant, or mutation.

Figure 1:
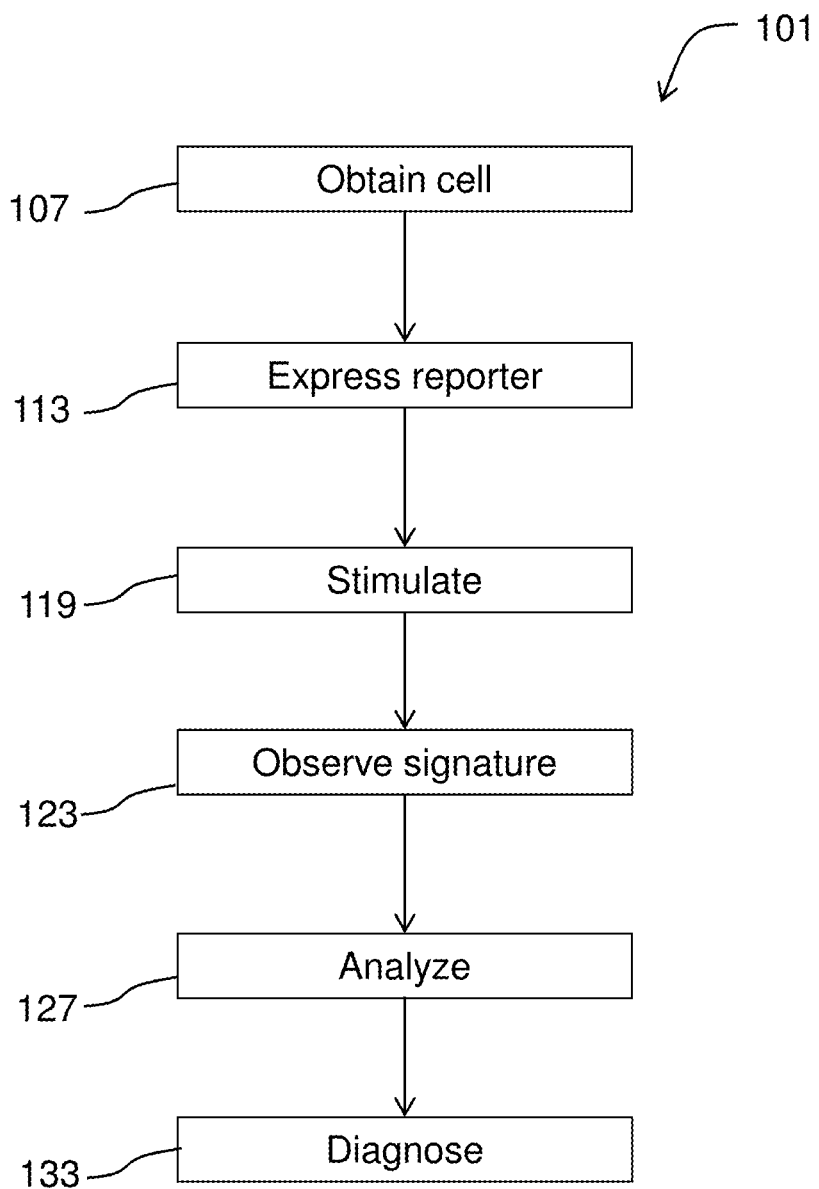
FIG. 1 diagrams a method for diagnosing a condition.

FIG. 1 diagrams a method 101 for diagnosing a condition according to embodiments of the invention. This may involve obtaining 107 a cell from a person suspected of having the condition. Genome editing techniques (e.g., use of transcription activator-like effector nucleases (TALENs), the CRISPR/Cas system, zinc finger domains) may be used to create a control cell that is isogenic but-for a variant of interest. The cell and the control are converted into an electrically excitable cell such as a neuron, astrocyte, or cardiomyocyte. The cell may be converted to a specific neural subtype (e.g., motor neuron). The cells are caused to express 113 an optical reporter of neural activity. For example, the cell may be transformed with a vector comprising an optogenetic reporter and the cell may also be caused to express an optogenetic actuator (aka activator) by transformation. Optionally, a control cell may be obtained, e.g., by taking another sample, by genome editing, or by other suitable techniques. Using microscopy and analytical methods described herein, the cells are observed and specifically, the cells' response to stimulation 119 (e.g., optical, synaptic, chemical, or electrical actuation) may be observed. A cell's characteristic signature such as a neural response as revealed by a spike train may be observed 123. The observed signature is compared to a control signature and a difference (or match) between the observed signature and the control signature corresponds to a positive diagnosis of the condition.

In one exemplary embodiment discussed herein, methods of the invention are used for optical differentiation of amyotrophic lateral sclerosis (ALS) arising from a monogenic mutation in the SOD1 gene (SOD1A4V).

1. Obtaining Cell(s)

Cells are obtained from a person suspected of having the condition. Any suitable condition such as a genetic disorder, mental or psychiatric condition, neurodegenerative disease or neurodevelopmental disorder, or cardiac condition may be diagnosed. Additionally, methods of the invention and the analytical pipelines described herein may be applied to any condition for which an electrophysiological phenotype has been developed. Exemplary genetic disorders suitable for analysis by a pipeline defined by methods of the invention include Cockayne syndrome, Down Syndrome, Dravet syndrome, familial dysautonomia, Fragile X Syndrome, Friedreich's ataxia, Gaucher disease, hereditary spastic paraplegias, Machado-Joseph disease (also called spinocerebellar ataxia type 3), Phelan-McDermid syndrome (PMDS), polyglutamine (polyQ)-encoding CAG repeats, giant axonal neuropathy, Charcot-Marie-Tooth disease, a variety of ataxias including spinocerebellar ataxias, spinal muscular atrophy, and Timothy syndrome. Exemplary neurodegenerative diseases include Alzheimer's disease, frontotemporal lobar degeneration, Huntington's disease, multiple sclerosis, Parkinson's disease, spinal and bulbar muscular atrophy, and amyotrophic lateral sclerosis. Exemplary mental and psychiatric conditions include schizophrenia. Exemplary neurodevelopmental disorders include Rett syndrome. While discussed here in terms of neuronal disorders, it will be appreciated that the methods described herein may be extended to the diagnosis of cardiac disorders and cells may be converted to cardiomyocytes. Exemplary cardiac conditions include long-QT syndromes, hypertrophic cardiomyopathies, and dilated cardiomyopathies. Moreover, electrophysiological phenotypes for a variety of conditions have been developed and reported in the literature.

Methods of the invention may include obtaining at least one neuron that has a genotype or phenotype associated with autism, such as a cell with a genome having a mutation in a gene linked to autism. Mutations in a number of genes have been linked to the development of autism, including SHANK3 (ProSAP2), CDH9, CDH10, MAPK3, SERT (SLC6A4), CACNA1G, GABRB3, GABRA4, EN2, the 3q25-27 locus, SLC25A12, HOXA1, HOXA2, PRKCB1, MECP2, UBE3A, NLGN3, MET, CNTNAP2, FOXP2, GSTP1, PRL, PRLR, and OXTR. Genes such as the SHANK3 have been studied in mouse models through N-terminal and PDZ domain knock-outs which resulted in phenotypes including impaired social interaction. Wang, et al., 2011, Synaptic dysfunction and abnormal behaviors in mice lacking major isoforms of Shank3, Hum. Mol. Genet. 20 (15): 3093-108; Bozdagi, et al., 2010, Haploinsufficiency of the autism-associated Shank3 gene leads to deficits in synaptic function, social interaction, and social communication, Mol Autism 1 (1): 15; Peça, et al., 2011, Shank3 mutant mice display autistic-like behaviours and striatal dysfunction, Nature 472 (7344): 437-42; each of which is incorporated by reference.

Dravet syndrome, also known as Severe Myoclonic Epilepsy of Infancy (SMEI), is a form of intractable epilepsy that begins in infancy and is often associated with mutations in the SCN1A gene or certain other genes such as SCN9A, SCN2B, PCDH19 or GABRG2. Dravet syndrome is discussed in Higurashi et al., 2013, A human Dravet syndrome model from patient induced pluripotent stem cells, Mol Brain 6:19, the contents of which are incorporated by reference. Other forms of epilepsy include generalized epilepsy with febrile seizures plus (GEFS+) which is thought to include Dravet syndrome, borderline severe myoclonic epilepsy of infancy (SMEB), and intractable epilepsy of childhood (IEC). Additional neurodevelopmental disorders associated with epilepsy which may be studied with the cells and methods of the invention include Angelman syndrome, Rolandic epilepsy, autosomal dominant nocturnal frontal lobe epilepsy, benign occipital epilepsies of childhood, Panalyiotopoulos syndrome, childhood absence epilepsy, epilepsy-intellectual disability in females, febrile lobe epilepsy, juvenile myoclonic epilepsy, Lennox-Gastaut syndrome, Ohtahara syndrome, photosensitive epilepsy, pyridoxine-dependent epilepsy, Unverricht-Lundborg disease, myoclonic epilepsy with ragged red fibers syndrome, Lafora disease, Rasmussen's encephalitis, ring chromosome 20 syndrome, temporal lobe epilepsy, tuberous sclerosis, and West syndrome. Additional genes associated with epilepsy which may be studied with the cells and methods of the invention include, WWOX, PRRT2, KCNC1, STX1B, CARS2, STXB1, KCNQ2, CDKL5, ARX, SPTAN, BRAT1, KCNQ3, SCN2A (NAV1.2), GABA receptors, NIPA2, CDKL5, PCDH19, and NAV1.1.

Tuberous sclerosis is a genetic disease that affects tumor suppressor proteins through mutations to the TSC1 or TSC2 genes. Tuberous sclerosis can result in tumor growth in the brain, kidneys, lungs, heart, skin, eyes and can negatively affect function of these organs. Neurological symptoms of tuberous sclerosis include autism, intellectual disabilities, developmental and behavioral problems, and seizures. People suffering from tuberous sclerosis face a range of prognoses based on the severity of their symptoms, ranging from mild skin abnormalities to severe mental disabilities and organ failure and death due to tumor growth. Tuberous sclerosis is discussed in Meikle, et al., 2007, A mouse model of tuberous sclerosis: neuronal loss of Tsc1 causes dysplastic and ectopic neurons, reduced myelination, seizure activity, and limited survival, J Neurosci. 27(21):5546-58; Meikle, et al., 2008, Response of a neuronal model of tuberous sclerosis to mammalian target of rapamycin (mTOR) inhibitors: effects on mTORC1 and Akt signaling lead to improved survival and function, J Neurosci., 28(21):5422-32; Normand, et al., 2013, Temporal and mosaic Tsc1 deletion in the developing thalamus disrupts thalamocortical circuitry, neural function, and behavior, Neuron, 5; 78(5):895-909; Kim, et al., 2010, Zebrafish model of tuberous sclerosis complex reveals cell-autonomous and non-cell-autonomous functions of mutant tuberin, Dis Model Mech., 4(2):255-67; and Wlodarski, et al., 2008, Tuberin-heterozygous cell line TSC2ang1 as a model for tuberous sclerosis-associated skin lesions, Int J Mol Med. 21(2):245-50; each incorporated in its entirety.

Parkinson's disease is a neurodegenerative disorder of the central nervous system that involves the death of dopamine-generating cells in the substantia nigra in the midbrain. Parkinson's disease is discussed in Cooper et al., 2012, Pharmacological rescue of mitochondrial deficits in iPSC-derived neural cells from patients with familial Parkinson's disease, Sci Transl Med 4(141):141ra90; Chung et al., 2013, Identification and rescue of α-synuclein toxicity in Parkinson patient-derived neurons, Science 342(6161):983-7; Seibler et al., 2011, Mitochondrial Parkin recruitment is impaired in neurons derived from mutant PINK1 induced pluripotent stem cells, J Neurosci 31(16):5970-6; Sanchez-Danes et al., 2012, Disease-specific phenotypes in dopamine neurons from human iPS-based models of genetic and sporadic Parkinson's disease, EMBO Mol Med 4(5):380-395; Sanders et al., 2013, LRRK2 mutations cause mitochondrial DNA damage in iPSC-derived neural cells from Parkinson's disease patients: reversal by gene correction. Neurobiol Dis 62:381-6; and Reinhardt et al., 2013, Genetic correction of a LRRK2 mutation in human iPSCs links parkinsonian neurodegeneration to ERK-dependent changes in gene expression, Cell Stem Cell 12(3):354-367; LRRK2 mutant iPSC-derived DA neurons demonstrate increased susceptibility to oxidative stress, the contents of each of which are incorporated by reference Cockayne syndrome is a genetic disorder caused by mutations in the ERCC6 and ERCC8 genes and characterized by growth failure, impaired development of the nervous system, photosensitivity, and premature aging. Cockayne syndrome is discussed in Andrade et al., 2012, Evidence for premature aging due to oxidative stress in iPSCs from Cockayne syndrome, Hum Mol Genet 21:3825-3834, the contents of which are incorporated by reference.

Down syndrome is a genetic disorder caused by the presence of all or part of a third copy of chromosome 21 and associated with delayed growth, characteristic facial features, and intellectual disability. Down Syndrome is discussed in Shi et al., 2012, A human stem cell model of early Alzheimer's disease pathology in Down syndrome, Sci Transl Med 4(124):124ra129, the contents of which are incorporated by reference.

Dravet syndrome, also known as Severe Myoclonic Epilepsy of Infancy (SMEI), is a form of intractable epilepsy that begins in infancy and is often associated with mutations in the SCN1A gene or certain other genes such as SCN9A, SCN2B, PCDH19 or GABRG2. Dravet syndrome is discussed in Higurashi et al., 2013, A human Dravet syndrome model from patient induced pluripotent stem cells, Mol Brain 6:19, the contents of which are incorporated by reference.

Familial dysautonomia is a genetic disorder of the autonomic nervous system caused by mutations in the IKBKAP gene and that affects the development and survival of sensory, sympathetic and some parasympathetic neurons in the autonomic and sensory nervous system resulting in variable symptoms including: insensitivity to pain, inability to produce tears, poor growth, and labile blood pressure. Familial dysautonomia is discussed in Lee et al., 2009, Modelling pathogenesis and treatment of familial dysautonomia using patient-specific iPSCs, Nature 461:402-406, the contents of which are incorporated by reference.

Fragile X syndrome is a genetic condition caused by mutations in the FMR1 gene and that causes a range of developmental problems including learning disabilities and cognitive impairment. Fragile X Syndrome is discussed in Liu et al., 2012, Signaling defects in iPSC-derived fragile X premutation neurons, Hum Mol Genet 21:3795-3805, the contents of which are incorporated by reference.

Friedreich ataxia is an autosomal recessive ataxia resulting from a mutation of a gene locus on chromosome 9. The ataxia of Friedreich's ataxia results from the degeneration of nerve tissue in the spinal cord, in particular sensory neurons essential (through connections with the cerebellum) for directing muscle movement of the arms and legs. The spinal cord becomes thinner and nerve cells lose some of their myelin sheath. Friedreich's ataxia is discussed in Ku et al., 2010, Friedreich's ataxia induced pluripotent stem cells model intergenerational GAA.TTC triplet repeat instability, Cell Stem Cell 7(5):631-7; Du et al., 2012, Role of mismatch repair enzymes in GAA.TTC triplet-repeat expansion in Friedreich ataxia induced pluripotent stem cells, J Biol Chem 287(35):29861-29872; and Hick et al., 2013, Neurons and cardiomyocytes derived from induced pluripotent stem cells as a model for mitochondrial defects in Friedreich's ataxia, Dis Model Mech 6(3):608-21, the contents of each of which are incorporated by reference.

Gaucher's disease is a genetic disease caused by a recessive mutation in a gene located on chromosome 1 and in which lipids accumulate in the body. Gaucher disease is discussed in Mazzulli et al., 2011, Gaucher disease glucocerebrosidase and α-synuclein form a bidirectional pathogenic loop in synucleinopathies, Cell 146(1):37-52, the contents of which are incorporated by reference.

Hereditary Spastic Paraplegia (HSP)—also called Familial Spastic Paraplegias, French Settlement Disease, or Strumpell-Lorrain disease—refers to a group of inherited diseases characterized by axonal degeneration and dysfunction resulting in stiffness and contraction (spasticity) in the lower limbs. Hereditary spastic paraplegias is discussed in Denton et al., 2014, Loss of spastin function results in disease-specific axonal defects in human pluripotent stem cell-based models of hereditary spastic paraplegia, Stem Cells 32(2):414-23, the contents of which are incorporated by reference.

Spinocerebellar ataxia type 3 (SCA3), also known as Machado-Joseph disease, is a neurodegenerative disease, an autosomal dominantly inherited ataxia characterized by the slow degeneration of the hindbrain. Machado-Joseph disease (also called spinocerebellar ataxia type 3) is discussed in Koch et al., 2011, Excitation-induced ataxin-3 aggregation in neurons from patients with Machado-Joseph disease, Nature 480(7378):543-546, the contents of which are incorporated by reference.

Phelan-McDermid Syndrome (PMDS) is a progressive neurodevelopmental disorder resulting from mutations in or deletions of the neural protein, Shank3 and characterized by developmental delay, impaired speech, and autism. Phelan-McDermid syndrome (PMDS) is discussed in Shcheglovitov et al., 2013, SHANK3 and IGF1 restore synaptic deficits in neurons from 22q13 deletion syndrome patients, Nature 503(7475):267-71, the contents of which are incorporated by reference.

Trinucleotide repeat disorders are characterized by polyglutamine (polyQ)-encoding CAG repeats. Trinucleotide repeat disorders refer to a set of genetic disorders caused by trinucleotide repeat expansion, which disorders include dentatorubropallidoluysian atrophy, Huntington's disease, spinobulbar muscular atrophy, Spinocerebellar ataxia Type 1, Spinocerebellar ataxia Type 2, Spinocerebellar ataxia Type 3 or Machado-Joseph disease, Spinocerebellar ataxia Type 6, Spinocerebellar ataxia Type 7, and Spinocerebellar ataxia Type 17, as well as a variety of other ataxias. Trinucleotide repeat disorders are discussed in HD iPSC Consortium, 2012, Induced pluripotent stem cells from patients with Huntington's disease show CAG-repeat-expansion-associated phenotypes. Cell Stem Cell 11(2):264-278, the contents of which are incorporated by reference.

Giant axonal neuropathy is a neurological disorder that causes disorganization of neurofilaments, which form a structural framework to define the shape and size of neurons. Giant axonal neuropathy results from mutations in the GAN gene, which codes for the protein gigaxonin. See Mahammad et al., 2013, Giant axonal neuropathy-associated gigaxonin mutations impair intermediate filament protein degredation, J Clin Invest 123(5):1964-75.

Charcot Marie Tooth disease, also known as hereditary motor and sensory neuropathy (HMSN) and peroneal muscular atrophy (PMA), refers to several inherited disorders of the peripheral nervous system characterized by progressive loss of muscle and sensation. See, e.g., Harel and Lupski, 2014, Charcot Marie Tooth disease and pathways to molecular based therapies, Clin Genet DOI: 10.1111/cge.12393.

Spinal muscular atrophy (SMA) is genetic disease caused by mutations in the SMN1 gene, which encodes the survival of motor neuron protein (SMN), the diminished abundance of which neurons results in death of neuronal cells in the spinal cord and system-wide atrophy. Spinal muscular atrophy is discussed in Ebert et al., 2009, Induced pluripotent stem cells from a spinal muscular atrophy patient, Nature 457(7227):277-80; Sareen et al., 2012, Inhibition of apoptosis blocks human motor neuron cell death in a stem cell model of spinal muscular atrophy. PLoS One 7(6):e39113; and Corti et al., 2012, Genetic correction of human induced pluripotent stem cells from patients with spinal muscular atrophy, Sci Transl Med 4 (165):165ra162, the contents of each of which are incorporated by reference.

Timothy syndrome is a genetic disorder arising from a mutation in the Ca(v)1.2 Calcium Channel gene called CACNA1C and characterized by a spectrum of problems that include an abnormally prolonged cardiac "repolarization" time (long QT interval) and other neurological and developmental defects, including heart QT-prolongation, heart arrhythmias, structural heart defects, syndactyly and autism spectrum disorders. Timothy syndrome is discussed in Krey et al., 2013, Timothy syndrome is associated with activity-dependent dendritic retraction in rodent and human neurons, Nat Neurosci 16(2):201-9, the contents of which are incorporated by reference.

Mental and psychiatric disorders such as schizophrenia and autism may involve cellular and molecular defects amenable to study via stem cell models and may be caused by or associated with certain genetic components that can be isolated using methods herein. Schizophrenia is discussed in Brennand et al., 2011, Modelling schizophrenia using human induced pluripotent stem cells, Nature 473(7346):221-225; and Chiang et al., 2011, Integration-free induced pluripotent stem cells derived from schizophrenia patients with a DISC1 mutation, Molecular Psych 16:358-360, the contents of each of which are incorporated by reference.

Alzheimer's disease is a neurodegenerative disease of uncertain cause (although mutations in certain genes have been linked to the disorder) and is one of the most common forms of dementia. Alzheimer's disease is discussed in Israel et al., 2012, Probing sporadic and familial Alzheimer's disease using induced pluripotent stem cells, Nature 482(7384):216-20; Muratore et al., 2014, The familial Alzheimer's disease APPV717I mutation alters APP processing and tau expression in iPSC-derived neurons, Human Molecular Genetics, in press; Kondo et al., 2013, Modeling Alzheimer's disease with iPSCs reveals stress phenotypes associated with intracellular Abeta and differential drug responsiveness, Cell Stem Cell 12(4):487-496; and Shi et al., 2012, A human stem cell model of early Alzheimer's disease pathology in Down syndrome, Sci Transl Med 4(124):124ra129, the contents of each of which are incorporated by reference.

Frontotemporal lobar degeneration (FTLD) is the name for a group of clinically, pathologically and genetically heterogeneous disorders including frontotemporal dementia (which subdivides to include behavioral-variant frontotemporal dementia (bvFTLD); semantic dementia (SD); and progressive nonfluent aphasia (PNFA)) associated with atrophy in the frontal lobe and temporal lobe of the brain. Frontotemporal lobar degeneration is discussed in Almeida et al, 2013, Modeling key pathological features of frontotemporal dementia with C9ORF72 repeat expansion in iPSC-derived human neurons, Acta Neuropathol 126(3):385-399; Almeida et al., 2012, Induced pluripotent stem cell models of progranulin-deficient frontotemporal dementia uncover specific reversible neuronal defects, Cell Rep 2(4):789-798; and in Fong et al., 2013, Genetic correction of tauopathy phenotypes in neurons derived from human induced pluripotent stem cells, Stem Cell Reports 1(3):1-9, the contents of each of which are incorporated by reference.

Huntington's disease is an inherited disease that causes the progressive degeneration of nerve cells in the brain and is caused by an autosomal dominant mutation in either of an individual's two copies of a gene called Huntingtin (HTT) located on the short arm of chromosome 4. Huntington's disease is discussed in HD iPSC Consortium, 2012, Induced pluripotent stem cells from patients with Huntington's disease show CAG-repeat-expansion-associated phenotypes. Cell Stem Cell 11(2):264-278; An et al., 2012, Genetic correction of Huntington's disease phenotypes in induced pluripotent stem cells, Cell Stem Cell 11(2):253-263; and Camnasio et al., 2012, The first reported generation of several induced pluripotent stem cell lines from homozygous and heterozygous Huntington's disease patients demonstrates mutation related enhanced lysosomal activity, Neurobiol Dis 46(1):41-51, the contents of each of which are incorporated by reference.

Multiple sclerosis is a neurodegenerative disease in which the insulating covers of nerve cells in the brain and spinal cord are damaged. Multiple sclerosis is discussed in Song et al., 2012, Neural differentiation of patient specific iPS cells as a novel approach to study the pathophysiology of multiple sclerosis, Stem Cell Res 8(2):259-73, the contents of which are incorporated by reference.

Parkinson's disease is a neurodegenerative disorder of the central nervous system that involves the death of dopamine-generating cells in the substantia nigra in the midbrain. Parkinson's disease is discussed in Cooper et al., 2012, Pharmacological rescue of mitochondrial deficits in iPSC-derived neural cells from patients with familial Parkinson's disease, Sci Transl Med 4(141):141ra90; Chung et al., 2013, Identification and rescue of α-synuclein toxicity in Parkinson patient-derived neurons, Science 342(6161):983-7; Seibler et al., 2011, Mitochondrial Parkin recruitment is impaired in neurons derived from mutant PINK1 induced pluripotent stem cells, J Neurosci 31(16):5970-6; Sanchez-Danes et al., 2012, Disease-specific phenotypes in dopamine neurons from human iPS-based models of genetic and sporadic Parkinson's disease, EMBO Mol Med 4(5):380-395; Sanders et al., 2013, LRRK2 mutations cause mitochondrial DNA damage in iPSC-derived neural cells from Parkinson's disease patients: reversal by gene correction. Neurobiol Dis 62:381-6; and Reinhardt et al., 2013, Genetic correction of a LRRK2 mutation in human iPSCs links parkinsonian neurodegeneration to ERK-dependent changes in gene expression, Cell Stem Cell 12(3):354-367; LRRK2 mutant iPSC-derived DA neurons demonstrate increased susceptibility to oxidative stress, the contents of each of which are incorporated by reference.

Spinal and bulbar muscular atrophy (SBMA), also known as spinobulbar muscular atrophy, bulbo-spinal atrophy, X-linked bulbospinal neuropathy (XBSN), X-linked spinal muscular atrophy type 1 (SMAX1), and Kennedy's disease (KD)—is a neurodegenerative disease associated with mutation of the androgen receptor (AR) gene and that results in muscle cramps and progressive weakness due to degeneration of motor neurons in the brain stem and spinal cord. Spinal and bulbar muscular atrophy is discussed in Nihei et al., 2013, Enhanced aggregation of androgen receptor in induced pluripotent stem cell-derived neurons from spinal and bulbar muscular atrophy, J Biol Chem 288(12):8043-52, the contents of which are incorporated by reference.

Rett syndrome is a neurodevelopmental disorder generally caused by a mutation in the methyl CpG binding protein 2, or MECP2, gene and which is characterized by normal early growth and development followed by a slowing of development, loss of purposeful use of the hands, distinctive hand movements, slowed brain and head growth, problems with walking, seizures, and intellectual disability. Rett syndrome is discussed in Marchetto et al., 2010, A model for neural development and treatment of Rett syndrome using human induced pluripotent stem cells, Cell, 143(4):527-39 and in Ananiev et al., 2011, Isogenic pairs of wild type and mutant induced pluripotent stem cell (iPSC) lines from Rett syndrome patients as in vitro disease model, PLoS One 6(9):e25255, the contents of each of which are incorporated by reference.

In one illustrative example, the condition is amyotrophic lateral sclerosis. Amyotrophic lateral sclerosis (ALS), often referred to as "Lou Gehrig's Disease," is a neurodegenerative disease associated with the progressive degeneration and death of the motor neurons and a resultant loss of muscle control or paralysis. Amyotrophic lateral sclerosis is discussed in Kiskinis et al., 2014, Pathways disrupted in human ALS motor neurons identified through genetic correction of mutant SOD1, Cell Stem Cell (epub); Wainger et al., 2014, Intrinsic membrane hyperexcitability of amyotrophic lateral sclerosis patient-derived motor neurons, Cell Reports 7(1): 1-11; Donnelly et al., 2013, RNA toxicity from the ALS/FTD C9orf72 expansion is mitigated by antisense intervention, Neuron 80(2):415-28; Alami, 2014, Microtubule-dependent transport of TDP-43 mRNA granules in neurons is impaired by ALS-causing mutations, Neuron 81(3):536-543; Donnelly et al., 2013, RNA toxicity from the ALS/FTD C9ORF72 expansion is mitigated by antisense intervention, Neuron 80(2):415-428; Bilican et al, 2012, Mutant induced pluripotent stem cell lines recapitulate aspects of TDP-43 proteinopathies and reveal cell-specific vulnerability, PNAS 109(15):5803-5808; Egawa et al., 2012, Drug screening for ALS using patient-specific induced pluripotent stem cells, Sci Transl Med 4(145):145ra104; and in Yang et al., 2013, A small molecule screen in stem-cell-derived motor neurons identifies a kinase inhibitor as a candidate therapeutic for ALS, Cell Stem Cell 12(6):713-726, the contents of each of which are incorporated by reference.

In one illustrative example, fibroblasts may be taken from a patient known or suspected to have a mutation such as a mutation in SOD1. Any suitable cell may be obtained and any suitable method of obtaining a sample may be used. In some embodiments, a dermal biopsy is performed to obtain dermal fibroblasts. The patient's skin may be cleaned and given an injection of local anesthetic. Once the skin is completely anesthetized, a sterile 3 mm punch is used. The clinician may apply pressure and use a "drilling" motion until the punch has pierced the epidermis. The punch will core a 3 mm cylinder of skin. The clinician may use forceps to lift the dermis of the cored skin and a scalpel to cut the core free. The biopsy sample may be transferred to a sterile BME fibroblast medium after optional washing with PBS and evaporation of the PBS. The biopsy site on the patient is dressed (e.g., with an adhesive bandage). Suitable methods and devices for obtaining the cells are discussed in U.S. Pat. Nos. 8,603,809; 8,403,160; 5,591,444; U.S. Pub. 2012/0264623; and U.S. Pub. 2012/0214236, the contents of each of which are incorporated by reference. Any tissue culture technique that is suitable for the obtaining and propagating biopsy specimens may be used such as those discussed in Freshney, Ed., 1986, Animal Cell Culture: A Practical Approach, IRL Press, Oxford England; and Freshney, Ed., 1987, Culture of Animal Cells: A Manual of Basic Techniques, Alan R. Liss & Co., New York, both incorporated by reference.

2. Converting Cell(s) into Neurons, Cardiomyocytes, or Specific Neural Sub-Types Obtained cells may be converted into any electrically excitable cells such as neurons, specific neuronal subtypes, astrocytes or other glia, cardiomyocytes, or immune cells. Additionally, cells may be converted and grown into co-cultures of multiple cell types (e.g. neurons+glia, neurons+cardiomyocytes, neurons+immune cells).

Figure 2:
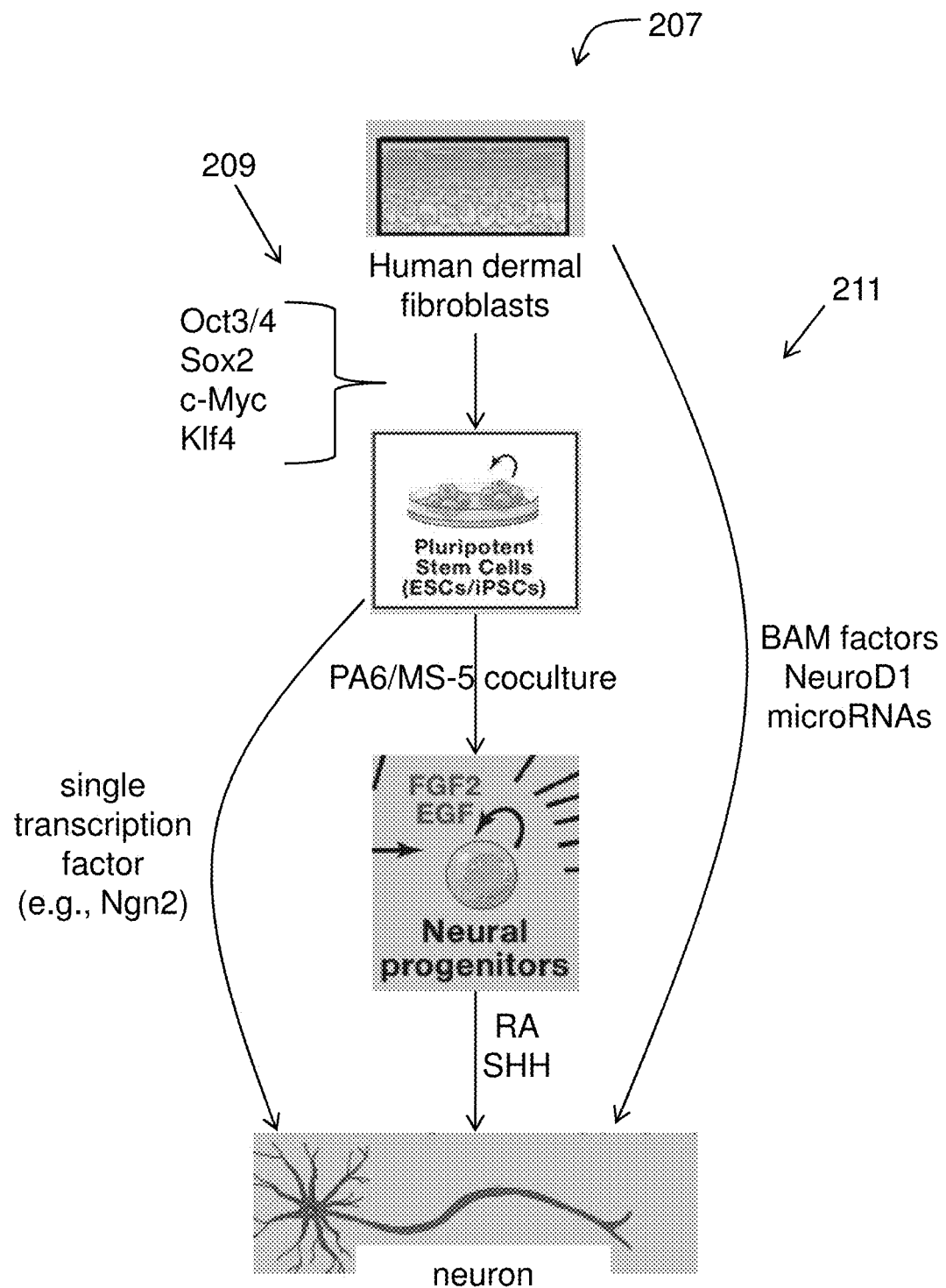
FIG. 2 illustrates exemplary pathways for converting cells into specific neural subtypes.

FIG. 2 illustrates exemplary pathways for converting cells into specific neural subtypes. A cell may be converted to a specific neural subtype (e.g., motor neuron). Suitable methods and pathways for the conversion of cells include pathway 209, conversion from somatic cells to induced pluripotent stem cells (iPSCs) and conversion of iPSCs to specific cell types, or pathways 211 direct conversion of cells in specific cell types.

2a. Conversion of Cells to iPSs and Conversion of iPSs to Specific Cell Types

Following pathways 209, somatic cells may be reprogrammed into induced pluripotent stem cells (iPSCs) using known methods such as the use of defined transcription factors. The iPSCs are characterized by their ability to proliferate indefinitely in culture while preserving their developmental potential to differentiate into derivatives of all three embryonic germ layers. In certain embodiments, fibroblasts are converted to iPSC by methods such as those discussed in Takahashi and Yamanaka, 2006, Induction of pluripotent stem cells from mouse embryonic and adult fibroblast cultures by defined factors Cell 126:663-676.; and Takahashi, et al., 2007, Induction of pluripotent stem cells from adult human fibroblasts by defined factors, Cell 131: 861-872.

Induction of pluripotent stem cells from adult fibroblasts can be done by methods that include introducing four factors, Oct3/4, Sox2, c-Myc, and Klf4, under ES cell culture conditions. Human dermal fibroblasts (HDF) are obtained. A retroviruses containing human Oct3/4, Sox2, Klf4, and c-Myc is introduced into the HDF. Six days after transduction, the cells are harvested by trypsinization and plated onto mitomycin C-treated SNL feeder cells. See, e.g., McMahon and Bradley, 1990, Cell 62:1073-1085. About one day later, the medium (DMEM containing 10% FBS) is replaced with a primate ES cell culture medium supplemented with 4 ng/mL basic fibroblast growth factor (bFGF). See Takahashi, et al., 2007, Cell 131:861. Later, hES cell-like colonies are picked and mechanically disaggregated into small clumps without enzymatic digestion. Each cell should exhibit morphology similar to that of human ES cells, characterized by large nuclei and scant cytoplasm. The cells after transduction of HDF are human iPS cells. DNA fingerprinting, sequencing, or other such assays may be performed to verify that the iPS cell lines are genetically matched to the donor.

These iPS cells can then be differentiated into specific neuronal subtypes. Pluripotent cells such as iPS cells are by definition capable of differentiating into cell types characteristic of different embryonic germ layers. A property of both embryonic stem cells human iPS cells is their ability, when plated in suspension culture, to form embryoid bodies (EBs). EBs formed from iPS cells are treated with two small molecules: an agonist of the sonic hedgehog (SHH) signaling pathway and retinoic acid (RA). For more detail, see the methods described in Dimos et al., 2008, Induced pluripotent stem cells generated from patients with ALS can be differentiated into motor neurons, Science 321(5893):1218-21; Amoroso et al., 2013, Accelerated high-yield generation of limb-innervating motor neurons from human stem cells, J Neurosci 33(2):574-86; and Boulting et al., 2011, A functionally characterized test set of human induced pluripotent stem cells, Nat Biotech 29(3):279-286.

Aspects of the invention provide cellular disease models in which stem cells may be converted into functional neurons by forced expression of a single transcription factor and then also caused to express optogenetic reporters or actuators of neural activity. A transcription factor such as neurogenin-2 (NgN2) or NeurD1 introduced into a pluripotent stem cell by transfection is expressed, causing the cell to differentiate into a neuron. Additionally or separately an optogenetic construct that includes an optical reporter of intracellular calcium as well as an optical actuator or reporter of membrane potential is expressed.

In some embodiments, conversion includes causing a stem cell to express a single transcription factor. Overexpressing a single transcription factor such as neurogenin-2 (Ngn2) or NeuroD1 alone rapidly converts ES and iPS cells into neuronal cells. See Zhang et al., 2013, Rapid single-step induction of functional neurons from human pluripotent stem cells, Neuron 78(5):785-798. The transcription factor may be introduced by lentiviral infection (discussed in greater detail below). As reported in Zhang 2013 a puromycin resistance gene may be co-expressed with Ngn2 for selection. ES or iPS cells are plated on day −2, infected with lentiviruses on day −1, and Ngn2 expression is induced on day 0. A 24 hr puromycin selection period is started on day 1, and mouse glia (primarily astrocytes) are added on day 2 to enhance synapse formation. Forced Ngn2 expression converts ES and iPS cells into neuron-like cells in less than one week, and produces an apparently mature neuronal morphology in less than two weeks, as reported in Zhang 2013.

When the differentiated EBs are allowed to adhere to a laminin-coated surface, neuron-like outgrowths are observed and a result is differentiation into specific neuronal subtypes. Additional relevant discussion may be found in Davis-Dusenbery et al., 2014, How to make spinal motor neurons, Development 141(3):491-501; Sandoe and Eggan, 2013, Opportunities and challenges of pluripotent stem cell neurodegenerative disease models, Nat Neuroscience 16(7): 780-9; and Han et al., 2011, Constructing and deconstructing stem cell models of neurological disease, Neuron 70(4):626-44.

2b. Direct Conversion of Cells in Specific Cell Types

By pathway 211, human somatic cells are obtained and direct lineage conversion of the somatic cells into motor neurons may be performed. Conversion may include the use of lineage-specific transcription factors to induce the conversion of specific cell types from unrelated somatic cells. See, e.g., Davis-Dusenbery et al., 2014, How to make spinal motor neurons, Development 141:491; Graf, 2011, Historical origins of transdifferentiation and reprogramming, Cell Stem Cell 9:504-516. It has been shown that a set of neural lineage-specific transcription factors, or BAM factors, causes the conversion of fibroblasts into induced neuronal (iN) cells. Vierbuchen 2010 Nature 463:1035. MicroRNAs and additional pro-neuronal factors, including NeuroD1, may cooperate with or replace the BAM factors during conversion of human fibroblasts into neurons. See, for example, Ambasudhan et al., 2011, Direct reprogramming of adult human fibroblasts to functional neurons under defined conditions, Cell Stem Cell 9:113-118; Pang et al., 2011, Induction of human neuronal cells by defined transcription factors, Nature 476:220-223; also see Yoo et al., 2011, MicroRNA mediated conversion of human fibroblasts to neurons, Nature 476:228-231.

2c. Maintenance of Differentiated Cells

Differentiated cells such as motor neurons may be dissociated and plated onto glass coverslips coated with poly-d-lysine and laminin. Motor neurons may be fed with a suitable medium such as a neurobasal medium supplemented with N2, B27, GDNF, BDNF, and CTNF. Cells may be maintained in a suitable medium such as an N2 medium (DMEM/F12 [1:1] supplemented with laminin [1 µg/mL; Invitrogen], FGF-2 [10 ng/ml; R&D Systems, Minneapolis, Minn.], and N2 supplement [1%; Invitrogen]), further supplemented with GDNF, BDNF, and CNTF, all at 10 ng/ml. Suitable media are described in Son et al., 2011, Conversion of mouse and human fibroblasts into functional spinal motor neurons, Cell Stem Cell 9:205-218; Vierbuchen et al., 2010, Direct conversion of fibroblasts to functional neurons by defined factors, Nature4 63:1035-1041; Kuo et al., 2003, Differentiation of monkey embryonic stem cells into neural lineages, Biology of Reproduction 68:1727-1735; and Wernig et al., 2002, Tau EGFP embryonic stem cells: an efficient tool for neuronal lineage selection and transplantation. J Neuroscience Res 69:918-24, each incorporated by reference.

3. Control Cell Line or Signature

Methods of the invention include causing the cell to express an optical reporter, observing a signature generated by the optical reporter, and comparing the observed signature to a control signature. The control signature may be obtained by obtaining a control cell that is also of the specific neural subtype and is genetically and phenotypically similar to the test cells. In certain embodiments—where, for example, a patient has a known mutation or allele at a certain locus—genetic editing is performed to generate a control cell line that but for the known mutation is isogenic with the test cell line. For example, where a patient is known to have the SOD1A4V mutation, genetic editing techniques can introduce a SOD1V4A mutation into the cell line to create a control cell line with a wild-type genotype and phenotype. Genetic or genome editing techniques may proceed via zinc-finger domain methods, transcription activator-like effector nucleases (TALENs), or clustered regularly interspaced short palindromic repeat (CRISPR) nucleases.

Genome editing techniques (e.g., use of zinc finger domains) may be used to create a control cell that is isogenic but-for a variant of interest. In certain embodiments, genome editing techniques are applied to the iPS cells. For example, a second corrected line (SOD1V4A) may be generated using zinc finger domains resulting in two otherwise isogenic lines. After that, diseased and corrected iPS cells may be differentiated into motor neurons using embryoid bodies according to the methods described above.

Genomic editing may be performed by any suitable method known in the art. For example, the chromosomal sequence encoding the target gene of interest may be edited using TALENs technology. TALENS are artificial restriction enzymes generated by fusing a TAL effector DNA binding domain to a DNA cleavage domain. In some embodiments, genome editing is performed using CRISPR technology. TALENs and CRISPR methods provide one-to-one relationship to the target sites, i.e. one unit of the tandem repeat in the TALE domain recognizes one nucleotide in the target site, and the crRNA or gRNA of CRISPR/Cas system hybridizes to the complementary sequence in the DNA target. Methods can include using a pair of TALENs or a Cas9 protein with one gRNA to generate double-strand breaks in the target. The breaks are then repaired via non-homologous end-joining or homologous recombination (HR).

TALENs uses a nonspecific DNA-cleaving nuclease fused to a DNA-binding domain that can be to target essentially any sequence. For TALEN technology, target sites are identified and expression vectors are made. See Liu et al, 2012, Efficient and specific modifications of the *Drosophila* genome by means of an easy TALEN strategy, J. Genet. Genomics 39:209-215. The linearized expression vectors (e.g., by NotI) and used as template for mRNA synthesis. A commercially available kit may be use such as the mMESSAGE mMACHINE SP6 transcription kit from Life Technologies (Carlsbad, Calif.). See Joung & Sander, 2013, TALENs: a wideliy applicable technology for targeted genome editing, Nat Rev Mol Cell Bio 14:49-55.

CRISPR methodologies employ a nuclease, CRISPR-associated (Cas9), that complexes with small RNAs as guides (gRNAs) to cleave DNA in a sequence-specific manner upstream of the protospacer adjacent motif (PAM) in any genomic location. CRISPR may use separate guide RNAs known as the crRNA and tracrRNA. These two separate RNAs have been combined into a single RNA to enable site-specific mammalian genome cutting through the design of a short guide RNA. Cas9 and guide RNA (gRNA) may be synthesized by known methods. Cas9/guide-RNA (gRNA) uses a non-specific DNA cleavage protein Cas9, and an RNA oligo to hybridize to target and recruit the Cas9/gRNA complex. See Chang et al., 2013, Genome editing with RNA-guided Cas9 nuclease in zebrafish embryos, Cell Res 23:465-472; Hwang et al., 2013, Efficient genome editing in zebrafish using a CRISPR-Cas system, Nat. Biotechnol 31:227-229; Xiao et al., 2013, Chromosomal deletions and inversions mediated by TALENS and CRISPR/Cas in zebrafish, Nucl Acids Res 1-11.

In certain embodiments, genome editing is performed using zinc finger nuclease-mediated process as described, for example, in U.S. Pub. 2011/0023144 to Weinstein.

Figure 3:
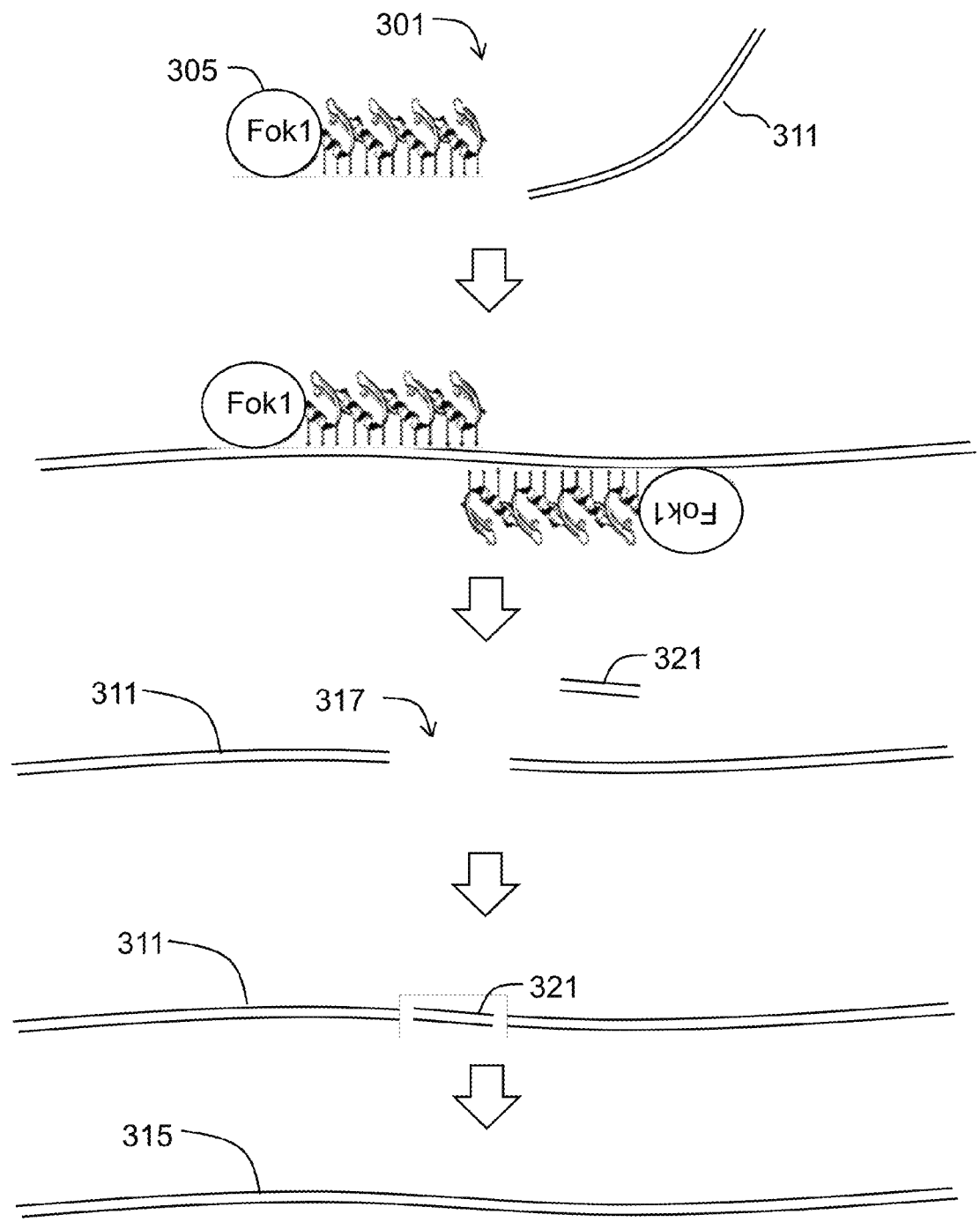
FIG. 3 gives an overview of zinc-finger nuclease mediated editing.

FIG. 3 gives an overview of a method 301 for zinc-finger nuclease mediated editing. Briefly, the method includes introducing into the iPS cell at least one RNA molecule encoding a targeted zinc finger nuclease 305 and, optionally, at least one accessory polynucleotide. The cell includes target sequence 311. The cell is incubated to allow expression of the zinc finger nuclease 305, wherein a double-stranded break 317 is introduced into the targeted chromosomal sequence 311 by the zinc finger nuclease 305. In some embodiments, a donor polynucleotide or exchange polynucleotide 321 is introduced. Target DNA 311 along with exchange polynucleotide 321 may be repaired by an error-prone non-homologous end-joining DNA repair process or a homology-directed DNA repair process. This may be used to produce a control line with a control genome 315 that is isogenic to original genome 311 but for a changed site. The genomic editing may be used to establish a control line (e.g., where the patient is known to have a certain mutation, the zinc finger process may revert the genomic DNA to wild type) or to introduce a mutation (e.g., non-sense, missense, or frameshift) or to affect transcription or expression.

Typically, a zinc finger nuclease comprises a DNA binding domain (i.e., zinc finger) and a cleavage domain (i.e., nuclease) and this gene may be introduced as mRNA (e.g., 5' capped, polyadenylated, or both). Zinc finger binding domains may be engineered to recognize and bind to any nucleic acid sequence of choice. See, for example, Beerli & Barbas, 2002, Engineering polydactyl zinc-finger transcription factors, Nat. Biotechnol, 20:135-141; Pabo et al., 2001, Design and selection of novel Cys2His2 zinc finger proteins, Ann. Rev. Biochem 70:313-340; Isalan et al., 2001, A rapid generally applicable method to engineer zinc fingers illustrated by targeting the HIV-1 promoter, Nat. Biotechnol 19:656-660; and Santiago et al., 2008, Targeted gene knock-out in mammalian cells by using engineered zinc-finger nucleases, PNAS 105:5809-5814. An engineered zinc finger binding domain may have a novel binding specificity compared to a naturally-occurring zinc finger protein. Engineering methods include, but are not limited to, rational design and various types of selection. A zinc finger binding domain may be designed to recognize a target DNA sequence via zinc finger recognition regions (i.e., zinc fingers). See for example, U.S. Pat. Nos. 6,607,882; 6,534,261 and 6,453,242, incorporated by reference. Exemplary methods of selecting a zinc finger recognition region may include phage display and two-hybrid systems, and are disclosed in U.S. Pat. Nos. 5,789,538; 5,925,523; 6,007,988; 6,013,453; 6,410,248; 6,140,466; 6,200,759; and U.S. Pat. No. 6,242,568, each of which is incorporated by reference.

Zinc finger binding domains and methods for design and construction of fusion proteins (and polynucleotides encoding same) are known to those of skill in the art and are described in detail in U.S. Pub. 2005/0064474 and U.S. Pub. 2006/0188987, each incorporated by reference. Zinc finger recognition regions, multi-fingered zinc finger proteins, or combinations thereof may be linked together using suitable linker sequences, including for example, linkers of five or more amino acids in length. See, U.S. Pat. Nos. 6,479,626; 6,903,185; and 7,153,949, incorporated by reference.

The zinc finger nuclease may use a nuclear localization sequence (NLS). A NLS is an amino acid sequence which facilitates targeting the zinc finger nuclease protein into the nucleus to introduce a double stranded break at the target sequence in the chromosome. Nuclear localization signals are known in the art. See, for example, Makkerh, 1996, Comparative mutagenesis of nuclear localization signals reveals the importance of neutral and acidic amino acids, Current Biology 6:1025-1027.

A zinc finger nuclease also includes a cleavage domain. The cleavage domain portion of the zinc finger nucleases may be obtained from any suitable endonuclease or exonuclease such as restriction endonucleases and homing endonucleases. See, for example, Belfort & Roberts, 1997, Homing endonucleases: keeping the house in order, Nucleic Acids Res 25(17):3379-3388. A cleavage domain may be derived from an enzyme that requires dimerization for cleavage activity. Two zinc finger nucleases may be required for cleavage, as each nuclease comprises a monomer of the active enzyme dimer. Alternatively, a single zinc finger nuclease may comprise both monomers to create an active enzyme dimer. Restriction endonucleases present may be capable of sequence-specific binding and cleavage of DNA at or near the site of binding. Certain restriction enzymes (e.g., Type IIS) cleave DNA at sites removed from the recognition site and have separable binding and cleavage domains. For example, the Type IIS enzyme FokI, active as a dimer, catalyzes double-stranded cleavage of DNA, at 9 nucleotides from its recognition site on one strand and 13 nucleotides from its recognition site on the other. The FokI enzyme used in a zinc finger nuclease may be considered a cleavage monomer. Thus, for targeted double-stranded cleavage using a FokI cleavage domain, two zinc finger nucleases, each comprising a FokI cleavage monomer, may be used to reconstitute an active enzyme dimer. See Wah, et al., 1998, Structure of FokI has implications for DNA cleavage, PNAS 95:10564-10569; U.S. Pat. Nos. 5,356,802; 5,436,150 and 5,487,994, each incorporated by reference. In certain embodiments, the cleavage domain may comprise one or more engineered cleavage monomers that minimize or prevent homo-dimerization, as described, for example, in U.S. Patent Publication Nos. 2005/0064474, 2006/0188987, and 2008/0131962, each incorporated by reference.

Genomic editing by the zinc finger nuclease-mediated process may include introducing at least one donor polynucleotide comprising a sequence into the cell. A donor polynucleotide preferably includes the sequence to be introduced flanked by an upstream and downstream sequence that share sequence similarity with either side of the site of integration in the chromosome. The upstream and downstream sequences in the donor polynucleotide are selected to promote recombination between the chromosomal sequence of interest and the donor polynucleotide. Typically, the donor polynucleotide will be DNA. The donor polynucleotide may be a DNA plasmid, a bacterial artificial chromosome (BAC), a yeast artificial chromosome (YAC), a viral vector, a linear piece of DNA, a PCR fragment, a naked nucleic acid, and may employ a delivery vehicle such as a liposome. The sequence of the donor polynucleotide may include exons, introns, regulatory sequences, or combinations thereof.

The double stranded break is repaired via homologous recombination with the donor polynucleotide such that the desired sequence is integrated into the chromosome.

In some embodiments, methods for genome editing include introducing into the cell an exchange polynucleotide (typically DNA) with a sequence that is substantially identical to the chromosomal sequence at the site of cleavage and which further comprises at least one specific nucleotide change. Where the cells have been obtained from a subject suspected to have a neurodegenerative disease, a method such as TALENs, CRISPRs, or zinc fingers may be used to make a control cell line. For example, if the cell line is SOD1A4V, methods may be used to produce a cell line that is isogenic but SOD1V4A. While any such technology may be used, the following illustrates genome editing via zinc finger nucleases.

In general, with zinc-finger nucleases, the sequence of the exchange polynucleotide will share enough sequence identity with the chromosomal sequence such that the two sequences may be exchanged by homologous recombination. The sequence in the exchange polynucleotide comprises at least one specific nucleotide change with respect to the sequence of the corresponding chromosomal sequence. For example, one nucleotide in a specific codon may be changed to another nucleotide such that the codon codes for a different amino acid. In one embodiment, the sequence in the exchange polynucleotide may comprise one specific nucleotide change such that the encoded protein comprises one amino acid change.

In the zinc finger nuclease-mediated process for modifying a chromosomal sequence, a double stranded break introduced into the chromosomal sequence by the zinc finger nuclease is repaired, via homologous recombination with the exchange polynucleotide, such that the sequence in the exchange polynucleotide may be exchanged with a portion of the chromosomal sequence. The presence of the double stranded break facilitates homologous recombination and repair of the break. The exchange polynucleotide may be physically integrated or, alternatively, the exchange polynucleotide may be used as a template for repair of the break, resulting in the exchange of the sequence information in the exchange polynucleotide with the sequence information in that portion of the chromosomal sequence. Thus, a portion of the endogenous chromosomal sequence may be converted to the sequence of the exchange polynucleotide.

To mediate zinc finger nuclease genomic editing, at least one nucleic acid molecule encoding a zinc finger nuclease and, optionally, at least one exchange polynucleotide or at least one donor polynucleotide are delivered to the cell of interest. Suitable methods of introducing the nucleic acids to the cell include microinjection, electroporation, calcium phosphate-mediated transfection, cationic transfection, liposome transfection, heat shock transfection, lipofection, and delivery via liposomes, immunoliposomes, virosomes, or artificial virions.

The method of inducing genomic editing with a zinc finger nuclease further comprises culturing the cell comprising the introduced nucleic acid to allow expression of the zinc finger nuclease. Cells comprising the introduced nucleic acids may be cultured using standard procedures to allow expression of the zinc finger nuclease. Typically, the cells are cultured at an appropriate temperature and in appropriate media with the necessary $O_2/CO_2$ ratio to allow the expression of the zinc finger nuclease. Suitable non-limiting examples of media include M2, M16, KSOM, BMOC, and HTF media. Standard cell culture techniques are described, for example, in Santiago et al, 2008, Targeted gene knockout in mammalian cells by using engineered zinc finger nucleases, PNAS 105:5809-5814; Moehle et al., 2007, Targeted gene addition into a specified location in the human genome using designed zinc finger nucleases PNAS 104:3055-3060; Urnov et al., 2005, Highly efficient endogenous human gene correction using designed zinc-finger nucleases, Nature 435(7042):646-51; and Lombardo et al., 2007, Gene editing in human stem cells using zinc finger nucleases and integrase-defective lentiviral vector delivery, Nat Biotechnol 25(11):1298-306. Those of skill in the art appreciate that methods for culturing cells are known in the art and can and will vary depending on conditions. Upon expression of the zinc finger nuclease, the target sequence is edited. In cases in which the cell includes an expressed zinc finger nuclease as well as a donor (or exchange) polynucleotide, the zinc finger nuclease recognizes, binds, and cleaves the target sequence in the chromosome. The double-stranded break introduced by the zinc finger nuclease is repaired, via homologous recombination with the donor (or exchange) polynucleotide, such that the sequence in the donor polynucleotide is integrated into the chromosomal sequence (or a portion of the chromosomal sequence is converted to the sequence in the exchange polynucleotide). As a consequence, a sequence may be integrated into the chromosomal sequence (or a portion of the chromosomal sequence may be modified).

Using genome editing for modifying a chromosomal sequence, an isogenic (but for the mutation of interest) control line can be generated. In certain embodiments, a control cells are obtained from healthy individuals, i.e., without using genome editing on cells taken from the subject. The control line can be used in the analytical methods described herein to generate a control signature for comparison to test data. In some embodiments, a control signature is stored on-file after having been previously generated and stored and the stored control signature is used (e.g., a digital file such as a graph or series of measurements stored in a non-transitory memory in a computer system). For example, a control signature could be generated by assaying a large population of subjects of known phenotype or genotype and storing an aggregate result as a control signature for later downstream comparisons.

4. Causing Cells to Express Optogenetic Systems

4a. Causing a Cell to Express an Optogenetic Reporter

The patient's test cell line and the optional control line may be caused to express an optical reporter of neural or electrical activity. Examples of neural activity include action potentials in a neuron or fusion of vesicles releasing neurotransmitters. Exemplary electrical activity includes action potentials in a neuron, cardiomyocyte, astrocyte or other electrically active cell. Further examples of neural or electrical activity include ion pumping or release or changing ionic gradients across membranes. Causing a cell to express an optical reporter of neural activity can be done with a fluorescent reporter of vesicle fusion. Expressing an optical reporter of neural or electrical activity can include transformation with an optogenetic reporter. For example, the cell may be transformed with a vector comprising an optogenetic reporter and the cell may also be caused to express an optogenetic actuator by transformation. In certain embodiments, the differentiated neurons are cultured (e.g., for about 4 days) and then infected with lentivirus bearing a genetically encoded optical reporter of neural activity and optionally an optical voltage actuator.

Any suitable optical reporter of neural activity may be used. Exemplary reporters include fluorescent reporters of transmembrane voltage differences, pHluorin-based reporters of synaptic vesicle fusion, and genetically encoded calcium indicators. In a preferred embodiment, a genetically encoded voltage indicator is used. Genetically encoded voltage indicators that may be used or modified for use with methods of the invention include FlaSh (Siegel, 1997, A genetically encoded optical probe of membrane voltage. Neuron 19:735-741); SPARC (Ataka, 2002, A genetically targetable fluorescent probe of channel gating with rapid kinetics, Biophys J 82:509-516); and VSFP1 (Sakai et al., 2001, Design and characterization of a DNA encoded, voltage-sensitive fluorescent protein, Euro J Neuroscience 13:2314-2318). A genetically encoded voltage indicator based on the paddle domain of a voltage-gated phosphatase is CiVSP (Murata et al., 2005, Phosphoinositide phosphatase activity coupled to an intrinsic voltage sensor, Nature 435: 1239-1243). Another indicator is the hybrid hVOS indicator (Chanda et al., 2005, A hybrid approach to measuring electrical activity in genetically specified neurons, Nat Neuroscience 8:1619-1626), which transduces the voltage dependent migration of dipicrylamine (DPA) through the membrane leaflet to "dark FRET" (fluorescence resonance energy transfer) with a membrane-targeted GFP.

Optical reporters that may be suitable for use with the invention include those from the family of proteins of known microbial rhodopsins. A reporter based on a microbial rhodopsin may provide high sensitivity and speed. Suitable indicators include those that use the endogenous fluorescence of the microbial rhodopsin protein Archaerhodopsin 3 (Arch) from *Halorubum sodomense*. Arch resolves action potentials with high signal-to-noise (SNR) and low phototoxicity. A mutant form of Arch, D95N, has been shown not to exhibit a hyperpolarizing current associated with some indicators. Other mutant forms of Arch, termed QuasAr1 and QuasAr2, have been shown to exhibit improved brightness, sensitivity to voltage, speed of response, and trafficking to the neuronal plasma membrane. Arch and the above-mentioned variants target eukaryotic membranes and can image single action potentials and subthreshold depolarization in cultured mammalian neurons. See Kralj et al, 2012, Optical recording of action potentials in mammalian neurons using a microbial rhodopsin, Nat Methods 9:90-95. Thus Arch and variants of Arch such as Arch(D95N) may provide good optical reporters of neural activity according to embodiments of the invention.

In some embodiments, an improved variant of Arch such as QuasAr1 or QuasAr2 is used. QuasAr1 comprises Arch with the mutations: P60S, T80S, D95H, D106H, and F161V. QuasAr2 comprises Arch with the mutations: P60S, T80S, D95Q, D106H, and F161V. Positions Asp95 and Asp106 of Arch (which are structurally aligned with positions Asp85 and Asp96 of bacteriorhodopsin, and have been reported to play key roles in proton translocation during the photo cycle) are targets for modification because they flank the Schiff base in the proton-transport chain and are likely important in determining voltage sensitivity and speed. The other mutations improve the brightness of the protein. Starting with an Arch gene, it may be beneficial to add endoplasmic reticulum (ER) export motifs and a trafficking sequence (TS) according to methods known in the art.

Figure 4:
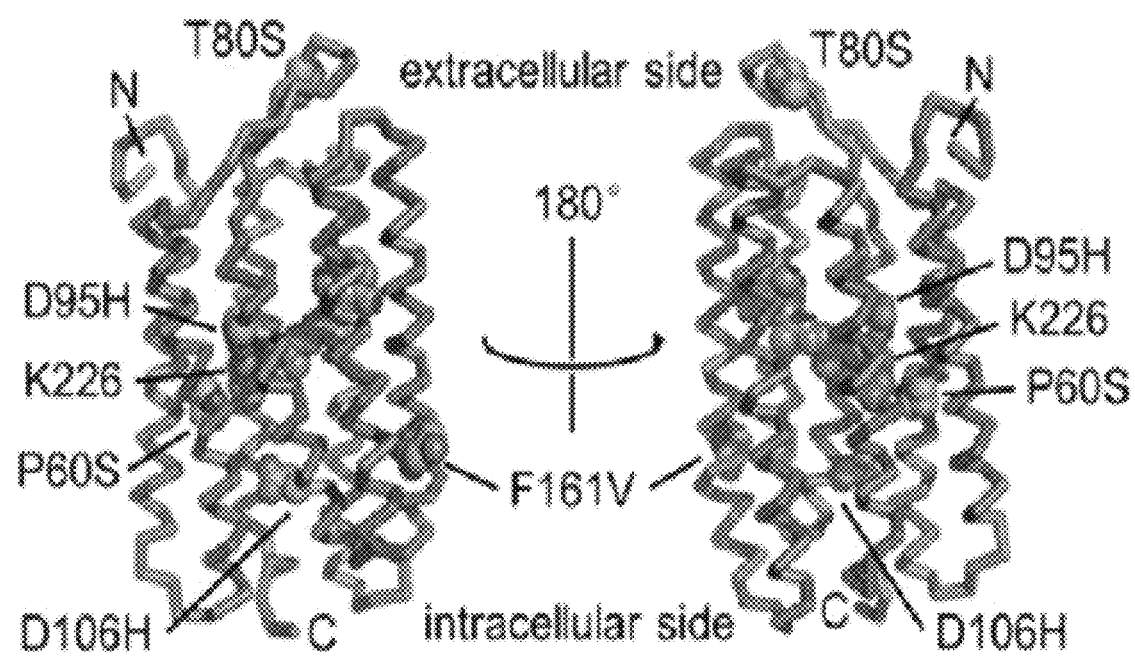
FIG. 4 presents a structural model of an optical reporter of neural activity.

FIG. 4 presents a structural model of Quasar1 based on homologous protein Arch-2 (PDB: 2E14, described in Enami et al, 2006, Crystal structures of archaerhodopsin-1 and -2: Common structural motif in Archaeal light-driven proton pumps, J Mol Bio. 358:675-685). Mutations T80S and F161V are located in the periphery of the protein, while P60S is close to the Schiff base of the retinal chromophore. Given their location, T80S and F161V substitutions are unlikely to have a direct impact on the photo-physical properties of the protein, and are more likely to have a role in improving the folding efficiency. In contrast, the close proximity of the P60S substitution to the Schiff base suggests that this mutation has a more direct influence on the photo-physical properties. The QuasAr indicators may exhibit improved voltage sensitivity, response kinetics, membrane trafficking and diminished dependence of brightness on illumination intensity relative to Arch. The fluorescence quantum yields of solubilized QuasAr1 and 2 may be 19- and 10-fold enhanced, respectively, relative to the non-pumping voltage indicator Arch(D95N). QuasAr1 may be 15-fold brighter than wild-type Arch, and QuasAr2 may be 3.3-fold brighter. Neither mutant shows the optical nonlinearity seen in the wild-type protein. Fluorescence of Arch, QuasAr1, and QuasAr2 increase nearly linearly with membrane voltage between −100 mV and +50 mV. Fluorescence recordings may be acquired on an epifluorescence microscope, described in Kralj et al., 2012, Optical recording of action potentials in mammalian neurons using a microbial rhodopsin, Nat. Methods 9:90-95.

QuasAr1 and QuasAr2 each refer to a specific variant of Arch. As discussed, archaerhodopsin 3 (Arch) functions as a fast and sensitive voltage indicator. Improved versions of Arch include the QuasArs ('quality superior to Arch'), described in Hochbaum et al., 2014. QuasAr1 differs from wild-type Arch by the mutations P60S, T80S, D95H, D106H and F161V. QuasAr2 differed from QuasAr1 by the mutation H95Q. QuasAr1 and QuasAr2 report action potentials (APs).

Figure 21:
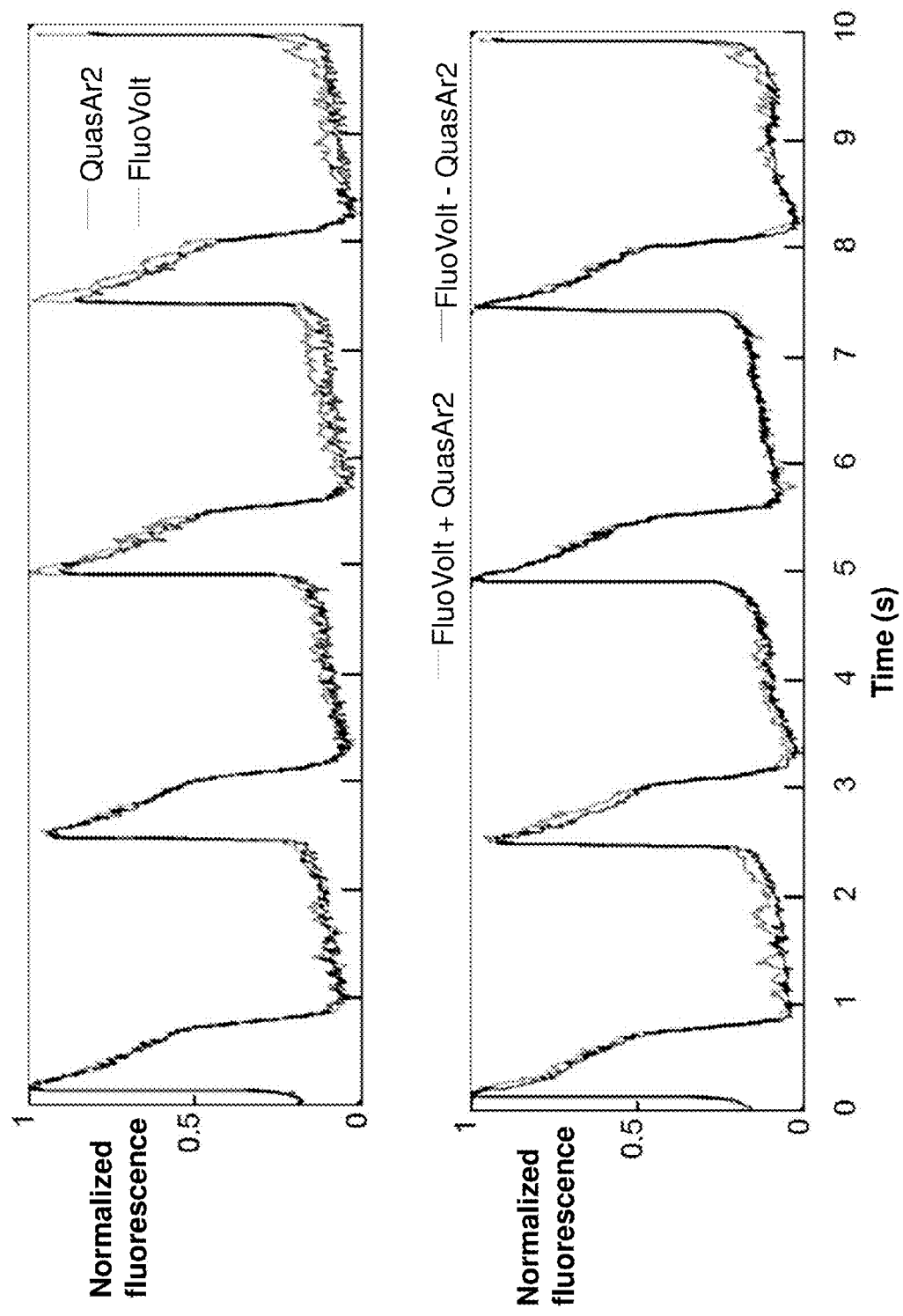
FIG. 21 gives a comparison of AP waveforms as measured by the genetically encoded voltage indicator QuasAr2 and the voltage-sensitive dye, FluoVolt.

FIG. 21 gives a comparison of AP waveforms as measured by the genetically encoded voltage indicator QuasAr2 and the voltage-sensitive dye, FluoVolt. Cells are sparsely transfected with the QuasAr2 construct and then treated with FluoVolt dye. QuasAr2 is excited by red laser light at a wavelength of 635 nm with fluorescence detection centered at 720 nm. FluoVolt is excited by 488 nm laser light with fluorescence detection centered at 525 nm. The top panel shows the simultaneously recorded AP waveforms from a cell expressing QuasAr2 (red line) and labeled with FluoVolt (green line). The similarity of these traces establishes that QuasAr2 fluorescence accurately represents the underlying AP waveform. The lower trace compares the FluoVolt AP waveform in the presence (FluoVolt+, QuasAr2+, green) and absence (FluoVolt+, QuasAr2−, cyan) of QuasAr2 expression. The similarity of these two traces establishes that expression of QuasAr2 does not perturb the AP waveform.

Figure 22:
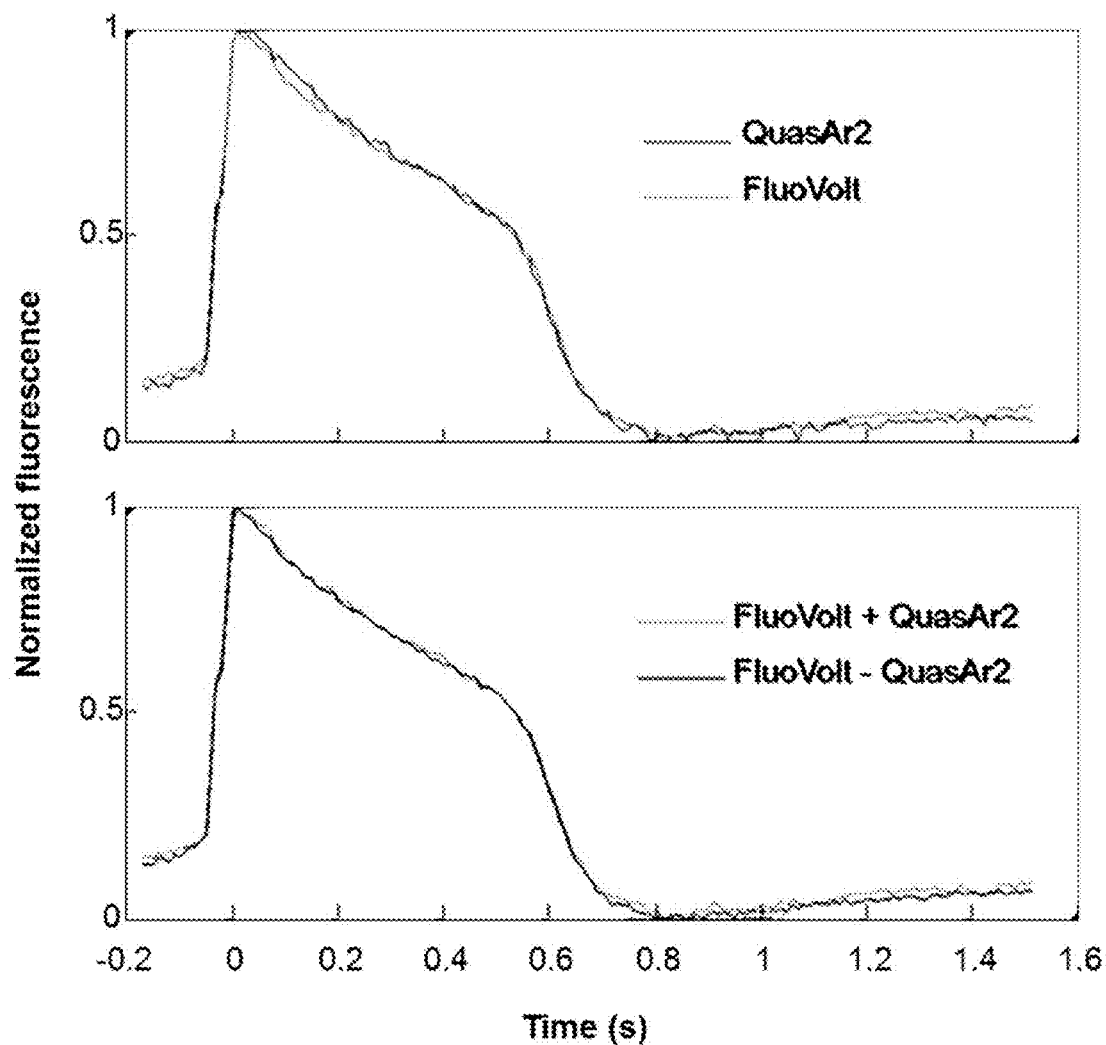
FIG. 22 shows plots of the average waveforms from the traces in FIG. 21.

FIG. 22 shows plots of the average waveforms from the traces in FIG. 21.

Figure 23:
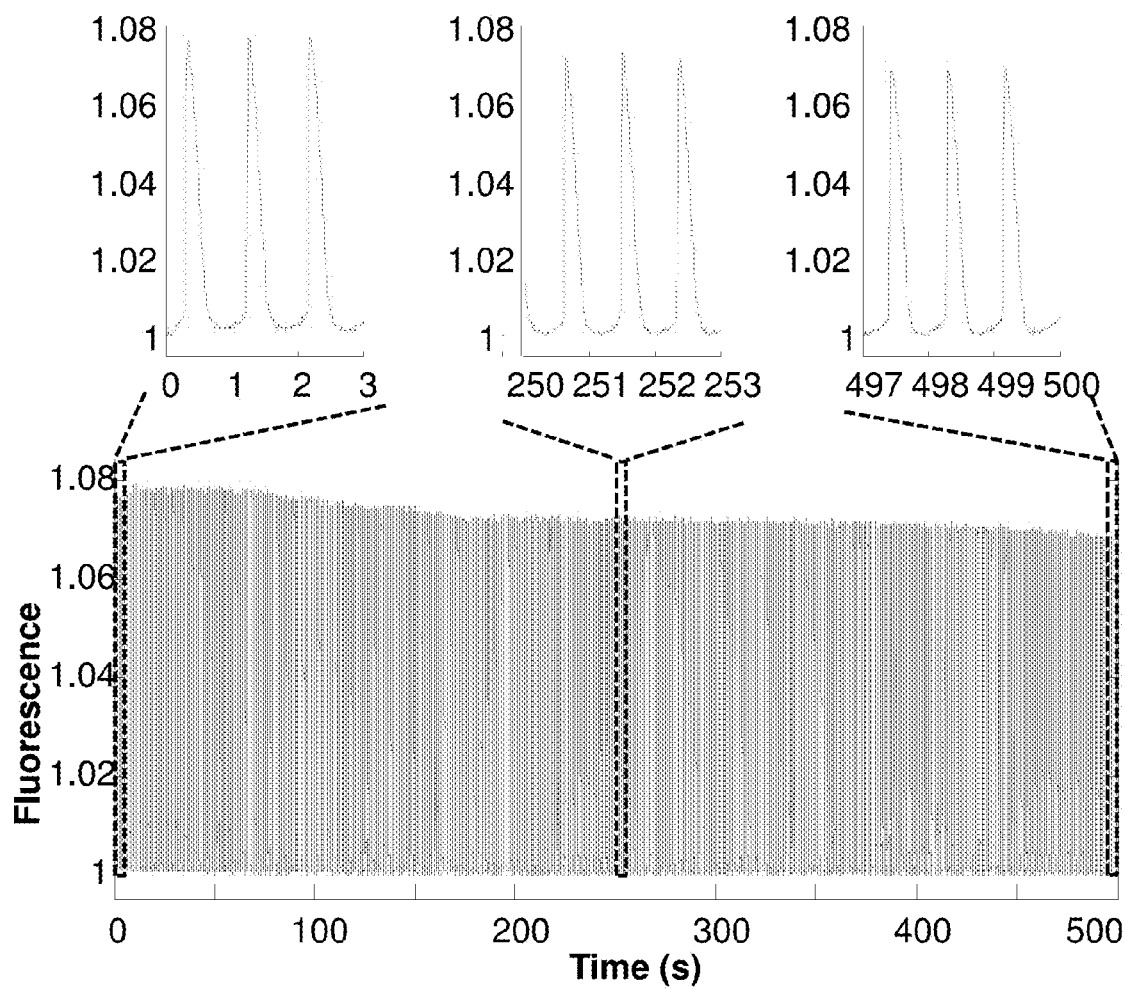
FIG. 23 presents phototoxicity and photobleaching measurement of QuasAr2.

FIG. 23 presents phototoxicity and photobleaching measurement of QuasAr2. Cells are imaged under continuous red laser illumination (~50 W/cm2) for 500 s. Expanded views of the fluorescence recording are shown in the lower panels.

Figure 24:
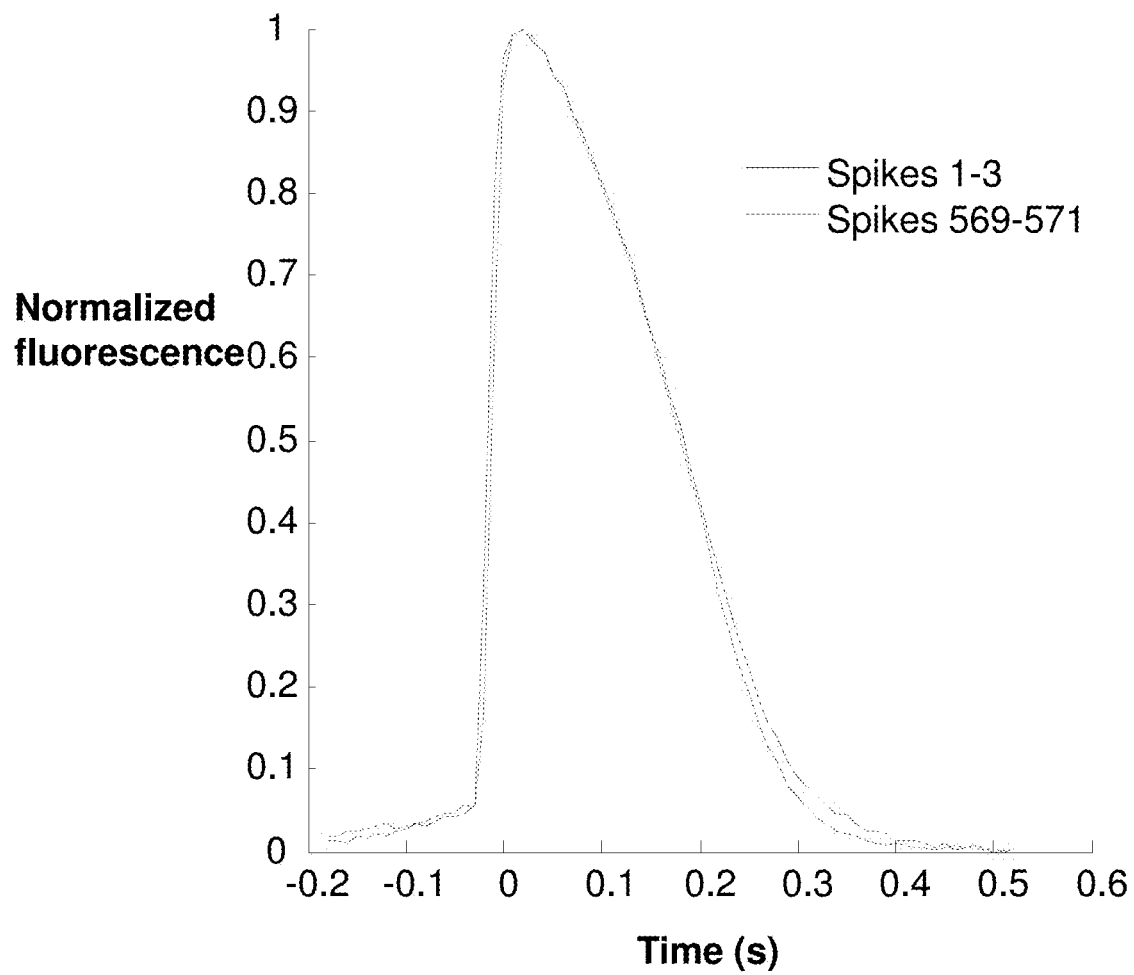
FIG. 24 graphs the average AP waveform shapes.

FIG. 24 graphs the average AP waveform shapes for the beginning (blue) and end (green) of the trace in FIG. 23.

Arch and the above-mentioned variants target eukaryotic membranes and can image single action potentials and subthreshold depolarization in cultured mammalian neurons. See Kralj et al, 2012, Optical recording of action potentials in mammalian neurons using a microbial rhodopsin, Nat Methods 9:90-95 and Hochbaum et al., All-optical electrophysiology in mammalian neurons using engineered microbial rhodopsins, Nature Methods, 11, 825-833 (2014), both incorporated by reference. Thus Arch and variants of Arch may provide good optical reporters of electrical activity according to embodiments of the invention.

The invention provides optical reporters based on Archaerhodopsins that function in mammalian cells, including human stem cell-derived neurons. These proteins indicate electrical dynamics with sub-millisecond temporal resolution and sub-micron spatial resolution and may be used in non-contact, high-throughput, and high-content studies of electrical dynamics in cells and tissues using optical measurement of membrane potential. These reporters are broadly useful, particularly in eukaryotic, such as mammalian, including human cells.

The invention includes reporters based on Archaerhodopsin 3 (Arch 3) and its homologues. Arch 3 is Archaerhodopsin from *H. sodomense* and it is known as a genetically-encoded reagent for high-performance yellow/green-light neural silencing. Gene sequence at GenBank: GU045593.1 (synthetic construct Arch 3 gene, complete cds. Submitted Sep. 28, 2009). These proteins localize to the plasma membrane in eukaryotic cells and show voltage-dependent fluorescence.

Fluorescence recordings may be acquired on an epifluorescence microscope, described in Hochbaum et al., All-optical electrophysiology in mammalian neurons using engineered microbial rhodopsins, Nature Methods, 11, 825-833 (2014), incorporated by reference.

Optical reporters of the invention show high sensitivity. In mammalian cells, Archaerhodopsin-based reporters show about 3-fold increase in fluorescence between −150 mV and +150 mV. The response is linear over most of this range. Membrane voltage can be measured with a precision of <1 mV in a 1 s interval. Reporters of the invention show high speed. QuasAr1 shows 90% of its step response in 0.05 ms. The upstroke of a cardiac AP lasts approximately 1 ms, so the speeds of Arch-derived indicators meet the benchmark for imaging electrical activity. Reporters of the invention show high photo-stability and are comparable to GFP in the number of fluorescence photons produced prior to photobleaching. The reporters may also show far red spectrum. The Arch-derived voltage-indicating protein reporters, sometimes referred to as genetically encoded voltage indicators (GEVIs), may be excited with a laser at wavelengths between 590-640 nm, and the emission is in the near infrared, peaked at 710 nm. The emission is farther to the red than any other existing fluorescent protein. These wavelengths coincide with low cellular auto-fluorescence. This feature makes these proteins particularly useful in optical measurements of action potentials as the spectrum facilitates imaging with high signal-to-noise ratio, as well as multispectral imaging in combination with other fluorescent probes.

Other optogenetic reporters may be used with methods and systems of the invention. Suitable optogenetic reporters include the two Arch variants dubbed Archer1 and Archer2 reported in Flytzanis, et al., 2014, Archaerhodopsin variants with enhanced voltage-sensitive fluorescence in mammalian and *Caenorhabditis elegans* neurons, Nat Comm 5:4894, incorporated by reference. Archer1 and Archer2 exhibit enhanced radiance in response to 655 nm light have 3-5 times increased fluorescence and 55-99 times reduced photocurrents compared with Arch WT. Archer1 (D95E and T99C) and Archer2 (D95E, T99C and A225M) may be used for voltage sensing. These mutants exhibit high baseline fluorescence (×3-5 over Arch WT), large dynamic range of sensitivity (85% DF/F and 60% DF/F per 100 mV for Archer1 and Archer2, respectively) that is stable over long illumination times, and fast kinetics, when imaged at ×9 lower light intensity (880 mW mm$^{-2}$ at 655 nm) than the most recently reported Arch variants. Archer1's characteristics allow its use to monitor rapid changes in membrane voltage throughout a single neuron and throughout a population of neurons in vitro. Although Archer1 has minimal pumping at wavelengths used for fluorescence excitation (655 nm), it maintains strong proton pumping currents at lower wavelengths (560 nm). Archer1 provides a bi-functional tool with both voltage sensing with red light and inhibitory capabilities with greenlight. Archer1 is capable of detecting small voltage changes in response to sensory stimulus Suitable optogenetic reporters include the Arch-derived voltage sensors with trafficking signals for enhanced localization as well as the Arch mutants dubbed Arch-EEN and Arch-EEQ reported in Gong et al., Enhanced Archaerhodopsin fluorescent protein voltage indicators, PLoSOne 8(6):e66959, incorporated by reference. Such reporters may include variants of Arch with the double mutations D95N-D106E (Arch-EEN) and D95Q-D106E (Arch-EEQ).

Suitable optogenetic reporters include sensors that use fluorescence resonance energy transfer (FRET) to combine rapid kinetics and the voltage dependence of the rhodopsin family voltage-sensing domains with the brightness of genetically engineered protein fluorophores. Such FRET-opsin sensors offer good spike detection fidelity, fast kinetics, and high brightness. FRET-opsin sensors are described in Gong et al., Imaging neural spiking in brain tissue using FRET-opsin protein voltage sensors, Nat Comm 5:3674, incorporated by reference. A suitable FRET-opsin may include a fusion of a bright fluorophore to act as a FRET donor to a Mac rhodopsin molecule to server as both the voltage sensing domain and the FRET acceptor. Other sensors include the Accelerated Sensor of Action Potentials (ASAP1), a voltage sensor formed by insertion of a circularly permuted GFP into a chicken voltage-sensitive phosphatase. St-Pierre, 2014, High-fidelity optical reporting of neuronal electrical activity with an ultrafast fluorescent voltage sensor, Nat Neurosci 17(6):884, incorporated by reference. Other suitable reporters may include the ArcLight-derived probe dubbed Bongwoori and described in Piao et al., 2015, Combinatorial mutagenesis of the voltage-sensing domain enables the optical resolution of action potentials firing at 60 Hz by a genetically encoded fluorescent sensor of membrane potential, J Neurosci 35(1):372-385, incorporated by reference.

4b. Causing a Cell to Express an Optogenetic Actuator

In a preferred embodiment, the cells are transformed with an optical voltage actuator. This can occur, for example, simultaneously with transformation with the vector comprising the optogenetic reporter. The far-red excitation spectrum of the QuasAr reporters suggests that they may be paired with a blue light-activated channelrhodopsin to achieve all-optical electrophysiology. For spatially precise optical excitation, the channelrhodopsin should carry current densities sufficient to induce APs when only a subsection of a cell is excited. Preferably, light used for imaging the reporter should not activate the actuator, and light used for activating the actuator should not confound the fluorescence signal of the reporter. Thus in a preferred embodiment, an optical actuator and an optical reporter are spectrally orthogonal to avoid crosstalk and allow for simultaneous use. Spectrally orthogonal systems are discussed in Carlson and Campbell, 2013, Circular permutated red fluorescent proteins and calcium ion indicators based on mCherry, Protein Eng Des Sel 26(12):763-772.

Preferably, a genetically-encoded optogenetic actuator is used. One actuator is channelrhodopsin2 H134R, an optogenetic actuator described in Nagel, G. et al., 2005, Light activation of channelrhodopsin-2 in excitable cells of *Caenorhabditis elegans* triggers rapid behavioral responses, Curr. Biol. 15, 2279-2284.

A screen of plant genomes has identified an optogenetic actuator, Scherffelia *dubia* ChR (sdChR), derived from a fresh-water green alga first isolated from a small pond in Essex, England. See Klapoetke et al., 2014, Independent optical excitation of distinct neural populations, Nat Meth Advance Online Publication 1-14; see also Melkonian & Preisig, 1986, A light and electron microscopic study of *Scherffelia dubia*, a new member of the scaly green *flagellates* (Prasinophyceae). Nord. J. Bot. 6:235-256, both incorporated by reference. SdChR may offer good sensitivity and a blue action spectrum.

An improved version of sdChR dubbed CheRiff may be used as an optical actuator. The gene for *Scherffelia dubia* Channelrhodopsin (sdChR) (selected from a screen of channelrhodopsins for its blue excitation peak (474 nm) and its large photocurrent relative to ChR2) is synthesized with mouse codon optimization, a trafficking sequence from Kir2.1 is added to improve trafficking, and the mutation E154A is introduced. CheRiff exhibits significantly decreased crosstalk from red illumination (to 10.5±2.8 pA) allowing its use in cells along with optogenetic reporters described herein. CheRiff shows good expression and membrane trafficking in cultured rat hippocampal neurons. The maximum photocurrent under saturating illumination (488 nm, 500 mW/cm) is 2.0±0.1 nA (n=10 cells), approximately 2-fold larger than the peak photocurrents of ChR2 H134R or ChIEF (Lin et al., 2009, Characterization of engineered channelrhodopsin variants with improved properties and kinetics, Biophys J 96:1803-1814). In neurons expressing CheRiff, whole-cell illumination at only 22±10 mW/cm induces a photocurrent of 1 nA. Compared to ChR2 H134R and to ChIEF under standard channelrhodopsin illumination conditions (488 nm, 500 mW/cm). At 23° C., CheRiff reaches peak photocurrent in 4.5±0.3 ms (n=10 cells). After a 5 ms illumination pulse, the channel closing time constant was comparable between CheRiff and ChIEF (16±0.8 ms, n=9 cells, and 15±2 ms, n=6 cells, respectively, p=0.94), and faster than ChR2 H134R (25±4 ms, n=6 cells, p<0.05). Under continuous illumination CheRiff partially desensitizes with a time constant of 400 ms, reaching a steady-state current of 1.3±0.08 nA (n=10 cells). Illumination of neurons expressing CheRiff induces trains of APs with high reliability and high repetition-rate.

When testing for optical crosstalk between QuasArs and CheRiff in cultured neurons, illumination sufficient to induce high-frequency trains of APs (488 nm, 140 mW/cm) perturbed fluorescence of QuasArs by <1%. Illumination with high intensity red light (640 nm, 900 W/cm) induced an inward photocurrent through CheRiff of 14.3±3.1 pA, which depolarized neurons by 3.1±0.2 mV (n=5 cells). ChIEF and ChR2 H134R generated similar red light photocurrents and depolarizations. For most applications this level of optical crosstalk is acceptable.

In some embodiments it is preferred to have an actuator whose activation is maximal at a violet light wavelength between 400-440 nm, further to the blue than CheRiff. Violet-activated channelrhodopsins can be simultaneously combined with yellow-excited Ca2+ indicators (e.g. jRCaMP1a, jRGECO1a, and R-CaMP2) and a red-excited voltage indicator, e.g. QuasAr2, for simultaneous monitoring of Ca2+ and voltage under optical stimulus conditions.

A preferred violet-excited channelrhodopsin actuator is TsChR, derived from *Tetraselmis striata* (See Klapoetke et al., 2014, Independent optical excitation of distinct neural populations, Nat. Meth. 11, 338-346 (2014)). This channelrhodopsin actuator has a blue-shifted action spectrum with a peak at 435 nm. Another preferred violet channelrhodopsin actuator is PsChR, derived from Platymonas subcordiformis (see Govorunova, Elena et al., 2013, Characterization of a highly efficient blue-shifted channelrhodopsin from the marine alga Platymonas subcordiformis, J Biol Chem 288 (41):29911-29922). PsChr has a blue-shifted action spectrum with a peak at 437 nm. PsChR and TsChR are advantageously paired with red-shifted Ca2+ indicators and can be used in the same cell or same field of view as these red-shifted Ca2+ indicators without optical crosstalk.

4c. Vectors for Expression of Optogenetic Systems

The optogenetic reporters and actuators may be delivered in constructs described here as optopatch constructs delivered through the use of an expression vector. Optopatch may be taken to refer to systems that perform functions traditionally associated with patch clamps, but via an optical input, readout, or both as provided for by, for example, an optical reporter or actuator. An Optopatch construct may include a bicistronic vector for co-expression of CheRiff-eGFP and QuasAr1- or QuasAr2-mOrange2. The QuasAr and CheRiff constructs may be delivered separately, or a bicistronic expression vector may be used to obtain a uniform ratio of actuator to reporter expression levels.

The genetically encoded reporter, actuator, or both may be delivered by any suitable expression vector using methods known in the art. An expression vector is a specialized vector that contains the necessary regulatory regions needed for expression of a gene of interest in a host cell. In some embodiments the gene of interest is operably linked to another sequence in the vector. In some embodiments, it is preferred that the viral vectors are replication defective, which can be achieved for example by removing all viral nucleic acids that encode for replication. A replication defective viral vector will still retain its infective properties and enters the cells in a similar manner as a replicating vector, however once admitted to the cell a replication defective viral vector does not reproduce or multiply. The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of coding sequences and transcription control elements (e.g. promoters, enhancers, and termination elements) in an expression vector.

Many viral vectors or virus-associated vectors are known in the art. Such vectors can be used as carriers of a nucleic acid construct into the cell. Constructs may be integrated and packaged into non-replicating, defective viral genomes like Adenovirus, Adeno-associated virus (AAV), or Herpes simplex virus (HSV) or others, including retroviral and lentiviral vectors, for infection or transduction into cells. The vector may or may not be incorporated into the cell's genome. The constructs may include viral sequences for transfection, if desired. Alternatively, the construct may be incorporated into vectors capable of episomal replication, such as an Eptsein Barr virus (EPV or EBV) vector. The inserted material of the vectors described herein may be operatively linked to an expression control sequence when the expression control sequence controls and regulates the transcription and translation of that polynucleotide sequence. In some examples, transcription of an inserted material is under the control of a promoter sequence (or other transcriptional regulatory sequence) which controls the expression of the recombinant gene. In some embodiments, a recombinant cell containing an inducible promoter is used and exposed to a regulatory agent or stimulus by externally applying the agent or stimulus to the cell or organism by exposure to the appropriate environmental condition or the operative pathogen. Inducible promoters initiate transcription only in the presence of a regulatory agent or stimulus. Examples of inducible promoters include the tetracycline response element and promoters derived from the beta-interferon gene, heat shock gene, metallothionein gene or any obtainable from steroid hormone-responsive genes. Inducible promoters which may be used in performing the methods of the present invention include those regulated by hormones and hormone analogs such as progesterone, ecdysone and glucocorticoids as well as promoters which are regulated by tetracycline, heat shock, heavy metal ions, interferon, and lactose operon activating compounds. See Gingrich and Roder, 1998, Inducible gene expression in the nervous system of transgenic mice, Annu Rev Neurosci 21:377-405. Tissue specific expression has been well characterized in the field of gene expression and tissue specific and inducible promoters are well known in the art. These promoters are used to regulate the expression of the foreign gene after it has been introduced into the target cell. In certain embodiments, a cell-type specific promoter or a tissue-specific promoter is used. A cell-type specific promoter may include a leaky cell-type specific promoter, which regulates expression of a selected nucleic acid primarily in one cell type, but cause expression in other cells as well. For expression of an exogenous gene specifically in neuronal cells, a neuron-specific *enolase* promoter can be used. See Forss-Petter et al., 1990, Transgenic mice expressing beta-galactosidase in mature neurons under neuron specific *enolase* promoter control, Neuron 5: 187-197. For expression of an exogenous gene in dopaminergic neurons, a tyrosine hydroxylase promoter can be used.

In some embodiments, the expression vector is a lentiviral vector. Lentiviral vectors may include a eukaryotic promoter. The promoter can be any inducible promoter, including synthetic promoters, that can function as a promoter in a eukaryotic cell. For example, the eukaryotic promoter can be, but is not limited to, CamKIIα promoter, human Synapsin promoter, ecdysone inducible promoters, Ela inducible promoters, tetracycline inducible promoters etc., as are well known in the art. In addition, the lentiviral vectors used herein can further comprise a selectable marker, which can comprise a promoter and a coding sequence for a selectable trait. Nucleotide sequences encoding selectable markers are well known in the art, and include those that encode gene products conferring resistance to antibiotics or anti-metabolites, or that supply an auxotrophic requirement. Examples of such sequences include, but are not limited to, those that encode thymidine kinase activity, or resistance to methotrexate, ampicillin, kanamycin, among others. Use of lentiviral vectors is discussed in Wardill et al., 2013, A neuron-based screening platform for optimizing genetically-encoded calcium indicators, PLoS One 8(10):e77728; Dottori, et al., Neural development in human embryonic stem cells-applications of lentiviral vectors, J Cell Biochem 112(8):1955-62; and Diester et al., 2011, An optogenetic toolbox designed for primates, Nat Neurosci 14(3):387-97. When expressed under a CaMKIIα promoter in cultured rat hippocampal neurons the Optopatch construct exhibits high expression and good membrane trafficking of both CheRiff and QuasAr2.

In some embodiments the viral vector is an adeno-associated virus (AAV) vector. AAV can infect both dividing and non-dividing cells and may incorporate its genome into that of the host cell. One suitable viral vector uses recombinant adeno-associated virus (rAAV), which is widely used for gene delivery in the CNS.

In certain embodiments, methods of the invention use a Cre-dependent expression system. Cre-dependent expression includes Cre-Lox recombination, a site-specific recombinase technology that uses the enzyme Cre recombinase, which recombines a pair of short target sequences called the Lox sequences. This system can be implemented without inserting any extra supporting proteins or sequences. The Cre enzyme and the original Lox site called the LoxP sequence are derived from bacteriophage P1. Bacteriophage P1 uses Cre-lox recombination to circularize and replicate its genomic DNA. This recombination strategy is employed in Cre-Lox technology for genome manipulation, which requires only the Cre recombinase and LoxP sites. Sauer & Henderson, 1988, Site-specific DNA recombination in mammalian cells by the Cre recombinase of bacteriophage P1, PNAS 85:5166-70 and Sternberg & Hamilton, 1981, Bacteriophage P1 site-specific recombination. I. Recombination between LoxP sites, J Mol Biol 150:467-86. Methods may use a Cre recombinase-dependent viral vector for targeting tools such as channelrhodopsin-2 (ChR2) to specific neurons with expression levels sufficient to permit reliable photostimulation. Optogenetic tools such as ChR2 tagged with a fluorescent protein such as mCherry (e.g., ChR2mCherry) or any other of the tools discussed herein are thus delivered to the cell or cells for use in characterizing those cells.

The delivery vector may include Cre and Lox. The vector may further optionally include a Lox-stop-Lox (LSL) cassette to prevent expression of the transgene in the absence of Cre-mediated recombination. In the presence of Cre recombinase, the LoxP sites recombine, and a removable transcription termination Stop element is deleted. Removal of the stop element may be achieved through the use of AdenoCre, which allows control of the timing and location of expression. Use of the LSL cassette is discussed in Jackson, et al., 2001, Analysis of lung tumor initiation and progression using conditional expression of oncogenic K-ras, Genes & Dev 15:3243-3248.

In certain embodiments, a construct of the invention uses a "flip-excision" switch, or FLEX switch (FLip EXicision), to achieve stable transgene inversion. The FLEX switch is discussed in Schnutgen et al., 2003, A directional strategy for monitoring Cre-mediated recombination at the cellular level in the mouse, Nat Biotechnol 21:562-565. The FLEX switch uses two pairs of heterotypic, antiparallel LoxP-type recombination sites which first undergo an inversion of the coding sequence followed by excision of two sites, leading to one of each orthogonal recombination site oppositely oriented and incapable of further recombination. A FLEX switch provides high efficiency and irreversibility. Thus in some embodiments, methods use a viral vector comprising rAAV-FLEX-rev-ChR2mCherry. Additionally or alternatively, a vector may include FLEX and any other optogenetic tool discussed herein (e.g., rAAV-FLEX-QuasAr, rAAV- FLEX-CheRiff). Using rAAV-FLEX-rev-ChR2mCherry as an illustrative example, Cre-mediated inversion of the ChR2mCherry coding sequence results in the coding sequence being in the wrong orientation (i.e., rev-ChR2mCherry) for transcription until Cre inverts the sequence, turning on transcription of ChR2mCherry. FLEX switch vectors are discussed in Atasoy et al., 2009, A FLEX switch targets channelrhodopsin-2 to multiple cell types for imaging and long-range circuit mapping, J Neurosci 28(28): 7025-7030.

Use of a viral vector such as Cre-Lox system with an optical reporter, optical actuator, or both (optionally with a FLEX switch and/or a Lox-Stop-Lox cassette) for labeling and stimulation of neurons allows for efficient photo-stimulation with only brief exposure (1 ms) to less than 100 μW focused laser light or to light from an optical fiber. Such Further discussion may be found in Yizhar et al., 2011, Optogenetics in neural systems, Neuron 71(1):9-34; Cardin et al., 2010, Targeted optogenetic stimulation and recording of neurons in vivo using cell-type-specific expression of Channelrhodopsin-2, Nat Protoc 5(2):247-54; Rothermel et al., 2013, Transgene expression in target-defined neuron populations mediated by retrograde infection ith adeno-associated viral vectors, J Neurosci 33(38):195-206; and Saunders et al., 2012, Novel recombinant adeno-associated viruses for Cre activated and inactivated transgene expression in neurons, Front Neural Circuits 6:47.

In certain embodiments, actuators, reporters, or other genetic material may be delivered using chemically-modified mRNA. It may be found and exploited that certain nucleotide modifications interfere with interactions between mRNA and toll-like receptor, retinoid-inducible gene, or both. Exposure to mRNAs coding for the desired product may lead to a desired level of expression of the product in the cells. See, e.g., Kormann et al., 2011, Expression of therapeutic proteins after delivery of chemically modified mRNA in mice, Nat Biotech 29(2):154-7; Zangi et al., 2013, Modified mRNA directs the fate of heart protenitor cells and induces vascular regeneration after myocardial infarction, Nat Biotech 31:898-907.

It may be beneficial to culture or mature the cells after transformation with the genetically encoded optical reporter with optional actuator. In some embodiments, the neurons are matured for 8-10 days post infection. Using microscopy and analytical methods described herein, the cell and its action potentials may be observed. For additional discussion, see U.S. Pub. 2013/0224756, incorporated by reference in its entirety for all purposes.

4d. Optogenetic Constructs and Plating Schemes for Simultaneous Voltage and Ca2+ Measurement.

Figure 25:
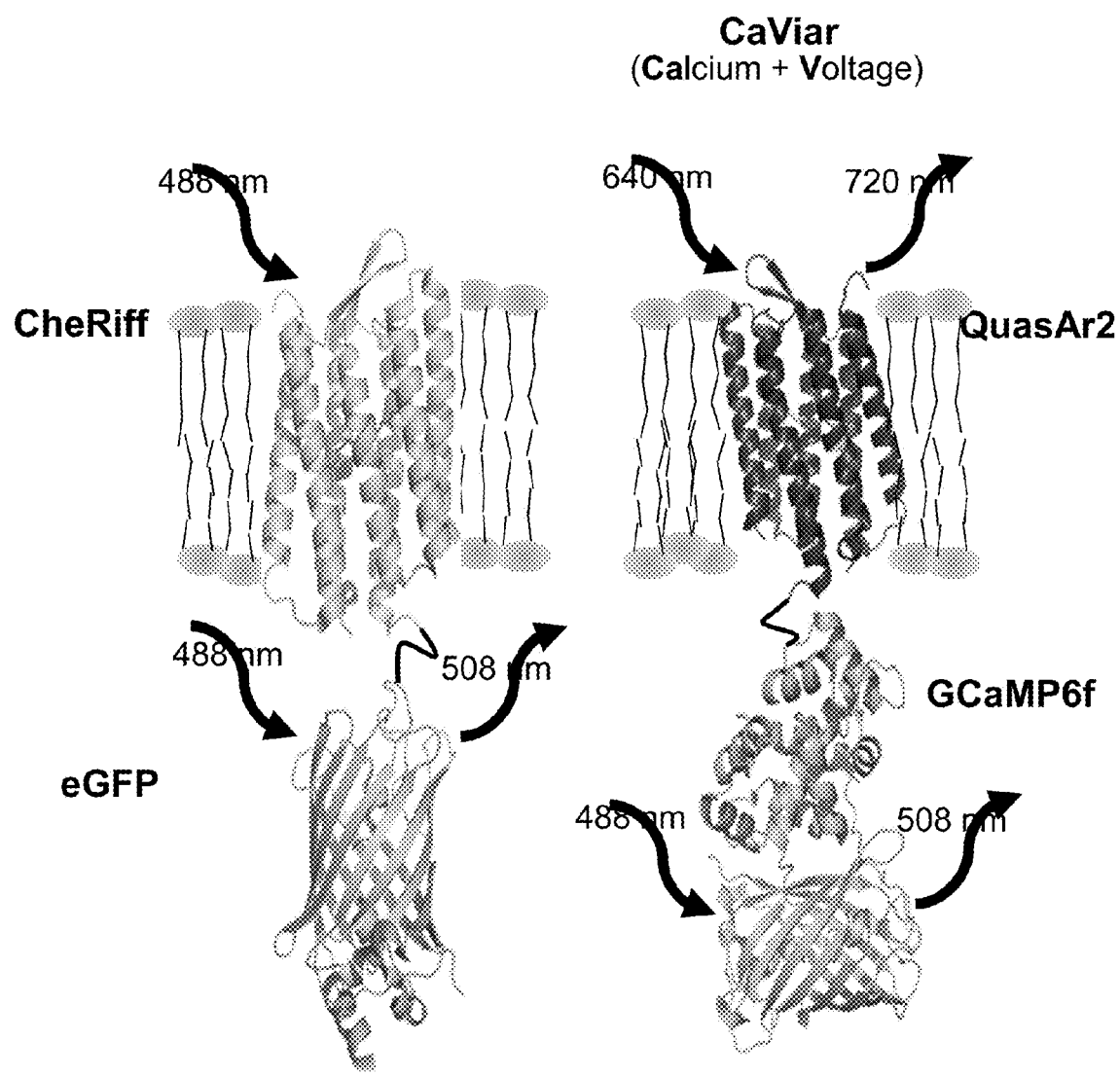
FIG. 25 shows optogenetic proteins used for stimulus and detection of voltage and intracellular Ca2+.

FIG. 25 presents schematic structures of optogenetic proteins used for stimulus and detection of voltage and intracellular Ca2+. The diagrams show proteins homologous to CheRiff and QuasAr2. Stimulus of cells is achieved through 488 nm LED illumination of CheRiff. The CheRiff construct is coupled to an eGFP tag for detection of CheRiff expression. A fusion protein called CaViar (Hou et al., 2014), consisting of QuasAr2 (Hochbaum et al., 2014) fused to GCaMP6f (Chen et al., 2013), is used for simultaneous voltage and Ca2+ imaging. QuasAr2 is excited via red laser light. GCaMP6f is excited via blue laser light. Cells are separately transduced with either CheRiff or CaViar vectors.

Figure 26:
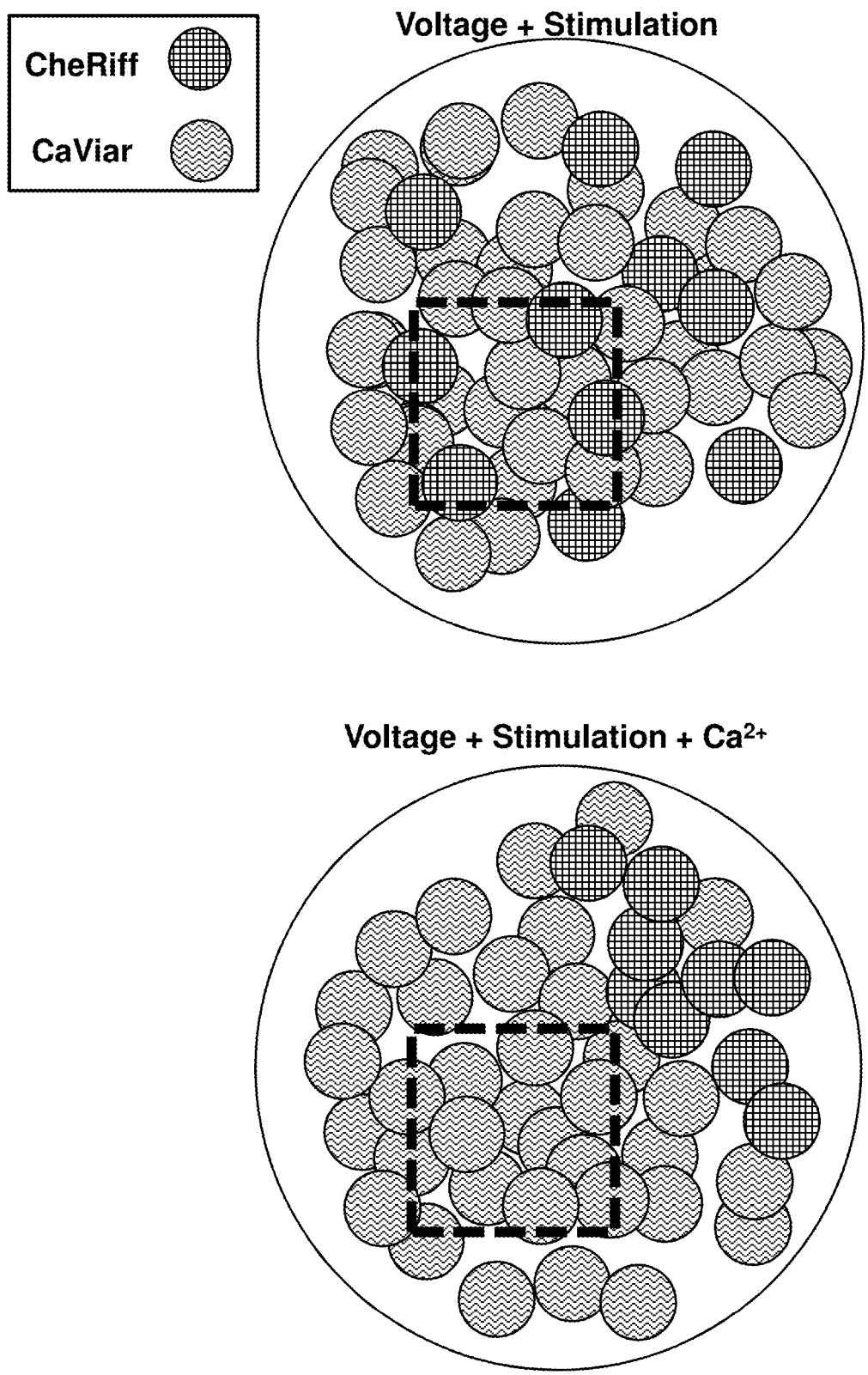
FIG. 26 illustrates cellular plating configurations.

FIG. 26 illustrates cellular plating configurations. For simultaneous optical stimulus and voltage imaging, CheRiff cells (solid cyan circles) are co-mingled with CaViar cells (solid red circles). The yellow dotted line indicates a microscope field of view. For simultaneous optical stimulus and imaging of both Ca2+ and membrane voltage, cells are plated to spatially segregate CheRiff-expressing cells from CaViar-expressing cells to avoid optical crosstalk between the pulsed blue light used to periodically stimulate the CheRiff-expressing cells and the continuous blue light used to image the CaViar-expressing cells. The CheRiff-expressing cells lay outside the imaging region.

When testing for optical crosstalk between Arch-based reporters and CheRiff in cultured cells, illumination sufficient to induce APs (488 nm, 140 mW/cm2) perturbed fluorescence of QuasAr reporters by <1%. Illumination with high intensity red light (640 nm, 900 W/cm2) induced an inward photocurrent through CheRiff of 14.3±3.1 pA, which depolarized cells by 3.1±0.2 mV (n=5 cells). ChIEF and ChR2 H134R generated similar red light photocurrents and depolarizations. For most applications this level of optical crosstalk is acceptable.

4e. Multimodal Sensing/Multiplexing

Membrane potential is only one of several mechanisms of signaling within cells. One may correlate changes in membrane potential with changes in concentration of other species, such as Ca2+, H+ (i.e. pH), Na+, ATP, cAMP, NADH. We constructed fusions of Arch with pHluorin (a fluorescent pH indicator) and GCaMP6f (a fluorescent Ca2+ indicator). The fusion of an Arch-based voltage indicator and a genetically encoded Ca2+ indicator is called CaViar (See Hou et al., 2014, Simultaneous mapping of membrane voltage and calcium in zebrafish heart in vivo reveals chamber-specific developmental transitions in ionic currents, Frontiers in physiology 5). One can also use fusions with other protein-based fluorescent indicators to enable other forms of multimodal imaging using the concept as taught herein. Concentration of ions such as sodium, potassium, chloride, and calcium can be simultaneously measured when the nucleic acid encoding the microbial rhodopsin is operably linked to or fused with an additional fluorescent analyte sensitive indicator; or when the microbial rhodopsin and the additional fluorescent analyte sensitive indicator are co-expressed in the same cell.

It is often desirable to achieve simultaneous optical stimulation of a cell, calcium imaging, and voltage imaging. To achieve all three modalities in the same cell, the invention provides for a violet-excited Channelrhodopsin actuator (psChR or TsChR); a red-shifted genetically encoded calcium indicator; and a far red Arch-derived voltage indicator. Red-shifted genetically encoded calcium indicators include R-GECO1 (See Zhao, Yongxin, et al. "An expanded palette of genetically encoded Ca2+ indicators." Science 333.6051 (2011): 1888-1891 and Wu, Jiahui, et al. "Improved orange and red Ca2+ indicators and photophysical considerations for optogenetic applications." ACS chemical neuroscience 4.6 (2013): 963-972, both incorporated by reference), R-CaMP2 (See Inoue, Masatoshi, et al. "Rational design of a high-affinity, fast, red calcium indicator R-CaMP2." Nature methods 12.1 (2015): 64-70, incorporated by reference), jRCaMP1a (Addgene plasmid 61562), and jRGECO1a (Addgene plasmid 61563). These calcium indicators are excited by wavelengths between 540 and 560 nm, and emit at wavelengths between 570 and 620 nm, thereby permitting spectral separation from the violet-excited channelrhodopsin actuator and the Arch-based voltage indicator.

One can combine imaging of voltage indicating proteins with other structural and functional imaging, of e.g. pH, calcium, or ATP. One may also combine imaging of voltage indicating proteins with optogenetic control of membrane potential using e.g. channelrhodopsin, halorhodopsin, and Archaerhodopsin. If optical measurement and control are combined, one can perform all-optical electrophysiology to probe the dynamic electrical response of any membrane.

The invention provides high-throughput methods of characterizing cells. Robotics and custom software may be used for screening large libraries or large numbers of conditions which are typically encountered in high throughput drug screening methods.

4f Optical Readout

Embodiments of the invention provide for spatial separation of stimulating cells and reporter cells. Expression of channelrhodopsin-based light-gated ion channels provides a means to achieve optical stimulus. However, the blue light used to activate these channels may overlap spectrally with the light used to image most small-molecule and genetically encoded fluorescent reporters of physiological activity (e.g. gCaMP Ca2+ indicators, Percival ATP indicators, pHluorin pH indicators, VF2.1.C1 voltage-sensitive dyes). Also, the light used to image these reporters may lead to off-target activation of all known channelrhodopsin actuators. Ideally, one would like to optically stimulate a cell culture while maintaining freedom to record from fluorescent reporters of any color, without optical crosstalk between the stimulus and the physiological measurement. Methods of the invention allow a cellular culture to be optically stimulated while also using fluorescent reporters of any color, without optical crosstalk between the stimulus and the physiological measurement through the spatial separation of actuator cells and reporter cells.

One solution presented here comprises expressing channelrhodopsin actuators in one set of hiPSC-derived cells, and expressing reporters (e.g. CaViar dual-function Ca2+ and voltage reporter) in another set of cells. Flashes of blue light are delivered to the actuator cells, while continuous blue light is used to monitor the reporter cells. The actuator cells stimulate the reporter cells through synapses. A key challenge is to identify and target the stimulus and the measurement light beams to the appropriate corresponding cells. Methods of the invention provide at least two embodiments of the solution to the problem of targeting separate stimulus and measurement light beams to the appropriate cells: a first approach based on spatial segregation and a second approach based on image processing and patterned illumination.

4g. Spatial Segregation

In a first embodiment using spatial segregation, light is targeted to the actuator cells using spatial segregation of actuator and reporter-expressing cells.

Cells are independently infected with actuator and reporter and are re-plated in distinct but electrically contiguous regions. Optical stimulus is delivered only to regions of the dish with cells expressing the actuator, and sensor measurements using any wavelength of light are recorded in regions of the dish away from cells expressing the actuator. In one instance, the actuator is CheRiff, and the sensor is CaViar in human iPSC-derived neurons.

Figure 27:
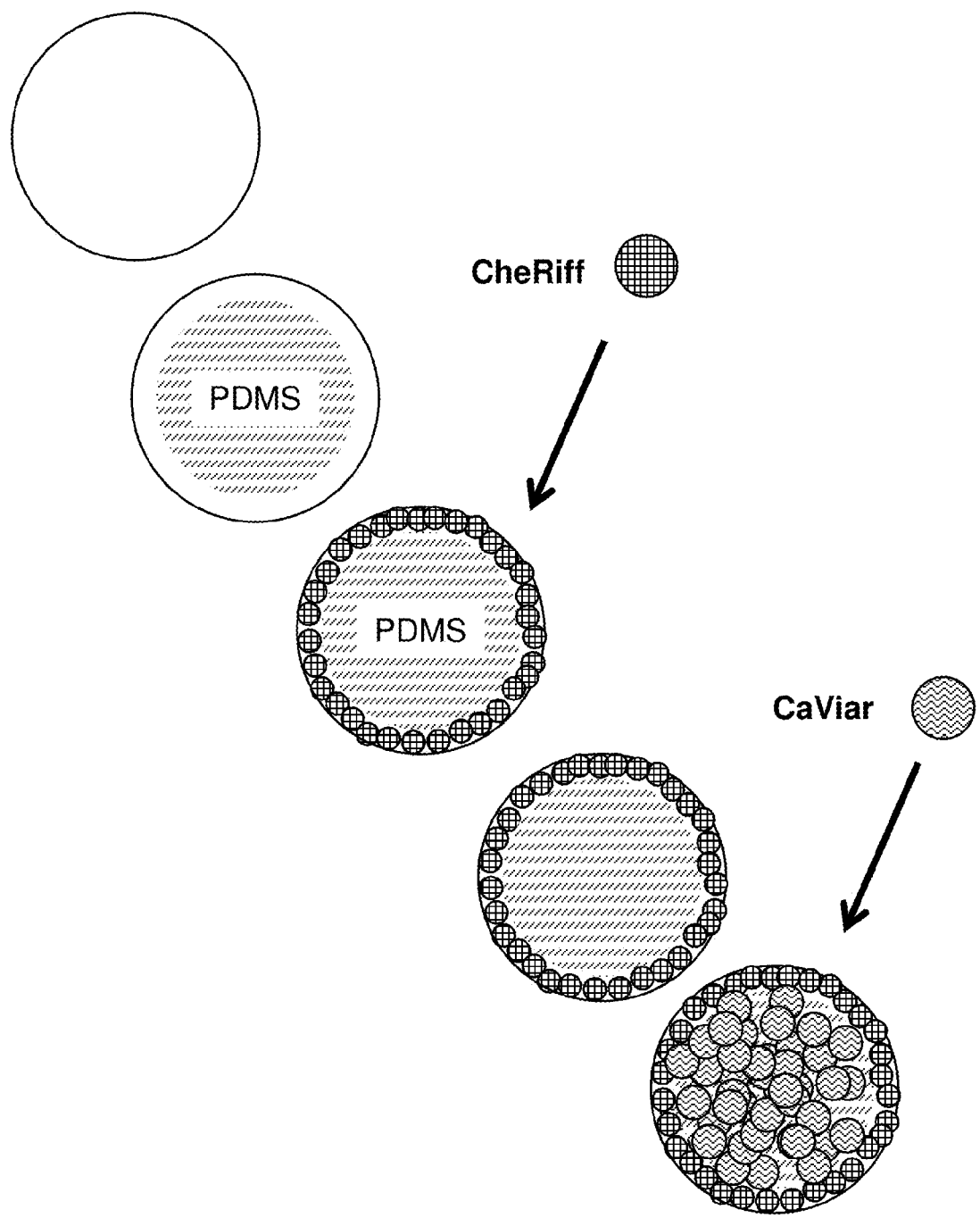
FIG. 27 shows cells expressing CheRiff plated in an annular region.

FIG. 27 shows cells expressing CheRiff plated in an annular region, 10 mm outer diameter, ~8 mm diameter. The inner radius is set by a disk of polydimethyl siloxane (PDMS) adhered to the coverslip and the outer diameter is set by the edge of the chamber. The PDMS disk is then removed and cells expressing CaViar are plated throughout. Stimulus is controlled by a blue LED whose illumination is confined to a small region of the actuating cells. Voltage and calcium imaging are achieved with a red and blue laser, respectively, in a region free of CheRiff-expressing cells.

4h. Patterned Illumination

In a second embodiment using patterned illumination, light is targeted to the actuator cells using image processing and patterned illumination to separately target intermingled actuator- and reporter-expressing cells.

For image processing and patterned illumination, cells expressing either actuator or reporters are randomly intermixed. In one embodiment, cells are initially plated separately and caused to express either the actuator or the reporter. The cells are then lifted from their respective dishes, mixed, and co-plated onto the imaging dish. In another embodiment, cells are plated directly in the imaging chamber, and doubly infected with lentivirus encoding Cre-On actuator and a Cre-Off reporter. The cells are then infected sparsely with lentivirus encoding the Cre protein, so that in a sparse subset of cells the actuator is switched on and the reporter is switched off.

Cells expressing the actuator are identified via a recognizable marker, e.g. a fluorescent protein, or by their absence of fluorescence transients indicating presence of a reporter. Optical stimulus is achieved by spatially patterning the excitation light using a digital micromirror device (DMD) to project flashes onto only those cells expressing the actuator.

Figure 5:
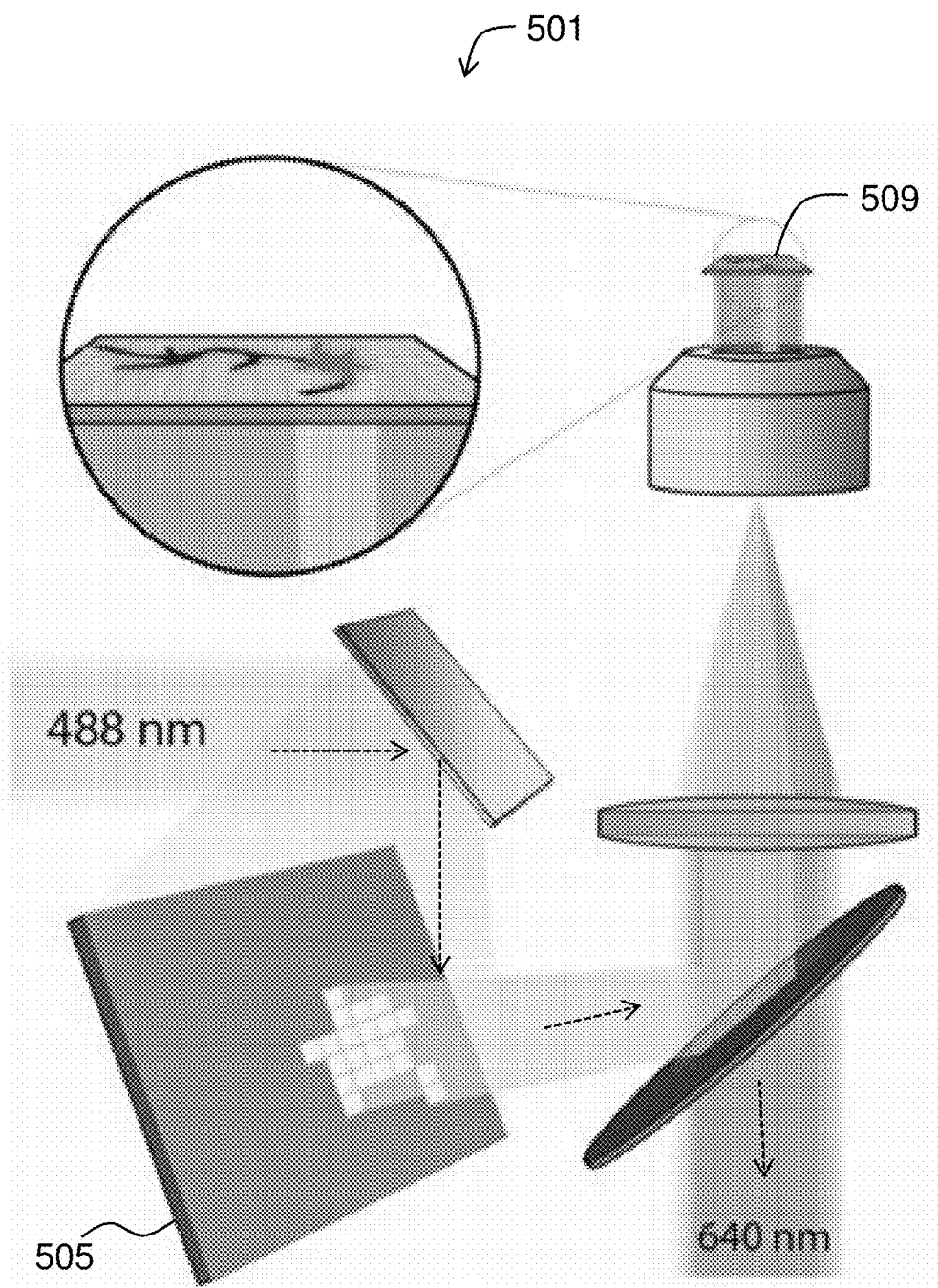
FIG. 5 diagrams components of an optical imaging apparatus.

FIG. 5 diagrams an optical imaging apparatus 501 for patterned illumination. A 488 nm blue laser beam is modulated in intensity by an acousto-optic modulator (not shown), and then reflected off a digital micromirror device (DMD) 505. The DMD imparted a spatial pattern on the blue laser beam (used for CheRiff excitation) on its way into the microscope. The micromirrors are re-imaged onto the sample 509, leading to an arbitrary user-defined spatiotemporal pattern of illumination at the sample. Simultaneous whole-field illumination with 640 nm red light excites fluorescence of the reporter.

The fluorescent protein serving as a recognizable marker of the cells expressing the actuator is imaged to determine a pattern of those actuator cells. The digital coordinates of that image are used to control the DMD 505 so that the DMD 505 directs the blue 488 nm light only onto the actuator cells. Due to the precision of the patterned illumination provided by the DMD 505, the cells expressing the reporter are not exposed to the 488 nm light. Cells expressing the reporter are imaged under continuous illumination, with the 640 nm light targeted via the DMD to illuminate only those cells expressing the reporter, and optionally continuous illumination at a wavelength of 488 nm to illuminate an additional reporter such as a GCaMP calcium indicator.

By the patterned illumination method, flashes of blue light are delivered to the actuator cells, while continuous red and/or blue light is used to monitor the reporter cells. The actuator cells stimulate the reporter cells (e.g., across synapses). Preferably, the actuator cells comprise a first set of hiPSC-derived neurons expressing channelrhodopsin actuators and the reporter cells comprise a second set of hiPSC-derived neurons expressing reporters (e.g. QuasAr2 or CaViar dual-function Ca2+ and voltage reporter).

The foregoing (i) spatial segregation and (ii) patterned illumination methods provide for optical detection of changes in membrane potential, [Ca2+], or both, in optically stimulated neurons. The described methods and techniques herein provide for the optical detection of the effects of compounds on cells such as cells with disease genotypes. Such detection allows for evaluating the effect of a compound or other stimulus on the phenotype of such cells.

4i. Preparation of Plates for Voltage Imaging

MatTek dishes (MatTek corp.; 10 mm glass diameter, #1.5) are coated with 10 µg/mL fibronectin (Sigma-Aldrich)

in 0.1% gelatin overnight at 4° C. Trypsinized CaViar and CheRiff-expressing cells are first mixed at a ratio of 5:1 CaViar:CheRiff, and then pelleted. The combined cells are re-suspended in 2.1 mL of maintenance medium and plated at a density of $2.5 \times 10^4$ cells/cm2 in 100 µL of plating medium to cover the entire glass surface. Cells are kept at 37° C. in 5% CO2 overnight to adhere to the glass. Maintenance medium (1.0 mL) is added to each dish and the cells are fed every 48 hours by removing 750 µL of medium from the dish and replacing with 750 µL fresh maintenance medium.

4j. Preparation of Plates for Simultaneous Voltage and Calcium Imaging

For simultaneous voltage and calcium imaging, MatTek dishes (10 mm glass diameter) are prepared to segregate CheRiff-expressing cells from CaViar-expressing cells. This allows simultaneous calcium imaging and CheRiff stimulus, both with blue light, without optical crosstalk between the two functions. In certain embodiments, 8 mm-diameter poly-dimethylsiloxane (PDMS) discs are treated with a solution of 10 µg/mL fibronectin in 0.1% gelatin on one side for 10 minutes at room temperature. The coated discs are then dried and then pressed onto the MatTek dish glass surface, slightly offset to one side. The remaining exposed area of the glass is then coated with 10 µg/mL fibronectin in 0.1% gelatin. Cells expressing the CheRiff are trypsinized according to the manufacturer's protocol and re-suspended in 50 µL of maintenance medium per dish. For plating, 50 µL of the CheRiff cells are then added to the exposed portion of the glass surface and allowed to sit for 40 minutes at 37° C. in 5% CO2 to allow the cells to adhere. The PDMS discs are then removed, the glass surface washed with 150 µL of maintenance media medium and the remaining volume aspirated. Trypsinized CaViar cells are then re-suspended in 100 µL of maintenance medium per dish and plated at a density of $2.0 \times 10^4$ cells/cm2 in 100 µL to cover the entire glass surface. Cells are kept at 37° C. in 5% CO2 overnight to adhere to the glass. 1.0 0 mL of maintenance medium is added to each dish and the cells are fed every 48 hours by removing 750 µL of media from the dish and adding 750 µL fresh maintenance medium.

5. Imaging Activity Assay

5a. Capturing Images

Methods of the invention may include stimulating the cells that are to be observed. Stimulation may be direct or indirect (e.g., optical stimulation of an optical actuator or stimulating an upstream cell in synaptic communication with the cell(s) to be observed). Stimulation may be optical, electrical, chemical, or by any other suitable method. Stimulation may involve any pattern of a stimulation including, for example, regular, periodic pulses, single pulses, irregular patterns, or any suitable pattern. Methods may include varying optical stimulation patterns in space or time to highlight particular aspects of cellular function. For example, a pulse pattern may have an increasing frequency. In certain embodiments, imaging includes stimulating a neuron that expresses an optical actuator using pulses of light.

A neuron expressing an Optopatch construct may be exposed to whole-field illumination with pulses of blue light (10 ms, 25 mW/cm) to stimulate CheRiff, and simultaneous constant illumination with red light (800 W/cm) to excite fluorescence of QuasAr2. The fluorescence of QuasAr2 may be imaged at a 1 kHz frame rate. Key parameters include temporal precision with which single spikes can be elicited and recorded, signal-to-noise ratio (SNR) in fluorescence traces, and long-term stability of the reporter signal. Methods provided herein may be found to optimize those parameters. Further discussion may be found in Foust et al., 2010, Action potentials initiate in the axon initial segment and propagate through axon collaterals reliably in cerebellar Purkinje neurons, J. Neurosci 30:6891-6902; and Popovic et al., 2011, The spatio-temporal characteristics of action potential initiation in layer 5 pyramidal neurons: a voltage imaging study, J. Physiol. 589:4167-4187.

In some embodiments, measurements are made using a low-magnification microscope that images a 1.2×3.3 mm field of view with 3 µm spatial resolution and 2 ms temporal resolution. In other embodiments, measurements are made using a high-magnification microscope that images a 100 µm field of view with 0.8 µm spatial resolution and 1 ms temporal resolution. A suitable instrument is an inverted fluorescence microscope, similar to the one described in the Supplementary Material to Kralj et al., 2012, Optical recording of action potentials in mammalian neurons using a microbial rhodopsin, Nat. Methods 9:90-95. Briefly, illumination from a red laser 640 nm, 140 mW (Coherent Obis 637-140 LX), is expanded and focused onto the back-focal plane of a 60× oil immersion objective, numerical aperture 1.45 (Olympus 1-U2B616).

FIG. 5 gives a functional diagram of components of an optical imaging apparatus 501 according to certain embodiments. A 488 nm blue laser beam is modulated in intensity by an acousto-optic modulator (not shown), and then reflected off a digital micromirror device (DMD) 505. The DMD imparted a spatial pattern on the blue laser beam (used for CheRiff excitation) on its way into the microscope. The micromirrors were re-imaged onto the sample 509, leading to an arbitrary user-defined spatiotemporal pattern of illumination at the sample. Simultaneous whole-field illumination with 640 nm red light excites fluorescence of the QuasAr reporter.

With the inverted fluorescence microscope, illumination from a blue laser 488 nm 50 mW (Omicron PhoxX) is sent through an acousto-optic modulator (AOM; Gooch and Housego 48058-2.5-.55-5W) for rapid control over the blue intensity. The beam is then expanded and modulated by DMD 505 with 608×684 pixels (Texas Instruments LightCrafter). The DMD is controlled via custom software (Matlab) through a TCP/IP protocol. The DMD chip is re-imaged through the objective onto the sample, with the blue and red beams merging via a dichroic mirror. Each pixel of the DMD corresponds to 0.65 µm in the sample plane. A 532 nm laser is combined with the red and blue beams for imaging of mOrange2. Software is written to map DMD coordinates to camera coordinates, enabling precise optical targeting of any point in the sample.

To achieve precise optical stimulation of user-defined regions of a neuron, pixels on DMD 505 are mapped to pixels on the camera. The DMD projects an array of dots of known dimensions onto the sample. The camera acquires an image of the fluorescence. Custom software locates the centers of the dots in the image, and creates an affine transformation to map DMD coordinates onto camera pixel coordinates.

A dual-band dichroic filter (Chroma zt532/635rpc) separates reporter (e.g., Arch) from excitation light. A 531/40 nm bandpass filter (Semrock FF01-531/40-25) may be used for eGFP imaging; a 710/100 nm bandpass filter (Chroma, HHQ710/100) for Arch imaging; and a quad-band emission filter (Chroma ZET405/488/532/642m) for mOrange2 imaging and pre-measurement calibrations. A variable-zoom camera lens (Sigma 18-200 mm f/3.5-6.3 II DC) is used to image the sample onto an EMCCD camera (Andor iXon+

DU-860), with 128×128 pixels. Images may be first acquired at full resolution (128×128 pixels). Data is then acquired with 2×2 pixel binning to achieve a frame rate of 1,000 frames/s. For runs with infrequent stimulation (once every 5 s), the red illumination is only on from 1 s before stimulation to 50 ms after stimulation to minimize photobleaching. Cumulative red light exposure may be limited to <5 min. per neuron.

Low magnification wide-field imaging is performed with a custom microscope system based around a 2x, NA 0.5 objective (Olympus MVX-2). Illumination is provided by six lasers 640 nm, 500 mW (Dragon Lasers 635M500), combined in three groups of two. Illumination is coupled into the sample using a custom fused silica prism, without passing through the objective. Fluorescence is collected by the objective, passed through an emission filter, and imaged onto a scientific CMOS camera (Hamamatsu Orca Flash 4.0). Blue illumination for channelrhodopsin stimulation is provided by a 473 nm, 1 W laser (Dragon Lasers), modulated in intensity by an AOM and spatially by a DMD (Digital Light Innovations DLi4130-ALP HS). The DMD is re-imaged onto the sample via the 2x objective. During a run, neurons may be imaged using wide-field illumination at 488 nm and eGFP fluorescence. A user may select regions of interest on the image of the neuron, and specify a time course for the illumination in each region. The software maps the user-selected pixels onto DMD coordinates and delivers the illumination instructions to the DMD.

The inverted fluorescence micro-imaging system records optically from numerous (e.g., 50) expressing cells or cell clusters in a single field of view. The system may be used to characterize optically evoked firing patterns and AP waveforms in neurons expressing an Optopatch construct. Each field of view is exposed to whole-field pulses of blue light to evoke activity (e.g., 0.5 s, repeated every 6 s, nine intensities increasing from 0 to 10 mW/cm). Reporter fluorescence such as from QuasAr may be simultaneously monitored with whole-field excitation at 640 nm, 100 W/cm.

Figure 6:
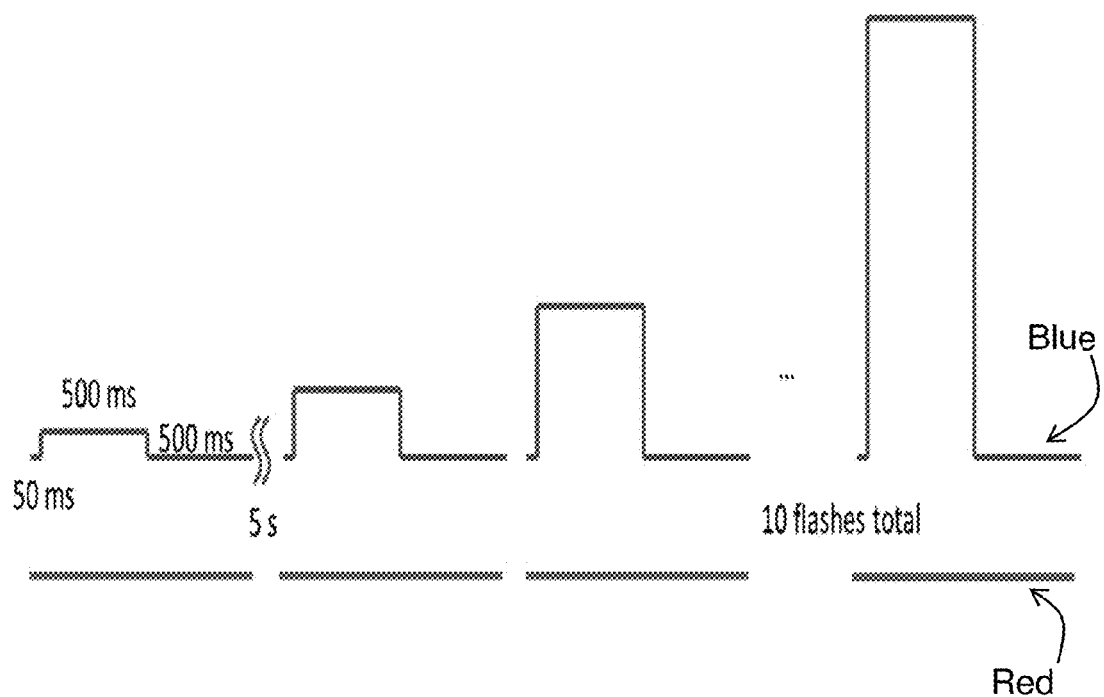
FIG. 6 illustrates the use of pulse sequences to record action potentials.

FIG. 6 illustrates a pulse sequence of red and blue light used to record action potentials under increasing optical stimulation. In some embodiments, neurons are imaged on a high resolution microscope with 640 nm laser (600 W/cm) for voltage imaging. In certain embodiments, neurons are imaged on a high resolution microscope with 640 nm laser (600 W/cm) for voltage imaging and excited with a 488 nm laser (20-200 mW/cm). Distinct firing patterns can be observed (e.g., fast adapting and slow-adapting spike trains). System measurements can detect rare electrophysiological phenotypes that might be missed in a manual patch clamp measurement. Specifically, the cells' response to stimulation (e.g., optical actuation) may be observed. Instruments suitable for use or modification for use with methods of the invention are discussed in U.S. Pub. 2013/0170026 to Cohen, incorporated by reference.

Using the described methods, populations of cells may be measured. For example, both diseased and corrected (e.g., by zinc finger domains) motor neurons may be measured. A cell's characteristic signature such as a neural response as revealed by a spike train may be observed.

5b. Extracting Fluorescence from Movies

Fluorescence values are extracted from raw movies by any suitable method. One method uses the maximum likelihood pixel weighting algorithm described in Kralj et al., 2012, Optical recording of action potentials in mammalian neurons using a microbial rhodopsin, Nat Methods 9:90-95. Briefly, the fluorescence at each pixel is correlated with the whole-field average fluorescence. Pixels that showed stronger correlation to the mean are preferentially weighted. This algorithm automatically finds the pixels carrying the most information, and de-emphasizes background pixels.

In movies containing multiple cells, fluorescence from each cell is extracted via methods known in the art such as Mukamel, Eran A., Axel Nimmerjahn, and Mark J. Schnitzer. "Automated analysis of cellular signals from large-scale calcium imaging data." Neuron 63.6 (2009): 747-760, or Maruyama, Ryuichi, et al. "Detecting cells using non-negative matrix factorization on calcium imaging data." Neural Networks 55 (2014): 11-19. These methods use the spatial and temporal correlation properties of action potential firing events to identify clusters of pixels whose intensities co-vary, and associate such clusters with individual cells.

Alternatively, a user defines a region comprising the cell body and adjacent neurites, and calculates fluorescence from the unweighted mean of pixel values within this region. With the improved trafficking of the QuasAr mutants compared to Arch, these two approaches give similar results. In low-magnification images, direct averaging and the maximum likelihood pixel weighting approaches may be found to provide optimum signal-to-noise ratios.

6. Signal Processing

6a. Signal Processing with Independent Component Analysis to Associate Signals with Cells An image or movie may contain multiple cells in any given field of view, frame, or image. In images containing multiple neurons, the segmentation is performed semi-automatically using an independent components analysis (ICA) based approach modified from that of Mukamel, et al., 2009, Automated analysis of cellular signals from large-scale calcium imaging data, Neuron 63:747-760. The ICA analysis can isolate the image signal of an individual cell from within an image.

FIG. 7-FIG. 10 illustrate the isolation of individual cells in a field of view. Individual cells are isolated in a field of view using an independent component analysis.

Figure 7:
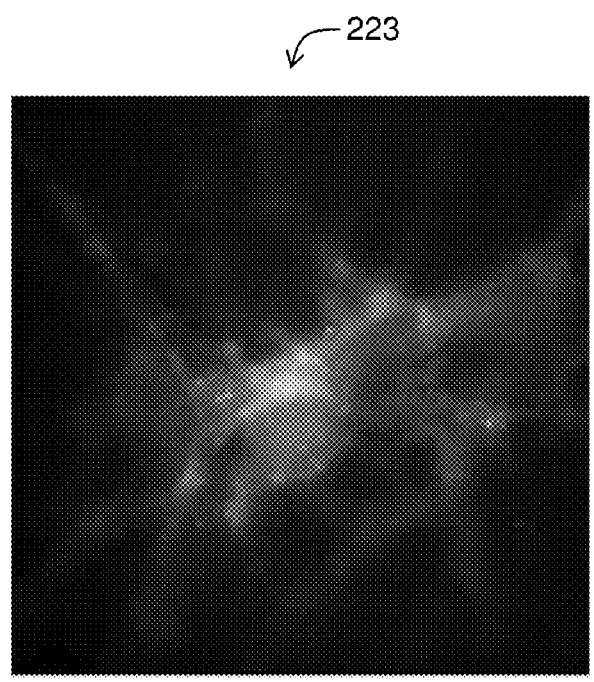
FIG. 7 is an image of cells from which an individual is to be isolated.

FIG. 7 shows an image that contains five neurons whose images overlap with each other. The fluorescence signal at each pixel is an admixture of the signals from each of the neurons underlying that pixel.

Figure 8:
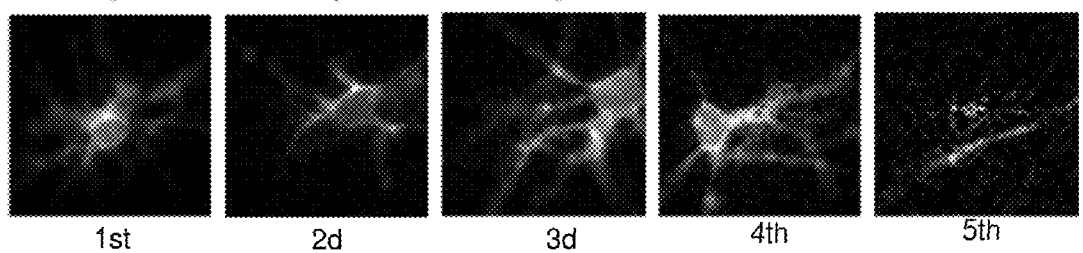
FIG. 8 illustrates the isolation of individual cells in a field of view.

As shown in FIG. 8, the statistical technique of independent components analysis finds clusters of pixels whose intensity is correlated within a cluster, and maximally statistically independent between clusters. These clusters correspond to images of individual cells comprising the aggregate image of FIG. 7.

From the pseudo-inverse of the set of images shown in FIG. 8 are calculated spatial filters with which to extract the fluorescence intensity time-traces for each cell. Filters are created by setting all pixel weights to zero, except for those in one of the image segments. These pixels are assigned the same weight they had in the original ICA spatial filter.

Figure 9:
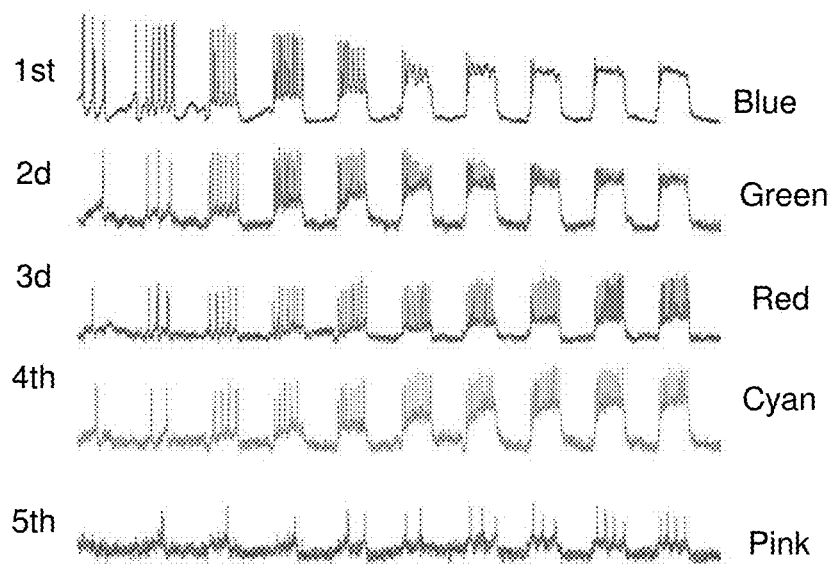
FIG. 9 shows the spike trains associated with individual cells.

In FIG. 9, by applying the segmented spatial filters to the movie data, the ICA time course has been broken into distinct contributions from each cell. Segmentation may reveal that the activities of the cells are strongly correlated, as expected for cells found together by ICA. In this case, the spike trains from the image segments are similar but show a progress over time as the cells signal one another.

Figure 10:
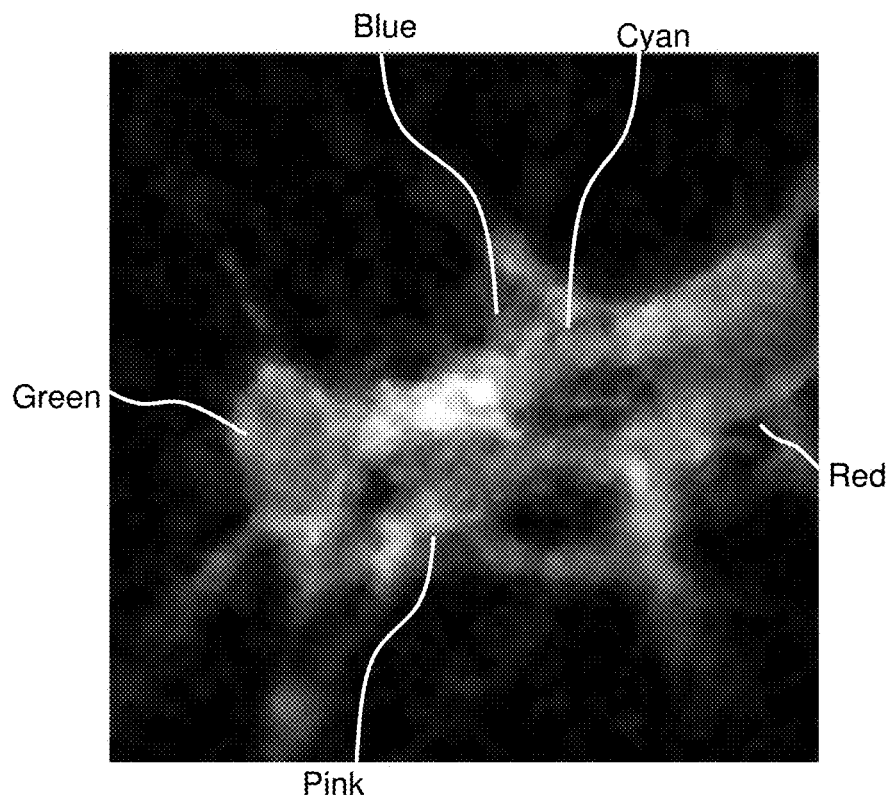
FIG. 10 shows individual cells in a cluster color-coded after isolation.

FIG. 10 shows the individual filters used to map (and color code) individual cells from the original image.

6b. Signal Processing Via Sub-Nyquist Action Potential Timing (SNAPT)

For individual cells, action potentials can be identified as spike trains represented by the timing at which an interpolated action potential crosses a threshold at each pixel in the image. Identifying the spike train may be aided by first processing the data to remove noise, normalize signals, improve SNR, other pre-processing steps, or combinations thereof. Action potential signals may first be processed by removing photobleaching, subtracting a median filtered trace, and isolating data above a noise threshold. The spike train may then be identified using an algorithm based on sub-Nyquist action potential timing such as an algorithm based on the interpolation approach of Foust, et al., 2010, Action potentials initiate in the axon initial segment and propagate through axon collaterals reliably in cerebellar Purkinje neurons. J. Neurosci 30, 6891-6902 and Popovic et al, 2011, The spatio-temporal characteristics of action potential initiation in layer 5 pyramidal neurons: a voltage imaging study. J. Physiol. 589, 4167-4187.

A sub-Nyquist action potential timing (SNAPT) algorithm highlights subcellular timing differences in AP initiation. For example, the algorithm may be applied for neurons expressing Optopatch1, containing a voltage reporter such as QuasAr1. Either the soma or a small dendritic region is stimulated. The timing and location of the ensuing APs is monitored.

Figure 11:
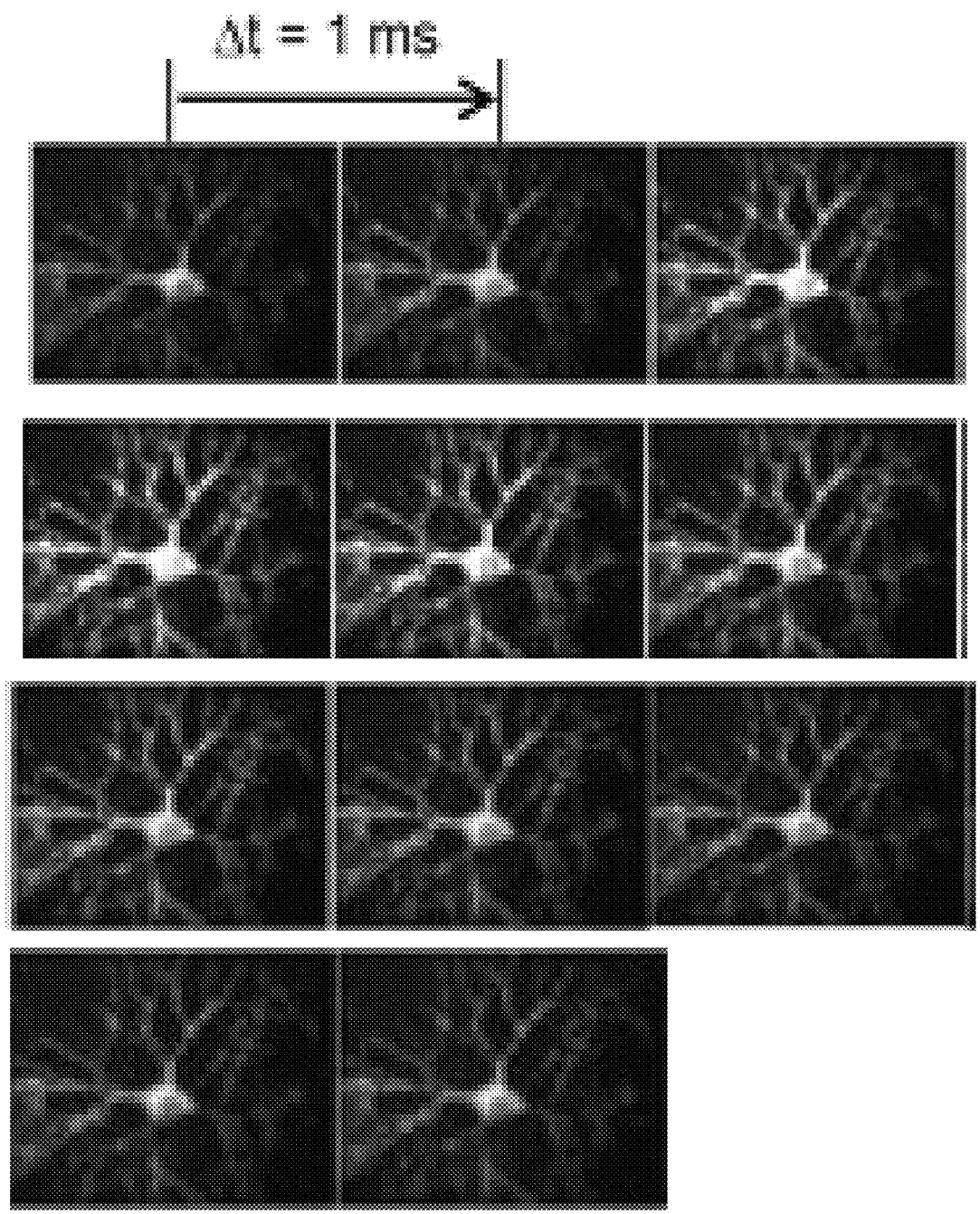
FIG. 11 shows optical excitation being used to induce action potentials.

FIG. 11 shows a patterned optical excitation being used to induce action potentials. Movies of individual action potentials are acquired (e.g., at 1,000 frames/s), temporally registered, and averaged.

The first step in the temporal registration of spike movies is to determine the spike times. Determination of spike times is performed iteratively. A simple threshold-and-maximum procedure is applied to F(t) to determine approximate spike times, {T0}. Waveforms in a brief window bracketing each spike are averaged together to produce a preliminary spike kernel K0(t). A cross-correlation of K0(t) with the original intensity trace F(t) is calculated. Whereas the timing of maxima in F(t) is subject to errors from single-frame noise, the peaks in the cross-correlation, located at times {T}, are a robust measure of spike timing. A movie showing the mean AP propagation may be constructed by averaging movies in brief windows bracketing spike times {T}. Typically 100-300 APs are included in this average. The AP movie has high signal-to-noise ratio. A reference movie of an action potential is thus created by averaging the temporally registered movies (e.g., hundreds of movies) of single APs. Each frame of the movie is then corrected by dividing by this baseline.

Spatial and temporal linear filters may further decrease the noise in AP movie. A spatial filter may include convolution with a Gaussian kernel, typically with a standard deviation of 1 pixel. A temporal filter may be based upon Principal Components Analysis (PCA) of the set of single-pixel time traces. The time trace at each pixel is expressed in the basis of PCA eigenvectors. Typically the first 5 eigenvectors are sufficient to account for >99% of the pixel-to-pixel variability in AP waveforms, and thus the PCA Eigen-decomposition is truncated after 5 terms. The remaining eigenvectors represented uncorrelated shot noise.

FIG. 12 shows eigenvectors resulting from a principal component analysis (PCA) smoothing operation performed to address noise. Photobleaching or other such non-specific background fluorescence may be addressed by these means.

FIG. 13 shows a relation between cumulative variance and eigenvector number. FIG. 14 gives a comparison of action potential waveforms before and after the spatial and PCA smoothing operations.

A smoothly varying spline function may be interpolated between the discretely sampled fluorescence measurements at each pixel in this smoothed reference AP movie. The timing at each pixel with which the interpolated AP crosses a user-selected threshold may be inferred with sub-exposure precision. The user sets a threshold depolarization to track (represented as a fraction of the maximum fluorescence transient), and a sign for dV/dt (indicating rising or falling edge. The filtered data is fit with a quadratic spline interpolation and the time of threshold crossing is calculated for each pixel.

Figure 15:
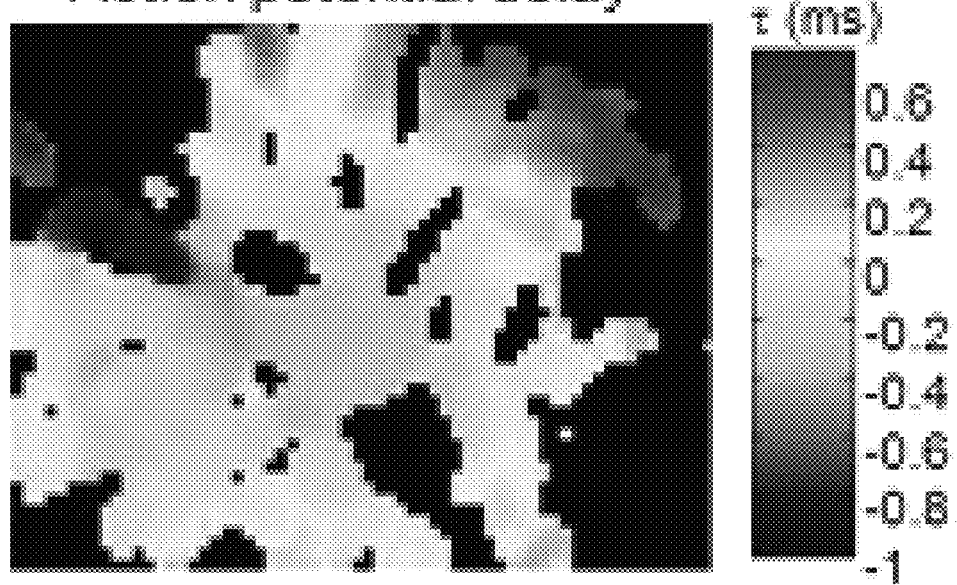
FIG. 15 shows an action potential timing map.

FIG. 15 shows an action potential timing map. The timing map may be converted into a high temporal resolution SNAPT movie by highlighting each pixel in a Gaussian time course centered on the local AP timing. The SNAPT fits are converted into movies showing AP propagation as follows. Each pixel is kept dark except for a brief flash timed to coincide with the timing of the user-selected AP feature at that pixel. The flash followed a Gaussian time-course, with amplitude equal to the local AP amplitude, and duration equal to the cell-average time resolution, σ. Frame times in the SNAPT movies are selected to be ~2-fold shorter than a. Converting the timing map into a SNAPT movie is for visualization; propagation information is in the timing map.

Figure 16:
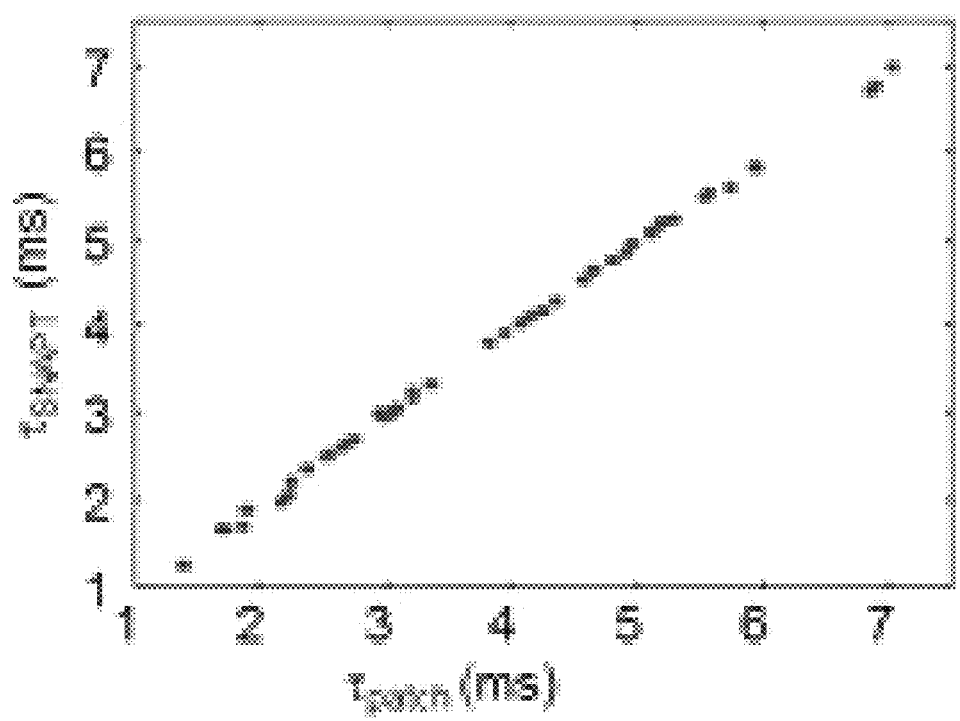
FIG. 16 shows the accuracy of timing extracted by methods of the invention.
Figure 17:
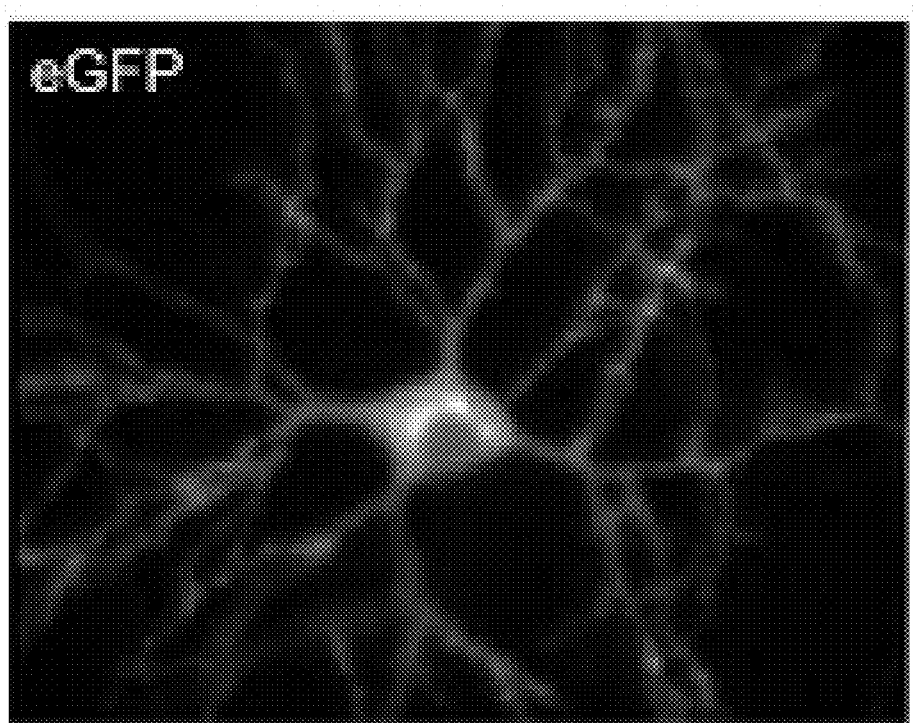
FIG. 17 gives an image of fluorescence distribution of an optical actuator.

FIG. 16 shows the accuracy of timing extracted by the SNAPT algorithm for voltage at a soma via comparison to a simultaneous patch clamp recording. FIG. 17 gives an image of eGFP fluorescence, indicating CheRiff distribution.

Figure 18:
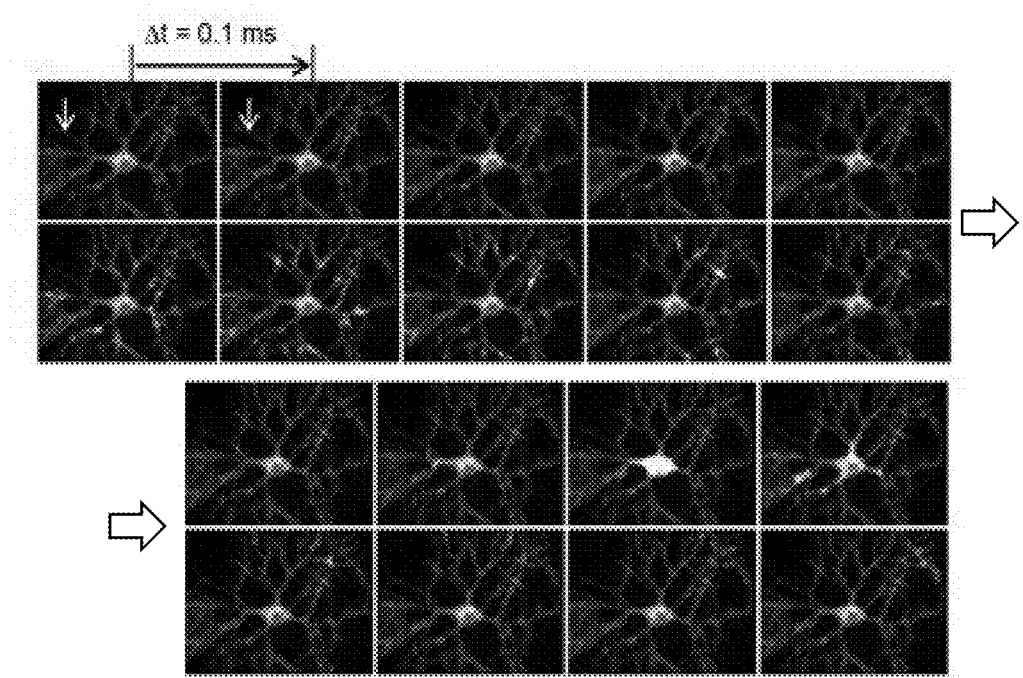
FIG. 18 presents frames from a SNAPT movie.

FIG. 18 presents frames from a SNAPT movie formed by mapping the timing information from FIG. 16 onto a high spatial resolution image from FIG. 17. In FIG. 17, the white arrows mark the zone of action potential initiation in the presumed axon initial segment (AIS). FIGS. 16-18 demonstrate that methods of the invention can provide high resolution spatial and temporal signatures of cells expressing an optical reporter of neural activity.

After acquiring Optopatch data, cells may be fixed and stained for ankyrin-G, a marker of the AIS. Correlation of the SNAPT movies with the immunostaining images establish that the AP initiated at the distal end of the AIS. The SNAPT technique does not rely on an assumed AP waveform; it is compatible with APs that change shape within or between cells.

The SNAPT movies show AP initiation from the soma in single neurites in measured cells. The described methods are useful to reveal latencies between AP initiation at the AIS and arrival in the soma of 320±220 μs, where AP timing is measured at 50% maximum depolarization on the rising edge. Thus Optopatch can resolve functionally significant subcellular details of AP propagation. Discussion of signal processing may be found in Mattis et al., 2011, Principles for applying optogenetic tools derived from direct comparative analysis of microbial opsins, Nat. Meth. 9:159-172; and Mukamel et al., 2009, Automated analysis of cellular signals from large-scale calcium imaging data, Neuron 63(6):747-760.

Methods of the invention are used to obtain a signature from the observed cell or cells tending to characterize a physiological parameter of the cell. The measured signature can include any suitable electrophysiology parameter such as, for example, activity at baseline, activity under different stimulus strengths, tonic vs. phasic firing patterns, changes in AP waveform, others, or a combination thereof. Measurements can include different modalities, stimulation protocols, or analysis protocols. Exemplarily modalities for measurement include voltage, calcium, ATP, or combinations thereof. Exemplary stimulation protocols can be employed to measure excitability, to measure synaptic transmission, to test the response to modulatory chemicals, others, and combinations thereof. Methods of invention may employ various analysis protocols to measure: spike frequency under different stimulus types, action potential waveform, spiking patterns, resting potential, spike peak amplitude, others, or combinations thereof.

In certain embodiments, the imaging methods are applied to obtain a signature mean probability of spike for cells from the patient and may also be used to obtain a signature from a control line of cells such as a wild-type control (which may be produced by genome editing as described above so that the control and the wild-type are isogenic but for a single site). The observed signature can be compared to a control signature and a difference between the observed signature and the expected signature corresponds to a positive diagnosis of the condition.

Figure 19:
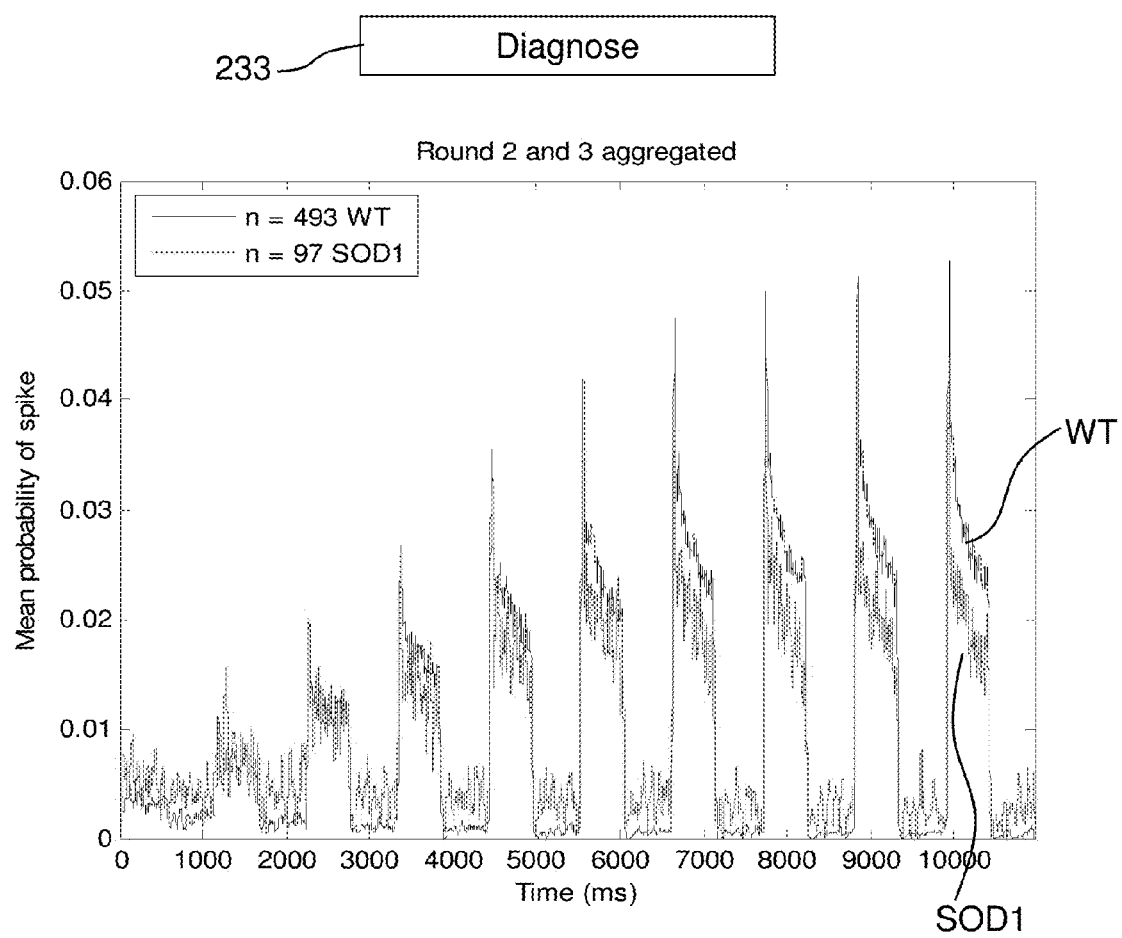
FIG. 19 compares spike probability of wild-type and mutant cells.

FIG. 19 shows a mean probability of spike of wild-type (WT) and mutant (SOD1) cells. Cellular excitability was measured by probability of spiking during each blue light stimulation, and during no stimulation (spontaneous firing).

7. Diagnosis

FIG. 19 illustrates an output from measuring action potentials in cells affected by a mutation and control cells isogenic but for the mutation. In the illustrated example, a patient known to have SOD1A4V is studied and the bottom trace is obtained from cells of that patient's genotype. The top trace labeled "WT" refers to cells from that patient that were edited to be SOD1V4A and thus wild-type at the locus of the patient's known mutation but otherwise to provide the genetic context present in the patient. A clinician may diagnosis a neurodegenerative disease based on a signature spike train manifest by the patient's cells. Here, a difference between the signature observed in the patient's cells and the control signature may be correlated to a positive diagnosis of a neurodegenerative disease.

Any suitable method of correlating the patient's signature to a diagnosis may be used. For example, in some embodiments, visual inspection of a signature may be used. In certain embodiments, a computer system may be used to automatically evaluate that an observed signature of the test cells satisfies predetermined criteria for a diagnosis. Any suitable criteria can be used. For example, a computer system may integrate under the spike train for both the test cells and the control cells over a range of time of at least a few thousand ms and compare a difference between the results. Any suitable difference between the observed and expected signals can be used, for example, the difference may include a modified probability of a voltage spike in response to the stimulation of the cell relative to a control. In certain embodiments (e.g., FIG. 19) the difference between the observed signal and the expected signal comprises a decreased probability of a voltage spike in response to the stimulation of the cell relative to a control and an increased probability of a voltage spike during periods of no stimulation of the cell relative to a control. In one embodiment, systems and methods of the invention detect a decreased probability of a voltage spike in response to the stimulation of the cell relative to a control.

To give one example, a difference of at least 5% can be reported as indicative of an increased risk or diagnosis of a condition. In another example, a computer system can analyze a probability of spike at a certain time point (e.g., 5500 ms) and look for a statistically significant difference. In another example, a computer system can be programmed to first identify a maximal point in the WT spike train (control signature) and then compare a probability at that point in the control signature to a probability in the patient's test signature at the same point and look for a reportable difference (e.g., at least 5% different). One of skill in the art will recognize that any suitable criterion can be used in the comparison of the test signature to the control signature. In certain embodiments, a computer system is trained by machine learning (e.g., numerous instances of known healthy and known diseased are input and a computer system measures an average difference between those or an average signature pattern of a disease signature). Where the computer system stores a signature pattern for a disease phenotype, a diagnosis is supported when the computer system finds a match between the test signature and the control signature (e.g., <5% different or less than 1% different at some point or as integrated over a distance). While obtaining a control signature from a genome-edited cell line from the patient has been discussed, one of skill in the art will recognize that the control signature can be a template or documented control signature stored in computer system of the invention.

In certain embodiments, observation of a signature from a cell is used in a diagnosis strategy in which the observed signature phenotype contributes to arriving at a final diagnosis. For example, with certain disease of the nervous system such as ALS, different neuron types may be affected differently. In some embodiments, a diagnostic method includes comparing different neuron types from the same patient to diagnose a sub-type specific disease.

8. Additional Methods

Methods of the invention may include the use of tool/test compounds or other interventional tools applied to the observed cell or cells. Application of test compounds can reveal effects of those compounds on cellular electrophysiology. Use of a tool compounds can achieve greater specificity in diagnosis or for determining disease mechanisms, e.g. by blocking certain ion channels. By quantifying the impact of the compound, one can quantify the level of that channel in the cell.

With a tool or test compound, a cell may be caused to express an optical reporter of neural or electrical activity and may also be exposed to a compound such as a drug. A signature of the cell can be observed before, during, or after testing the compound. Any combination of different cells and cell types can be exposed to one or any combination of compounds, including different test compound controls. Multi-well plates, multi-locus spotting on slides, or other multi-compartment lab tools can be used to cross-test any combination of compounds and cell types.

In certain embodiments, tool compounds are added to cells and their effect on the cells is observed to distinguish possible diseases or causes or mechanisms of diseases. For example, where two or more cells in synaptic connection with one another are observed, extrinsic stimulation of an upstream cell should manifest as an action potential in a downstream cell. A compound that is known to inhibit neurotransmitter reuptake may be revealed to work on only certain neural subtypes thus indicating a specific disease pattern.

In some embodiments, methods of the invention are used to detect, measure, or evaluate synaptic transmission. A signature may be observed for a cell other than the cell to which direct stimulation was applied. In fact, using the signal processing algorithms discussed herein, synaptic transmission among a plurality of cells may be detected thus revealing patterns of neural connection. Establishing an assay that successfully detects firing of a downstream neuron upon stimulation of an upstream neuron can reveal, where the subject cell to be observed fails to fire upon stimulation of an upstream neuron, a disease or condition characterized by a failure of synaptic transmission.

Test compounds can be evaluated as candidate therapies to determine suitability of a treatment prior to application to patient. E.g. one can test epilepsy drugs to find the one that reverts the firing pattern back to wild-type. In some embodiments, the invention provides systems and methods for identifying possible therapies for a patient by testing compounds, which systems and methods may be employed as personalized medicine. Due to the nature of the assays described herein, it may be possible to evaluate the effects of candidate therapeutic compounds on a per-patient basis thus providing a tool for truly personalized medicine. For example, an assay as described herein may reveal that a patient suffering from a certain disease has neurons or neural subtypes that exhibit a disease-type physiological phenotype under the assays described herein. One or a number of different compounds may be applied to those neurons or neural subtypes. Cells that are exposed to one of those different compounds (or a combination of compounds) may exhibit a change in physiological phenotype from disease-type to normal. The compound or combination of compounds that affects the change in phenotype from disease-type to normal is thus identified as a candidate treatment compound for that patient.

Embodiments of the invention provide modified neurons and methods for the optical evaluation of diseases autism affecting electrically active cells such as neurons. In some embodiments, neurons and methods of the invention are used to evaluate a condition known to be associated with a genetic variant, or mutation.

Embodiments of the invention provide modified neurons and methods for the optical evaluation of diseases epilepsy affecting electrically active cells such as neurons. In some embodiments, neurons and methods of the invention are used to evaluate a condition known to be associated with a genetic variant, or mutation.

Embodiments of the invention relate to Alzheimer's. Alzheimer's disease is a neurodegenerative disease of uncertain cause (although mutations in certain genes have been linked to the disorder) and is one of the most common forms of dementia. Alzheimer's disease is discussed in Israel et al., 2012, Probing sporadic and familial Alzheimer's disease using induced pluripotent stem cells, Nature 482(7384):216-20; Muratore et al., 2014, The familial Alzheimer's disease APPV717I mutation alters APP processing and tau expression in iPSC-derived neurons, Human Molecular Genetics, in press; Kondo et al., 2013, Modeling Alzheimer's disease with iPSCs reveals stress phenotypes associated with intracellular Abeta and differential drug responsiveness, Cell Stem Cell 12(4):487-496; and Shi et al., 2012, A human stem cell model of early Alzheimer's disease pathology in Down syndrome, Sci Transl Med 4(124):124ra129, the contents of each of which are incorporated by reference. Systems and methods of the invention may be used to evaluate compounds such as corrector molecules for their effect on Alzheimer's affected cells.

The use of stem cell technology provides a clinically-relevant cell models of Alzheimer's and the use of microbial optogenetic constructs allows for rapid screening or detection of cellular physiologies and phenotypes. Methods of the invention can provide genetically modified neurons that can replicate Alzheimer's disease pathology in in vitro and in vivo conditions in order to develop and test Alzheimer disease drugs in human brain cells.

To recapitulate the disease phenotype, the neurons may be exposed to Aβ1-42. Additionally, prospective compounds such as antibodies against epitopes on Aβ may be studied by methods of the invention. For example, the BIIB037 antibody may be exposed to neurons using systems and methods of the invention. Optogenetic constructs provide for the optical study of both the toxicity of the Aβ peptide and the neuroprotective effects of prospective compounds. Thus methods of the invention provide a model system to study Alzheimer's disease pathology. FIG. 1 diagrams a method 101 for evaluating a condition according to embodiments of the invention. This may involve obtaining 107 a cell (e.g., purchasing PSCs and converting to neurons; biopsy from a person suspected of having the condition; etc.). Genome editing techniques (e.g., use of transcription activator-like effector nucleases (TALENs), the CRISPR/Cas system, zinc finger domains) may be used to create a control cell that is isogenic but-for a variant of interest. The cell and the control are converted into an electrically excitable cell such as a neuron. The cell may be converted to a specific neural subtype (e.g., motor neuron). The cells are caused to express 113 an optical reporter of neural activity. For example, the cell may be transformed with a vector comprising an optogenetic reporter and the cell may also be caused to express an optogenetic actuator (aka activator) by transformation. Optionally, a control cell may be obtained, e.g., by taking another sample, by genome editing, or by other suitable techniques. Using microscopy and analytical methods described herein, the cells are observed and specifically, the cells' response to stimulation 119 (e.g., optical, synaptic, chemical, or electrical actuation) may be observed. A cell's characteristic signature such as a neural response as revealed by a spike train may be observed 123. The observed signature is compared to a control signature and a difference (or match) between the observed signature and the control signature corresponds to a positive diagnosis of the condition.

In one exemplary embodiment discussed herein, neurons of the invention comprise a genome associated with Alzheimer's disease and are used for optical evaluation of Alzheimer's disease development, progression, and/or treatments.

In certain embodiments, the invention provides modified neurons and methods for the optical evaluation of diseases such as tuberous sclerosis affecting electrically active cells such as neurons. In some embodiments, neurons and methods of the invention are used to evaluate a condition known to be associated with a genetic variant, or mutation. Neurons of the invention may be human derived or derived from another animal and may be cultured in vitro or may be modified within a living animal, such as a mouse, in order to provide an in vivo disease model with optical actuators and reporters of neuronal action potential. In one exemplary embodiment discussed herein, neurons of the invention comprise a genome associated with tuberous sclerosis and are used for optical evaluation of tuberous sclerosis development, progression, and/or treatments.

In certain aspects, the invention relates to optogenetic methods for robust, biologically relevant assays with sufficient capacity for high throughput screening of ion channel modulators. Ion channels are therapeutic targets and may be modulated by a range of drugs. Ion transport mediated by ion channels is important in many fundamental physiological processes in the heart and the nervous system as well as for fluid secretion in the lung, GI tract and kidney, and other processes such as hormone secretion, the immune response, bone re-modeling and tumor cell proliferation. The physiological importance of ion channels is underlined by their involvement in a wide range of pathologies spanning all major therapeutic areas. For example, over 55 different inherited ion channel diseases, known as "channelopathies,"

have now been identified across cardiovascular, neuronal, neuromuscular, musculoskeletal, metabolic, and respiratory systems. Ion channels are typically multimeric, transmembrane proteins having separate pore-forming and accessory subunits (Ashcroft, 2006, Nature 440:440-7). Ion channels are often classified according to gating mechanism: voltage-gated channels are regulated by changes in the electrical potential difference in membrane potential whereas ligand- and sensory-gated channels respond to changes ligands and to mechanical or thermal stimuli, respectively.

High throughput screening of large chemical libraries generally may include cloning of the target protein which is abundantly expressed in a stable cell line in a form that closely resembles its native correlates. For ion channels this involves efficient expression, localization, and orientation of an appropriate combination of subunits.

Methods of the invention provide an optical alternative to patch clamp electrophysiology. Methods and the optogenetic constructs of the invention may be used for high throughput screening (HTS) of ion channels.

9. Disease Models

The invention provides methods for screening, detecting, and characterizing compounds in high-throughput cellular assays of cells expressing optogenetic proteins that initiate and report electrical activity in cells using light. Thus the invention provides high-capacity methods for primary screening of chemical libraries. These high-throughput assays provide robust electrophysiological measurements of cells without requiring patch clamp techniques. Since the described optogenetic constructs and pluripotent stem cell (PSC)-derived cells operate to provide the precision, temporal resolution, and voltage control required for monitoring effects of compounds, assays of the invention are compatible with primary screening and drug discovery. For the assays, a target protein may be cloned and expressed in a stable cell line of the invention. Thus the invention provides robust, biologically relevant assays with sufficient capacity for high throughput screening of compounds.

Aspects of the invention provide a method for determining an effect of a compound a neurological condition. The method includes presenting a compound to a sample comprising a plurality of neurons, wherein at least one of the plurality of neurons expresses an optical reporter of membrane electrical potential, and receiving—via a microscopy system—an optical signal generated by the optical reporter in response to optical stimulation of a light gated ion channel in the sample following presentation of said compound. The compound is identified as a candidate for treatment of the neurological condition based on said optical signal. The light gated ion channel may include an algal channelrhodopsin being expressed by a second neuron in synaptic communication with the at least one of the plurality of neurons. The light gated ion channel may include an algal channelrhodopsin being expressed by the at least one of the plurality of neurons. The optical reporter of membrane potential may include a microbial rhodopsin (e.g., with between 1 and 10 amino acid substitutions relative to a wild type form of the microbial rhodopsin). In some embodiments, the at least one of the plurality of neurons also expresses a genetically-encoded indicator of intracellular calcium level. The received optical signal may include a signal from the genetically-encoded indicator of intracellular calcium level. The neurological condition may be one of autism, epilepsy, Alzheimer's, amyotrophic lateral sclerosis, and tuberous sclerosis.

i. Autism

In certain embodiments, neurons and methods of the invention may be used to create disease models for in vitro investigation of neurodevelopmental disorders such as autism. Neurons may be derived from iPSCs taken from individuals suffering from the neurodevelopmental disorder or may be derived through genome editing by incorporating genotype associated with the neurodevelopmental disorder. In certain instances a test mutation, suspected of being associated with a neurodevelopmental disorder, may be incorporated into a neuron through genome editing and the resulting modified neuron may be observed for signs of disease to evaluate the test mutation for links to the disease.

In some embodiments, cell neuronal models of a disease, such as autism may be chosen based on the exhibition of neuronal phenotypes associated with autism, such as neurons with reduced expression of SHANK3 protein compared to a disease-free neuron, decreased synaptic function compared to a disease-free neuron, reduced number and increased length of dendritic spines compared to a disease-free neuron, and reduced thickness and length of postsynaptic density compared to a disease-free neuron. See Zoghbi, et al., 2012, Synaptic Dysfunction in Neurodevelopmental Disorders Associated with Autism and Intellectual Disabilities, Cold Spring Harb Perspect Biol. 4(3), J Neurol Sci. 217(1):47-54; incorporated by reference. Neuronal models of a disease such as autism may be selected based on genotypic characteristics such as a mutation to one or more of the following genes: SHANK3 (ProSAP2), CDH9, CDH10, MAPK3, SERT (SLC6A4), CACNA1G, GABRB3, GABRA4, EN2, the 3q25-27 locus, SLC25Al2, HOXA1, HOXA2, PRKCB1, MECP2, UBE3A, NLGN3, MET, CNTNAP2, FOXP2, GSTP1, PRL, PRLR, and OXTR.

In certain aspects, for example where modelled disease are non-monogenic, complex etiology and/or late onset, neurons of the invention may be cultured for extended periods, such as 1 month, 2 months, 3 months, 4 months or longer in order to simulate aging. See Sanchez-Danes, et al., 2012, Disease-specific phenotypes in dopamine neurons from human iPS-based models of genetic and sporadic Parkinson's disease, EMBO Mol Med, 4: 380-395, the contents of which are incorporated by reference. Cells of the invention may be transformed with optical reporters of membrane potential, reporters of intracellular calcium levels, light-gated ion channels, or a combination thereof. Cells may be monitored over time by inducing and observing action potentials and changes in intracellular calcium levels during disease progression in order to examine the neuronal effects of the subject condition, such as autism. Subject cells of the disease model may also be monitored pre and post application of various therapies in order to evaluate their effectiveness.

ii. Epilepsy

In certain embodiments, neurons and methods of the invention may be used to create disease models for in vitro investigation of neurological disorders such as epilepsy. Neurons may be derived from iPSCs taken from individuals suffering from the neurological disorder or may be derived through genome editing by incorporating a genotype associated with the neurological disorder. Disease models of the invention may be particularly useful in studying action potential generation and propagation and ion channel function before, during, and after an epileptic seizure. In certain instances a test mutation, suspected of being associated with a neurological disorder, may be incorporated into a neuron through genome editing and the resulting modified neuron may be observed for signs of disease to evaluate the test mutation for links to the disease.

In some embodiments, cell neuronal models of a disease, such as epilepsy or Dravet syndrome, may be chosen based on the exhibition of neuronal phenotypes associated with the disease, such as neurons with diminished voltage-gated sodium channel function compared to disease-free neurons or hyperexcitability. See Kearney, 2014, The More, the Better: Modeling Dravet Syndrome With Induced Pluripotent Stem Cell-Derived Neurons, Epilepsy Curr. 14(1): 33-34; incorporated by reference. Neuronal models of a disease such as epilepsy or Dravet syndrome may be selected based on genotypic characteristics such as a mutation to one or more of the following genes: SCN1A, WWOX, PRRT2, KCNC1, STX1B, CARS2, STXB1, KCNQ2, CDKL5, ARX, SPTAN, BRAT1, KCNQ3, SCN2A, GABA receptors, NIPA2, CDKL5, PCDH19, and NAV1.1.

In certain aspects, for example where modelled disease are non-monogenic, complex etiology and/or late onset, neurons of the invention may be cultured for extended periods, such as 1 month, 2 months, 3 months, 4 months or longer in order to simulate aging. See Sanchez-Danes, et al., 2012, Disease-specific phenotypes in dopamine neurons from human iPS-based models of genetic and sporadic Parkinson's disease, EMBO Mol Med, 4: 380-395, the contents of which are incorporated by reference. Cells of the invention may be transformed with optical reporters of membrane potential, reporters of intracellular calcium levels, light-gated ion channels, or a combination thereof. Cells may be monitored over time by inducing and observing action potentials and changes in intracellular calcium levels during disease progression in order to examine the neuronal effects of the subject condition, such as epilepsy. Subject cells of the disease model may also be monitored pre and post application of various therapies in order to evaluate their effectiveness.

iii. ALS

In certain embodiments, neurons and methods of the invention may be used to create disease models for in vitro investigation of neuronal diseases such as ALS. Neurons may be derived from iPSCs taken from individuals suffering from the neuronal disease or may be derived through genome editing by incorporating genotype associated with the neuronal disease. In certain instances a test mutation, suspected of being associated with a neuronal disease, may be incorporated into a neuron through genome editing and the resulting modified neuron may be observed for signs of disease to evaluate the test mutation for links to the disease. In some embodiments, cell neuronal models of a disease, such as ALS disease may be chosen based on the exhibition of neuronal phenotypes associated with ALS, such as motor neurons with Bunina bodies, which are cystatin C-containing inclusions in the cell body; 'Lewy body-like inclusions' (LBIs), 'Skein-like inclusions' (SLIs) inclusions, and/or clear signs of degeneration, including very short or absent neurites, vacuolated soma, a fragmented nucleus and cleaved caspase-3. See He, et al., 2004, Expression of peripherin in ubiquinated inclusions of amyotrophic lateral sclerosis, J Neurol Sci. 217(1):47-54; Kawashima, et al., 1998, Skein-like inclusions in the neostriatum from a case of amyotrophic lateral sclerosis with dementia, Acta Neuropathol 96(5):541-5; Okamoto, et al., 1993, Bunina bodies in amyotrophic lateral sclerosis immunostained with rabbit anti-cystatin C serum, Neurosci Lett. 162(1-2):125-8; each of which is incorporated by reference. Neuronal models of a disease such as ALS may be selected based on genotypic characteristics such as a mutation to one or more of the following genes: C9orf72, SOD1, TARDBP, FUS, UBQL2, ALS2, and SETX.

In certain aspects, for example where modelled disease are non-monogenic, complex etiology and/or late onset, neurons of the invention may be cultured for extended periods, such as 1 month, 2 months, 3 months, 4 months or longer in order to simulate aging. See Sánchez-Danés, et al. Cells of the invention may be transformed with optical reporters of membrane potential, reporters of intracellular calcium levels, light-gated ion channels, or a combination thereof. Cells may be monitored over time by inducing and observing action potentials and changes in intracellular calcium levels during disease progression in order to examine the neuronal effects of the subject condition, such as ALS. Subject cells of the disease model may also be monitored pre and post application of various therapies in order to evaluate their effectiveness.

iv. Tuberous Sclerosis

In certain embodiments, neurons and methods of the invention may be used to create disease models for in vitro investigation of genetic disorders such as tuberous sclerosis. Neurons may be derived from iPSCs taken from individuals suffering from the neurological disorder or may be derived through genome editing by incorporating genotype associated with the neurological disorder. Disease models of the invention may be particularly useful in studying action potential generation and propagation and ion channel function before, during, and after an epileptic seizure. In certain instances a test mutation, suspected of being associated with a neurological disorder, may be incorporated into a neuron through genome editing and the resulting modified neuron may be observed for signs of disease to evaluate the test mutation for links to the disease.

In some embodiments, cell neuronal models of a disease, such as tuberous sclerosis may be chosen based on the exhibition of neuronal phenotypes associated with tuberous sclerosis, such as enlarged size compared to a disease-free neuron, increased phospho-S6 expression, prominent lysosomes, more microfilaments and microtubules compared to a disease-free neuron, fewer lipofuscin granules compared to a disease-free neuron, and immunoreactivity for TSC2 gene product, tuberin, vimentin or glial fibrillary acidic protein. See Meikle, et al., 2007; Arai, et al., 1999, A comparison of cell phenotypes in hemimegalencephaly and tuberous sclerosis, Acta Neuropathol. 98(4):407-13; each of which is incorporated by reference. Neuronal models of a disease such as tuberous sclerosis may be selected based on genotypic characteristics such as a mutation to one or more of the following genes: TSC1 or TSC2.

In certain aspects, for example where modelled disease are non-monogenic, complex etiology and/or late onset, neurons of the invention may be cultured for extended periods, such as 1 month, 2 months, 3 months, 4 months or longer in order to simulate aging. See Sanchez-Danes, et al., 2012, Disease-specific phenotypes in dopamine neurons from human iPS-based models of genetic and sporadic Parkinson's disease, EMBO Mol Med, 4: 380-395, the contents of which are incorporated by reference. Cells of the invention may be transformed with optical reporters of membrane potential, reporters of intracellular calcium levels, light-gated ion channels, or a combination thereof. Cells may be monitored over time by inducing and observing action potentials and changes in intracellular calcium levels during disease progression in order to examine the neuronal effects of the subject condition, such as tuberous sclerosis.

Subject cells of the disease model may also be monitored pre and post application of various therapies in order to evaluate their effectiveness.

v. NGN2 Neurons

Aspects of the invention provide cellular disease models in which stem cells may be converted into functional neurons by forced expression of a single transcription factor and then also caused to express optogenetic reporters or actuators of neural activity. A transcription factor such as neurogenin-2 (NgN2) or NeurD1 introduced into a pluripotent stem cell by transfection is expressed, causing the cell to differentiate into a neuron. Additionally or separately an optogenetic construct that includes an optical reporter of intracellular calcium as well as an optical actuator or reporter of membrane potential is expressed.

10. Systems of the Invention

Figure 20:
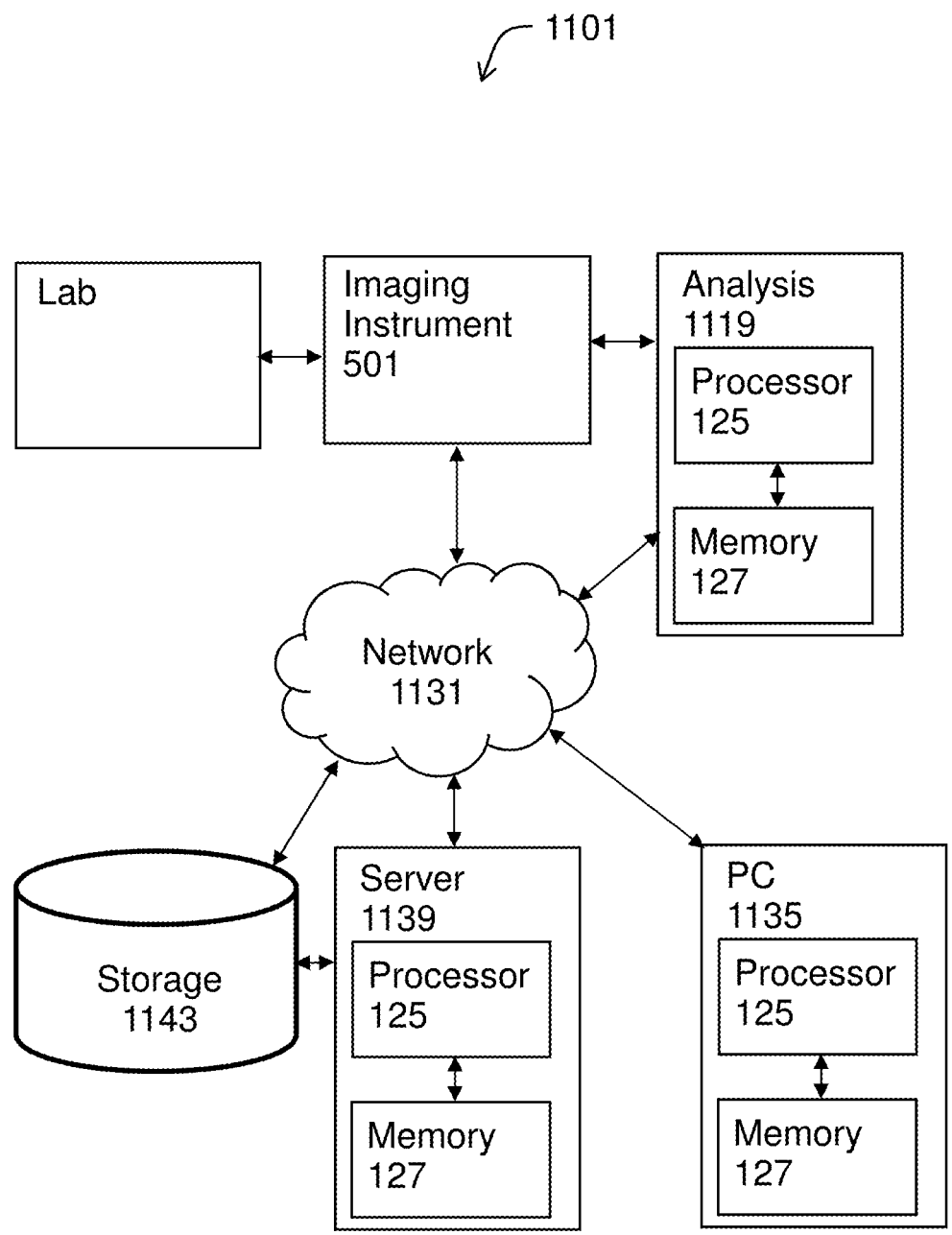
FIG. 20 presents a system useful for performing methods of the invention.

FIG. 20 presents a system 1101 useful for performing methods of the invention. Results from a lab (e.g., transformed, converted patient cells) are loaded into imaging instrument 501. Imaging instrument 501 is operably coupled to an analysis system 1119, which may be a PC computer or other device that includes a processor 125 coupled to a memory 127. A user may access system 1101 via PC 1135, which also includes a processor 125 coupled to a memory 127. Analytical methods described herein may be performed by any one or more processor 125 such as may be in analysis system 1119, PC 1135, or server 1139, which may be provided as part of system 1101. Server 1139 includes a processor 125 coupled to a memory 127 and may also include optional storage system 1143. Any of the computing device of system 1101 may be communicably coupled to one another via network 1131. Any, each, or all of analysis system 1119, PC 1135, and server 1139 will generally be a computer. A computer will generally include a processor 125 coupled to a memory 127 and at least one input/output device.

A processor 125 will generally be a silicon chip microprocessor such as one of the ones sold by Intel or AMD.

Memory 127 may refer to any tangible, non-transitory memory or computer readable medium capable of storing data or instructions, which—when executed by a processor 125—cause components of system 1101 to perform methods described herein.

Typical input/output devices may include one or more of a monitor, keyboard, mouse, pointing device, network card, Wi-Fi card, cellular modem, modem, disk drive, USB port, others, and combinations thereof.

Generally, network 1131 will include hardware such as switches, routers, hubs, cell towers, satellites, landlines, and other hardware such as makes up the Internet.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Optical Differentiation of a Motor Neuron Model of Amyotrophic Lateral Sclerosis (ALS) Arising from a Monogenic Mutation in the SOD1 Gene (SOD1A4V)

Methods of the invention were employed to evaluate the effects of a mutation on a patient's cells in the genetic context of that patient. ALS is a fatal neurodegenerative disease that affects pyramidal neurons in the motor cortex and lower motor neurons that originate in the brainstem and spinal cord. See Musaro, 2010, State of the art and the dark side of amyotrophic lateral sclerosis, WJBC 1(5):62-68. Typical manifestations include degeneration of motor neurons leading to muscle weakness and atrophy, speech and swallowing disabilities, paralysis, and death by respiratory failure. ALS is classified into sporadic or familial forms. It is thought that many of the familiar forms are caused by mutations in the Cu/Zn superoxide dismutase-1 (SOD1) protein. Another gene that may be used is C9orf72 where an incompletely penetrant mutation is sometimes associated with symptoms. The discussion here relates to SOD1 and one of skill in the art will recognize that the techniques apply for mutations in other genes such as C9orf72. SOD1 converts the toxic mitochondrial by-product superoxide into water or hydrogen peroxide. Evidence suggests SOD1 mutations are gain-of-function mutations. See Rotunno & Bosco, 2013, An emerging role for misfolded wild-type SOD1 in sporadic ALS pathogenesis, Front Cell Neurosci 7:a253; and Saccon, et al., 2013, Is SOD1 loss of function involved in amyotrophic lateral sclerosis?, Brain 136:2342-2358. It is known that other gene defects besides SOD1 mutations can cause ALS. See Pasinelli & Brown, 2006, Molecular biology of amyotrophic lateral sclerosis: insights from genetics, Nat Rev Neurosci 7:710-723; and Blokhuis et al., 2013, Protein aggregation in amyotrophic lateral sclerosis, Acta Neuropathol 125:777-794. Thus mere identification of the presence of a single mutation may prove inadequate for diagnosing and treating a patient and it may prove valuable to study the phenotypic consequences of such a mutation with the patient's actual genetic consequence. Contemporary research supports treatment strategies that aim to slow disease progression by targeting known genes, physiological pathways, and proteins. For more discussion, see Gordon, 2013, Amyotrophic later sclerosis: an update for 2013 clinical features, pathophysiology, management, and therapeutic trials, Aging and Disease 4(5):295-310. The following protocol documented an effect of SOD1A4V on motor neurons in a cell line from a person with an ALS diagnosis known to have SOD1A4V.

(1) Fibroblasts were taken from a patient diagnosed with ALS and confirmed mutation in SOD1.

(2) Fibroblasts were converted to induced pluripotent stem (iPS) cells.

(3) A second genetically corrected line (Sod1V4A) was generated using zinc finger domains resulting in two otherwise isogenic lines.

(4) Diseased and corrected iPS cells were differentiated into motor neurons using embryoid bodies.

(5) Differentiated motor neurons were dissociated and plated onto glass coverslips coated with poly-d-lysine and laminin (6) Motor neurons were fed with neurobasal medium supplemented with N2, B27, GDNF, BDNF, and CTNF.

(7) After 4 days in culture, neurons were infected with lenti-virus bearing a genetically encoded fluorescent voltage reporter (QuasAr2) and optical voltage actuator (CheRiff).

(8) Neurons were further matured for 8-10 days post infection.

(9) Neurons were imaged on a high resolution microscope with 640 nm laser (600 W/cm) for voltage imaging and excited with a 488 nm laser (20-200 mW/cm).

(10) A pulse sequence of red and blue light was used to record action potentials under increasing optical stimulation of voltage (FIG. 6).

(11) A population of cells was measured from diseased and corrected motor neurons.

(12) Individual cells were isolated in a field of view using independent component analysis (FIGS. 7-10).

(13) Action potentials were identified by removing photobleaching, subtracting a median filtered trace, and isolating data above a noise threshold.

(14) Cellular excitability was measured by probability of spiking during each blue light stimulation, and during no stimulation (spontaneous firing) (FIG. 19).

What is claimed is:

1. A method for determining an effect of a compound on a neurological condition, the method comprising:
presenting a compound selected for treating a neurological condition to a cell sample exhibiting a genotype associated with the neurological condition, the cell sample comprising a plurality of neurons, wherein at least one of the plurality of neurons expresses an optical reporter of membrane electrical potential;
optically stimulating an optogenetic actuator in the sample following presentation of the compound, wherein the optogenetic actuator is a light gated ion channel;
generating an optical signal in response to the optical stimulation of the light gated ion channel using the optical reporter;
receiving, via a microscopy system, the optical signal generated by the optical reporter;
analyzing the optical signal generated by the optical reporter with respect to a control signal obtained from a control cell sample not exhibiting a genotype associated with the neurological condition; and
identifying the compound as a candidate for treatment of the neurological condition based on the analysis of said optical signal with respect to the control signal.

2. The method of claim 1, wherein a plurality of samples are exposed to a plurality of different compounds.

3. The method of claim 1, wherein the light gated ion channel comprises an algal channelrhodopsin being expressed by a second neuron in synaptic communication with the at least one of the plurality of neurons, and the optical reporter of membrane potential comprises a microbial rhodopsin with between 1 and 10 amino acid substitutions relative to a wild type form of the microbial rhodopsin.

4. The method of claim 3, wherein the at least one of the plurality of neurons also expresses a genetically-encoded indicator of intracellular calcium level, and
wherein the receive optical signal includes a signal from the genetically-encoded indicator of intracellular calcium level, and further wherein the neurological condition is any one of autism, epilepsy, Alzheimer's, amyotrophic lateral sclerosis, or tuberous sclerosis.

5. The method of claim 1, wherein each of the plurality of neurons is caused to express both the optical reporter of membrane electrical potential and the light gated ion channel.

6. The method of claim 5, further comprising transforming the neurons with a vector that includes a nucleic acid encoding the optical reporter of membrane electrical potential and the light gated ion channel.

7. The method of claim 1, wherein the neurological condition is selected from the group consisting of Cockayne syndrome, Down Syndrome, Dravet syndrome, familial dysautonomia, Fragile X Syndrome, Friedreich's ataxia, Gaucher disease, hereditary spastic paraplegias, Machado-Joseph disease, Phelan-McDermid syndrome (PMDS), polyglutamine (polyQ)-encoding CAG repeats, spinal muscular atrophy, Timothy syndrome, Alzheimer's disease, frontotemporal lobar degeneration, Huntington's disease, multiple sclerosis, Parkinson's disease, spinal and bulbar muscular atrophy, and amyotrophic lateral sclerosis.

8. The method of claim 1, further comprising performing the presenting, optically stimulating, generating, and receiving steps on a control sample, wherein the neurons in the cell sample are isogenic with cells in the control sample but for a mutation.

9. The method of claim 1, wherein receiving the optical signal comprises observing a cluster of cells with a microscope and using a computer to isolate a signal generated by the optical reporter from among a plurality of signals from the cluster of cells.

10. The method of claim 9, wherein the computer isolates the signal by performing an independent component analysis and identifying a spike train produced by the neuron.

11. The method of claim 10, further comprising using the microscopy system to obtain an image of a plurality of clusters of cells.

* * * * *